(12) United States Patent
Gayl

(10) Patent No.: US 10,869,628 B2
(45) Date of Patent: Dec. 22, 2020

(54) DEVICE AND METHOD FOR WHOLE-MIND COGNITIVE INTERFACE

(71) Applicant: Franz J. Gayl, Burke, VA (US)

(72) Inventor: Franz J. Gayl, Burke, VA (US)

(*) Notice: Subject to any disclaimer, the term of this patent is extended or adjusted under 35 U.S.C. 154(b) by 643 days.

(21) Appl. No.: 15/622,402

(22) Filed: Jun. 14, 2017

(65) Prior Publication Data

US 2018/0360366 A1 Dec. 20, 2018

(51) Int. Cl.
| | | |
|---|---|---|
| *A61B 5/04* | (2006.01) | |
| *A61N 1/02* | (2006.01) | |
| *A61B 5/00* | (2006.01) | |
| *A61F 2/28* | (2006.01) | |
| *A61B 5/05* | (2006.01) | |
| *A61B 90/98* | (2016.01) | |
| *A61F 4/00* | (2006.01) | |

(52) U.S. Cl.
CPC .......... *A61B 5/4064* (2013.01); *A61B 5/0017* (2013.01); *A61B 5/0042* (2013.01); *A61B 5/0086* (2013.01); *A61B 5/04001* (2013.01); *A61B 5/05* (2013.01); *A61B 5/6803* (2013.01); *A61B 5/6868* (2013.01); *A61B 5/7264* (2013.01); *A61B 90/98* (2016.02); *A61F 2/2875* (2013.01); *A61F 4/00* (2013.01); *A61B 2562/028* (2013.01); *A61B 2562/0238* (2013.01); *A61B 2562/04* (2013.01)

(58) Field of Classification Search
CPC . A61B 5/0042; A61B 5/04001; A61B 5/4064; A61B 5/6868
See application file for complete search history.

(56) References Cited

U.S. PATENT DOCUMENTS

| | | | | |
|---|---|---|---|---|
| 2005/0245806 | A1* | 11/2005 | Singhal | A61B 5/107 600/407 |
| 2011/0301665 | A1* | 12/2011 | Mercanzini | A61B 17/34 607/45 |
| 2013/0046148 | A1* | 2/2013 | Tathireddy | A61B 5/04001 600/300 |
| 2014/0094674 | A1* | 4/2014 | Nurmikko | A61N 1/37217 600/378 |
| 2015/0057736 | A1* | 2/2015 | Zachar | A61N 5/04 607/154 |
| 2016/0150963 | A1* | 6/2016 | Roukes | A61B 5/6868 600/476 |
| 2016/0278687 | A1* | 9/2016 | Xia | A61B 5/4064 |
| 2019/0282817 | A1* | 9/2019 | Muller | A61N 1/37223 |

* cited by examiner

*Primary Examiner* — Christopher A Flory
*Assistant Examiner* — Nathan A Baldwin
(74) *Attorney, Agent, or Firm* — Maier & Maier, PLLC

(57) ABSTRACT

A method and apparatus for whole-mind cognitive interface. Such a system includes a bodily-integrated artificial cranium, computer, RF antenna, and transceiver array to seamlessly augment the human brain with artificial intelligence (AI) and permit enhanced cognitive functions, and human host feed-back-based neurological rewiring.

20 Claims, 48 Drawing Sheets

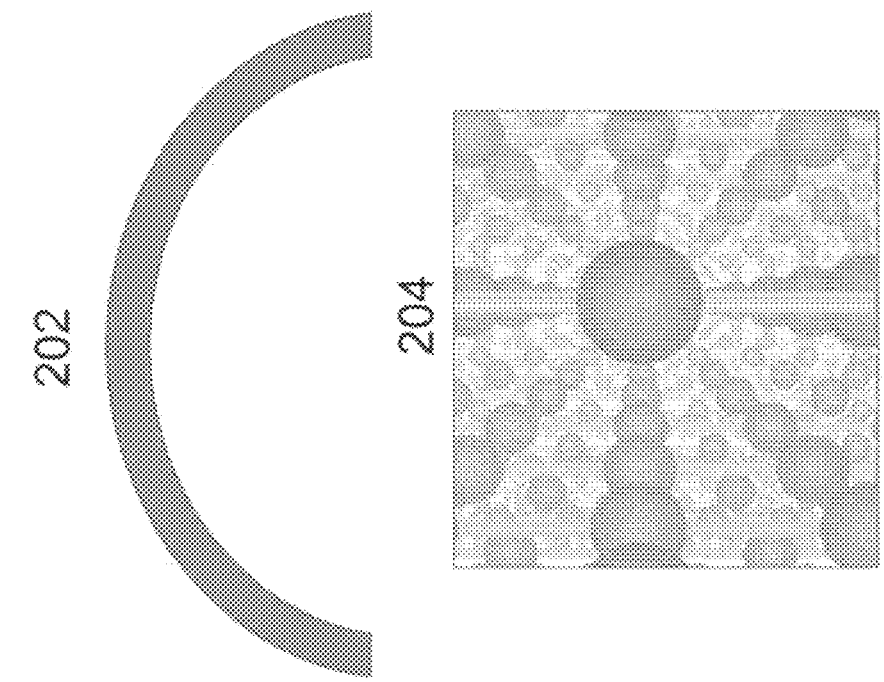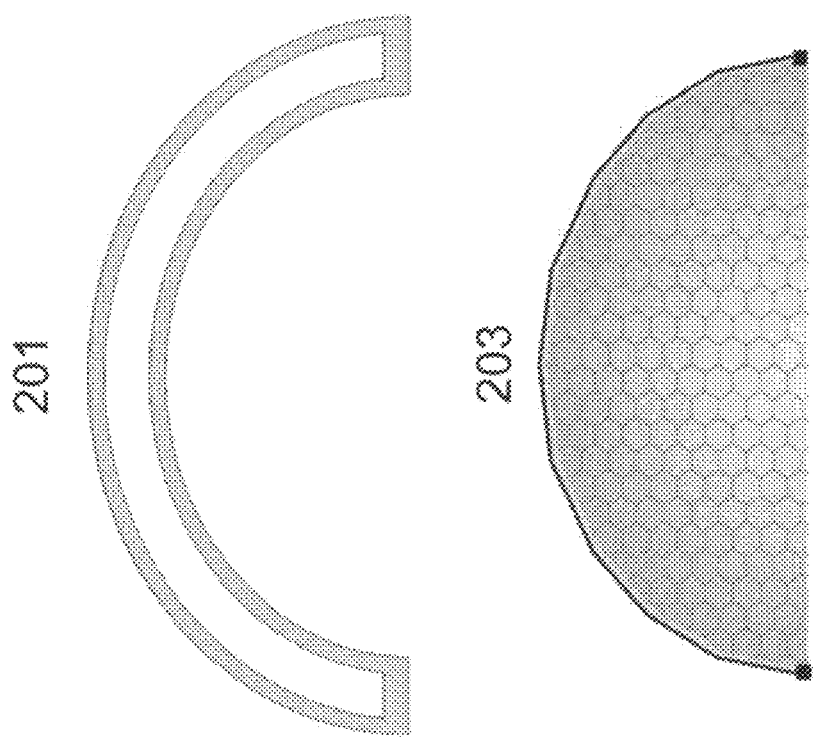
Fig. 2

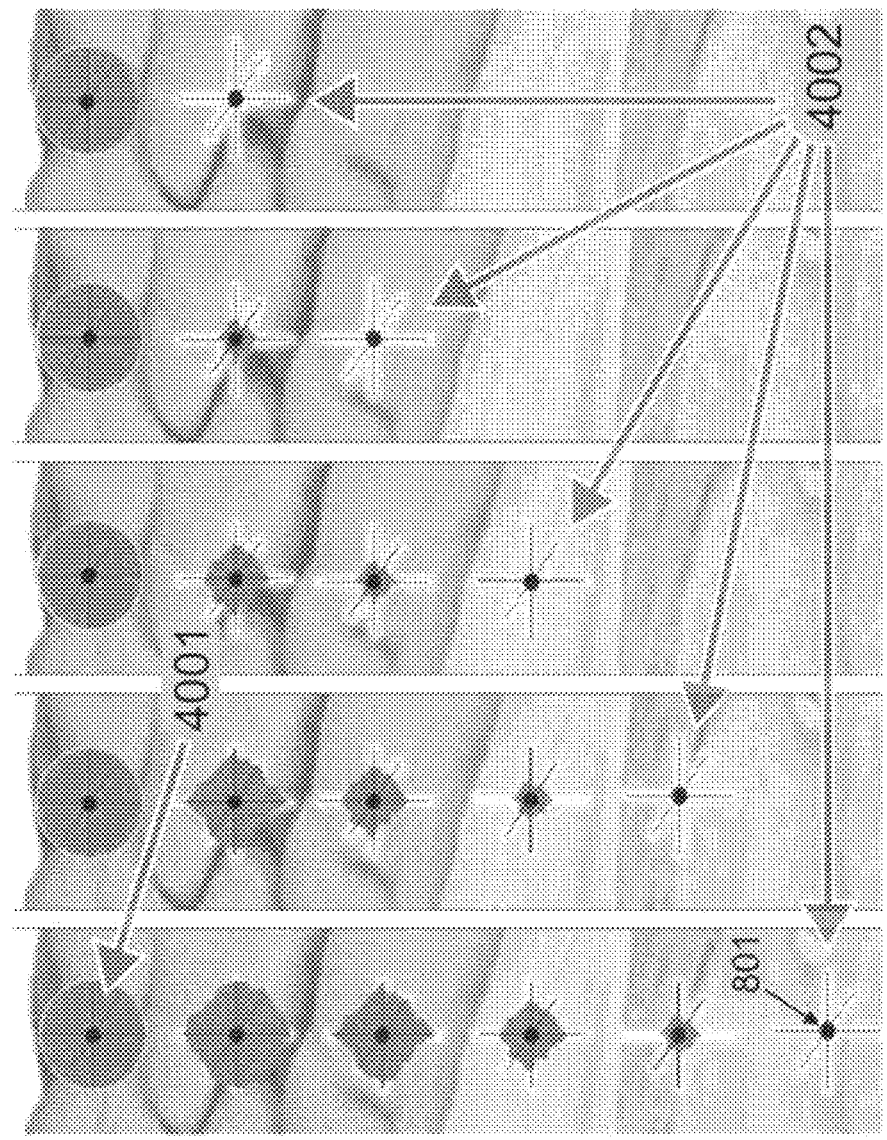

DEVICE AND METHOD FOR WHOLE-MIND COGNITIVE INTERFACE

BACKGROUND

The human brain has billions of neurons; the brain's activity is a function of the interconnections between the neurons. Each neuron functions as an organic transceiver. Referring to exemplary FIG. 1, in transmission mode, the neuron emits an RF signal from the Axon Hillock 101 during an action potential spike event (a natural neuron event). In receiver mode, the dendritic trees 102 of neurons on specific regions harvest EM energy emitted from the Axon Hillock of a different neuron. Research has been conducted in an attempt to clearly define the working process of the neural network in order to either treat mental diseases such as Post Traumatic Stress Disorder (PTSD), Substance Abuse and Addiction (SA), Alzheimer's disease (AD), etc., or to enhance brain function. However, because the human brain has approximately one hundred billion neurons, the sophistication of the neural network is still an uncharted territory.

SUMMARY

According to at least one exemplary embodiment, a device and a method for whole-mind cognitive interface may be described. Such a device and method may be able to seamlessly augment the human brain with artificial intelligence (AI) and permit enhanced cognitive functions and human host feedback-based neurological rewiring.

Such a device for whole-mind cognitive interface may include: an artificial cranium cap; a hub that is nested inside the artificial cranium cap, which locates at least one natural neuron event in a brain, records at least one of an instantaneous state of mind (ISOM) and a series of ISOMs by the located at least one natural neuron event, and replays the at least one of the recorded ISOM and the recorded series of ISOMs by generating at least one artificial neuron activity in the brain and generating the at least one artificial neuron activity at a predetermined location of the brain; a phased array antenna that is nested on an internal surface of the artificial cranium cap which, by controlling the hub, detects at least one electromagnetic signal from the at least one natural neuron event in the brain and transmits the at least one electromagnetic signal for the at least one artificial neuron activity; a plurality of 3D array nodes that are placed around the cranium which, by controlling of the hub, detect the at least one electromagnetic signal from the at least one natural neuron event and transmit at least one of the optical signals and the electromagnetic signals for the at least one artificial neuron activity.

Another exemplary embodiment can describe a method of whole-mind cognitive interface. The method may include: locating, by a hub in an artificial cranium cap, at least one natural neuron event in a brain; recording, by the hub, at least one of an instantaneous state of mind (ISOM) and a series of ISOMs by the located at least one natural neuron event; replaying, by the hub, the at least one of the recorded ISOM and the recorded series of ISOMs by generating at least one artificial neuron activity in the brain; and generating, by the hub, the at least one artificial neuron activity at a predetermined location of the brain. According to an exemplary embodiment, the at least one natural neuron event is located by using at least one of a phased array antenna and a plurality of 3D array nodes, and the phased array antenna that is nested on an internal surface of the artificial cranium cap, by controlling of the hub, detects at least one electromagnetic signal from the at least one natural neuron event and transmits the at least one electromagnetic signal for the at least one artificial neuron activity. Also, in an exemplary embodiment, the plurality of 3D array nodes that are placed around the cranium, by controlling of the hub, detects the at least one electromagnetic signal from the at least one natural neuron event and transmits at least one of optical signals and the electromagnetic signals for the at least one artificial neuron activity.

BRIEF DESCRIPTION OF THE FIGURES

Advantages of the embodiments of the present invention will be apparent from the following detailed descriptions of the exemplary embodiments thereof, which description should be considered in conjunction with the accompanying drawings in which like numerals indicate like elements, in which:

Exemplary FIG. 1 may show exemplary functions of a neuron as an organic transceiver;

Figure 3:
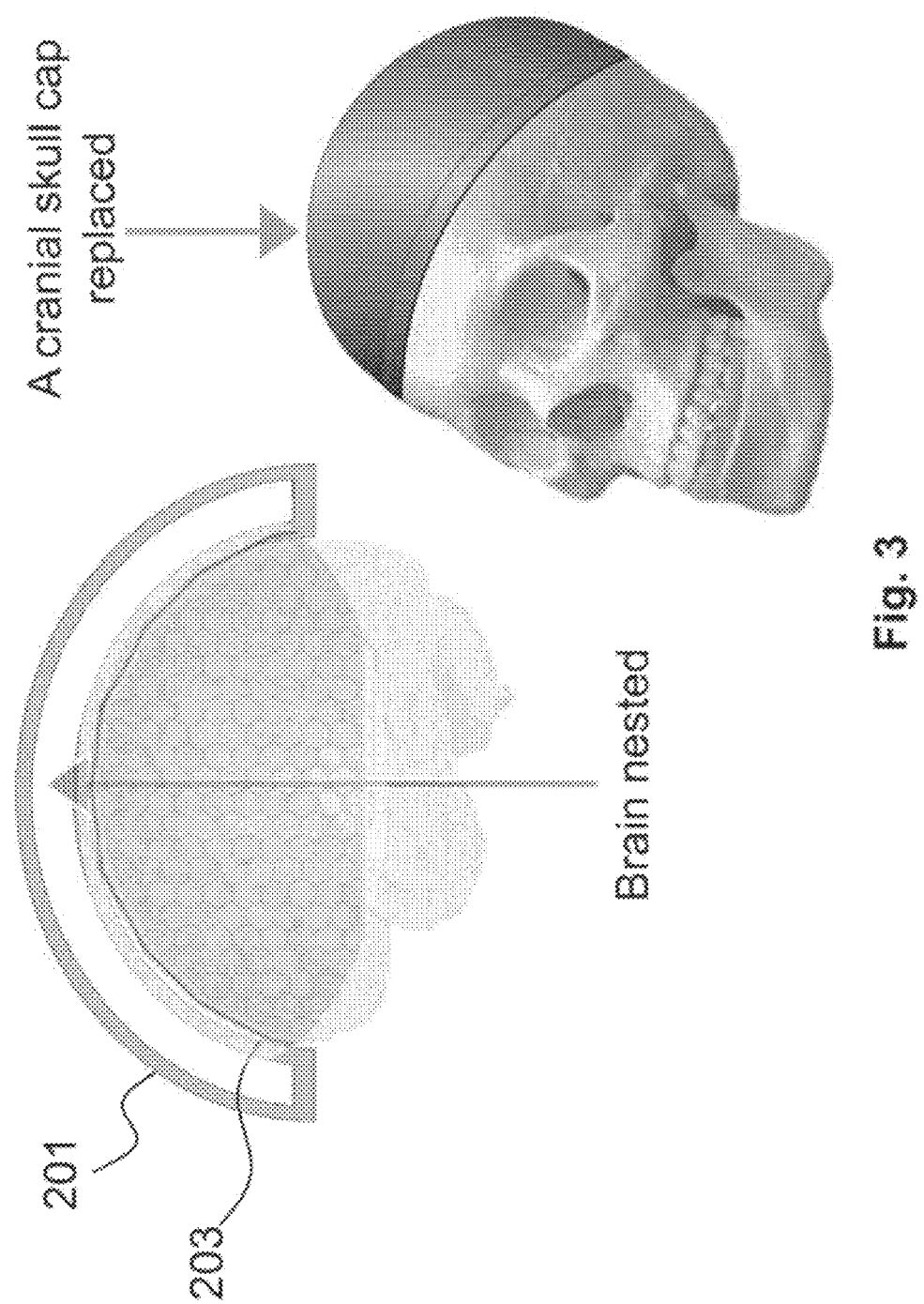
Figure 4:
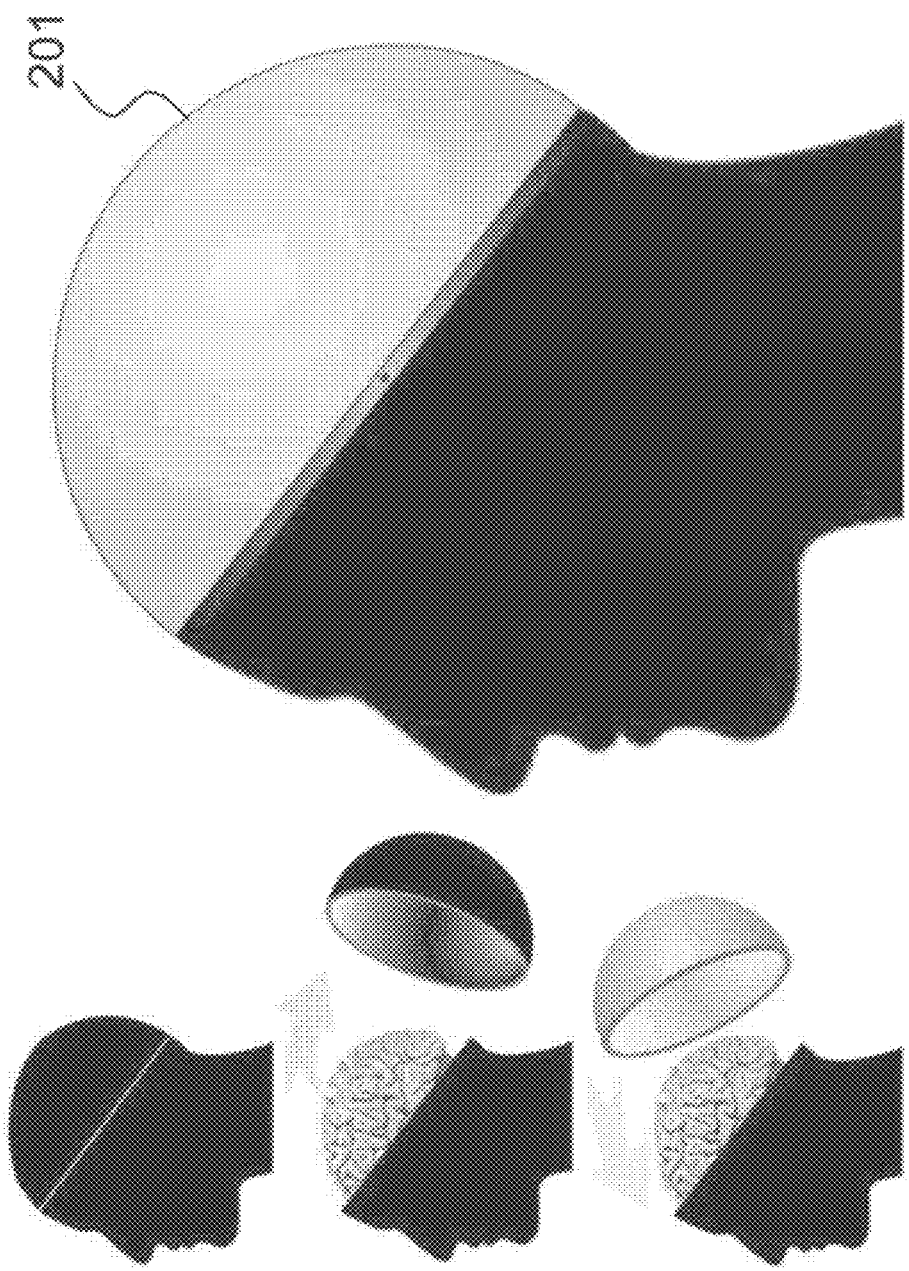
Figure 5:
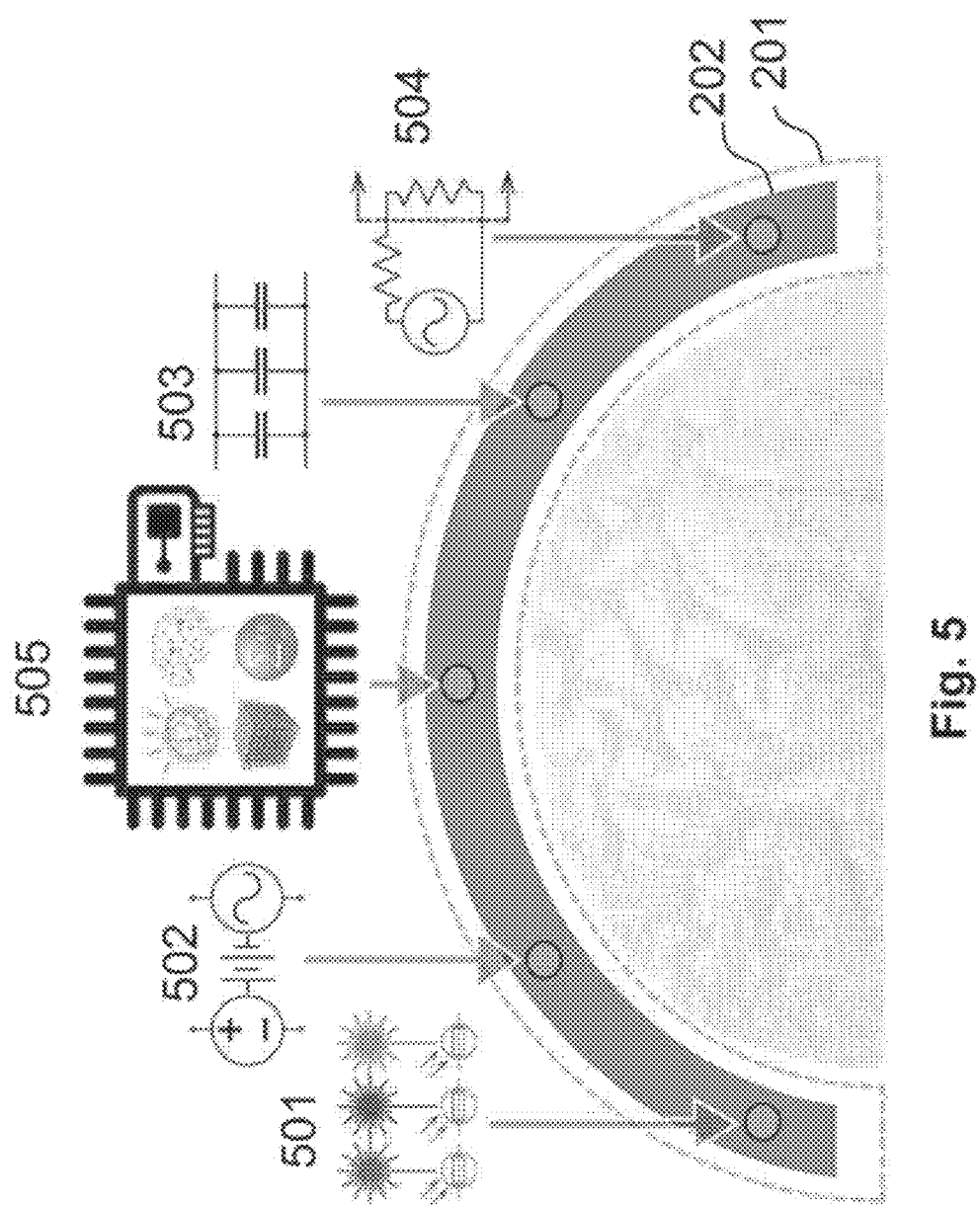
Figure 6:
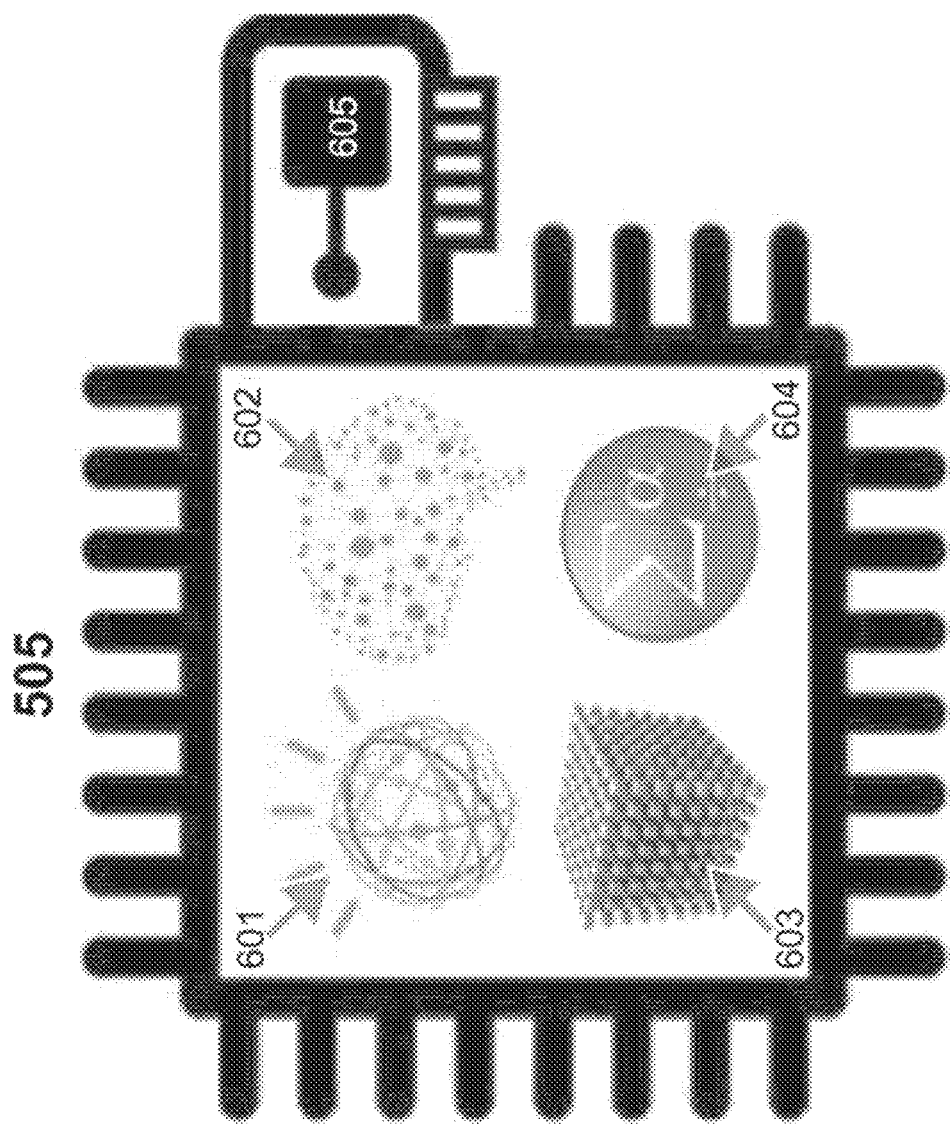
Figure 7:
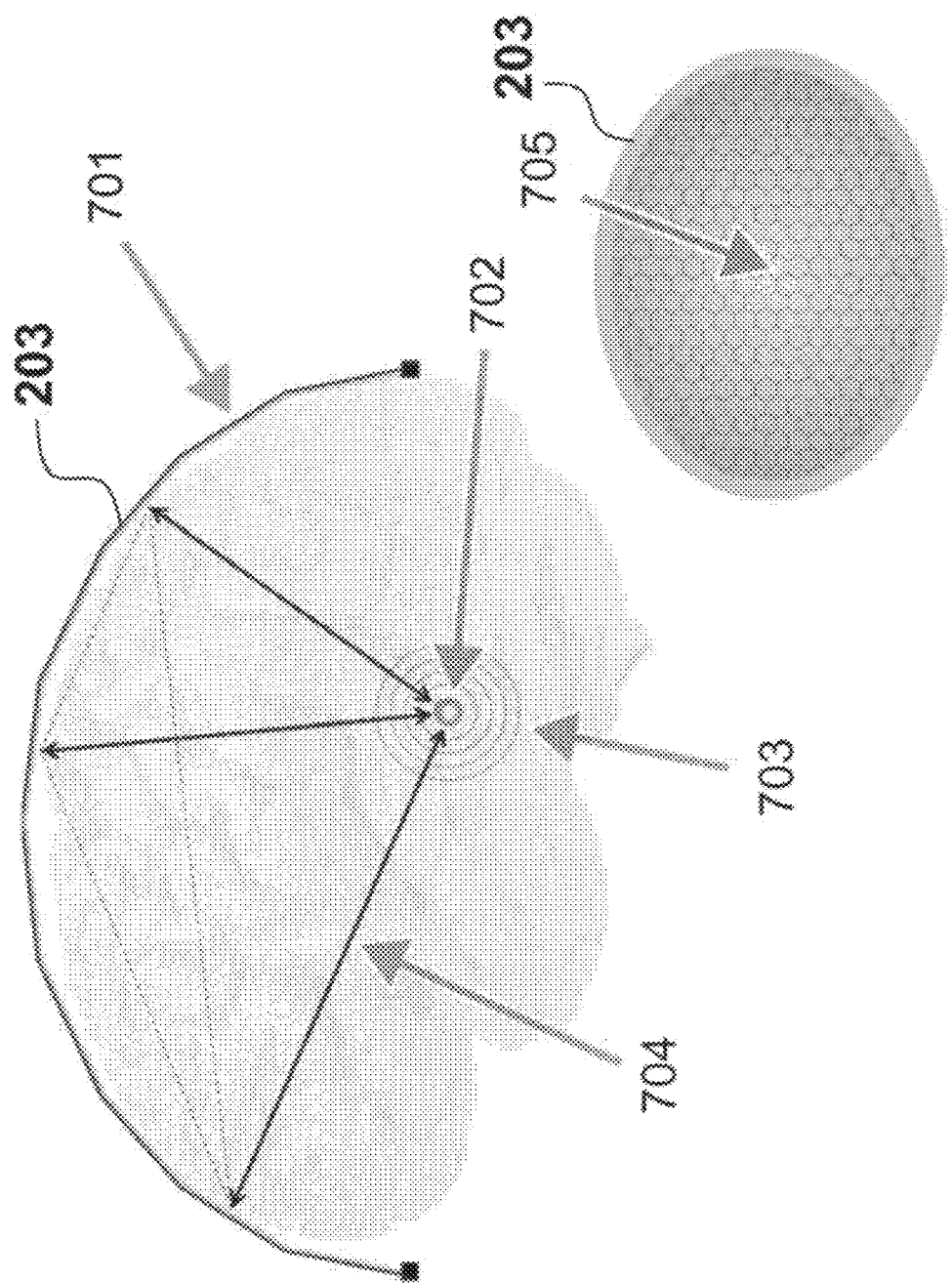
Figure 8:
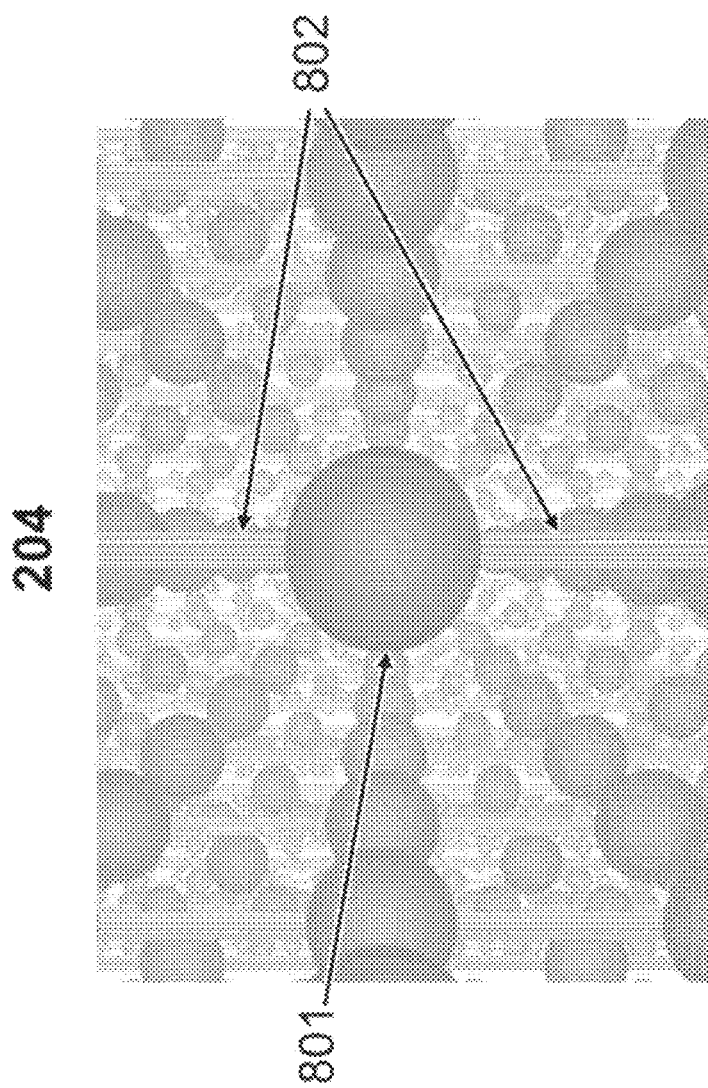
Figure 9:
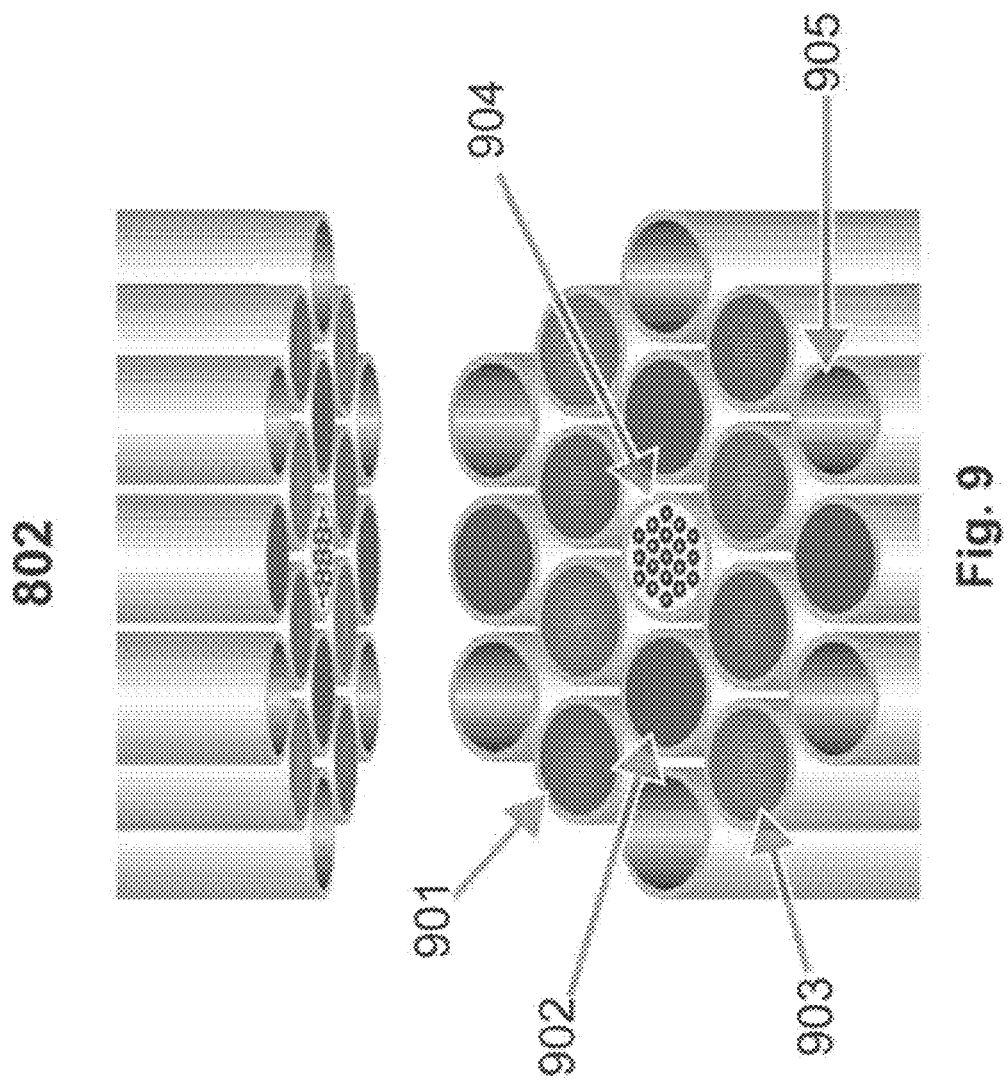
Figure 10:
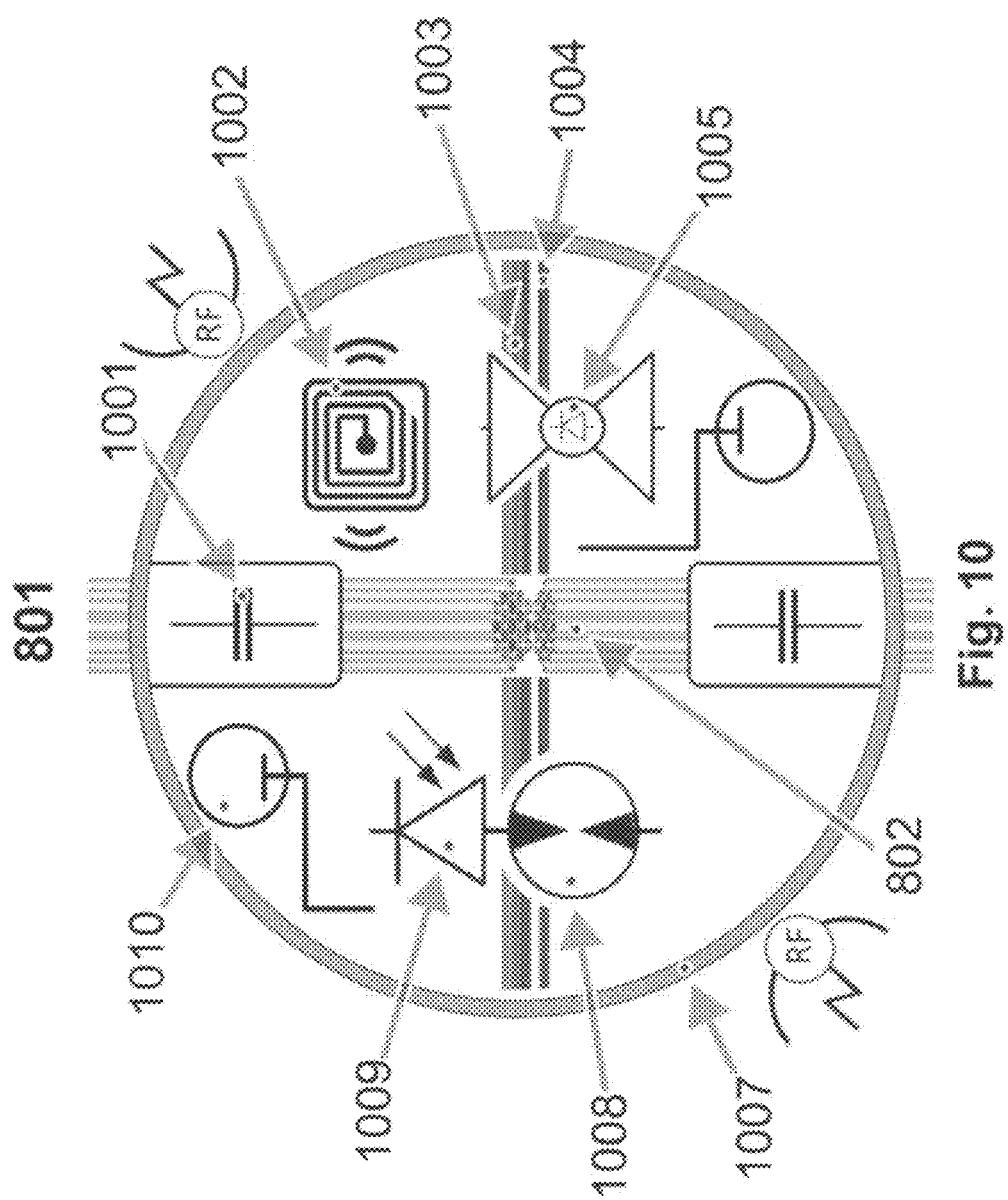
Figure 11:
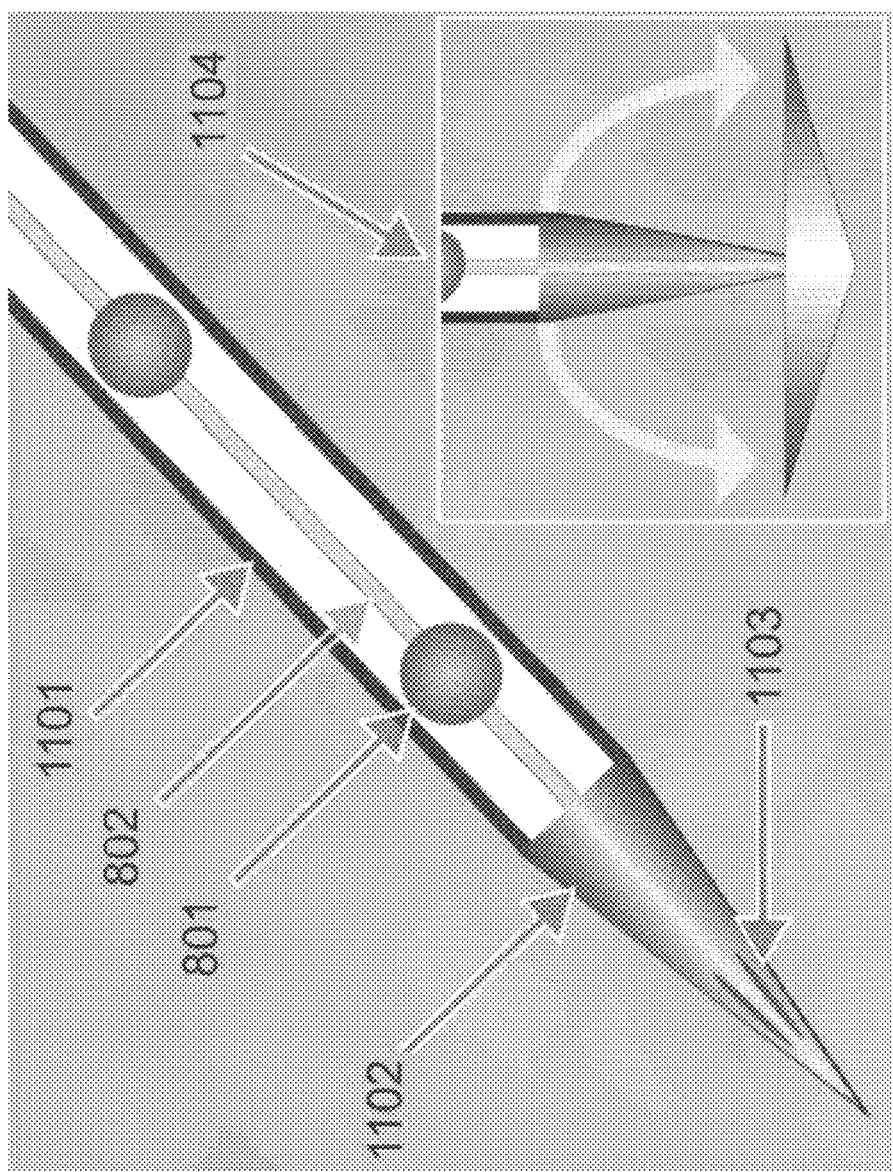
Figure 12:
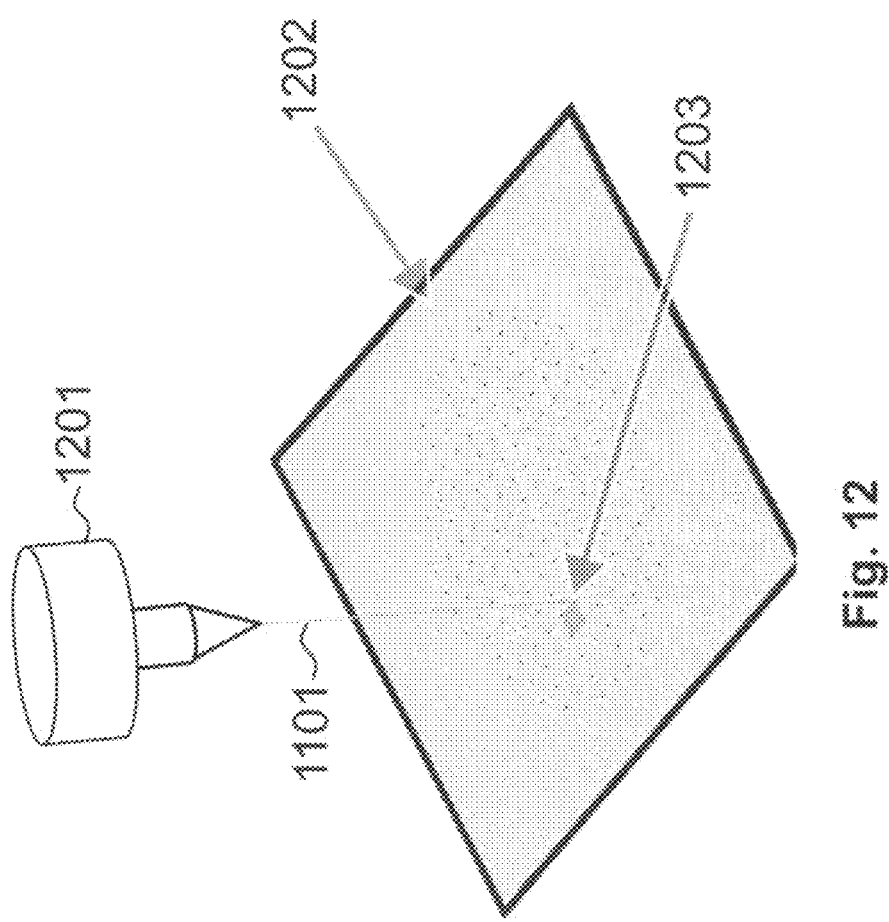
Figure 13:
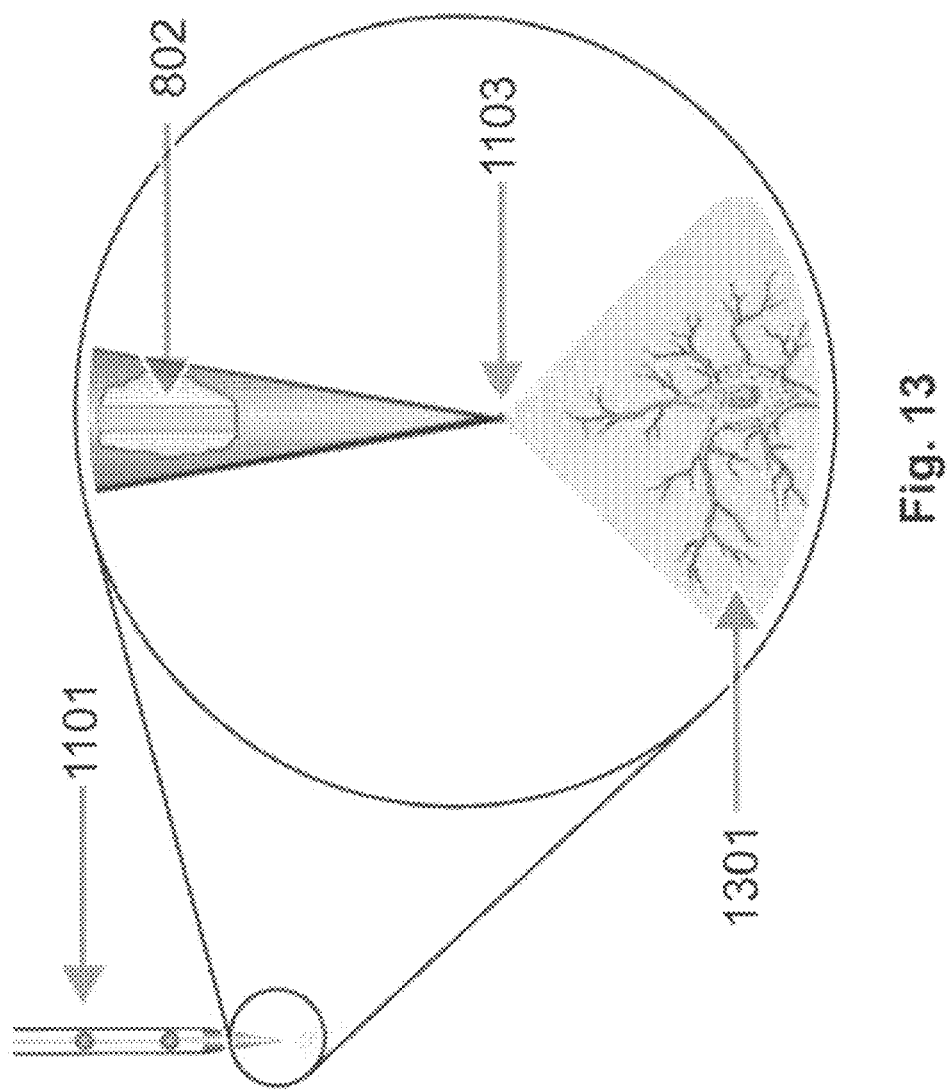
Figure 14:
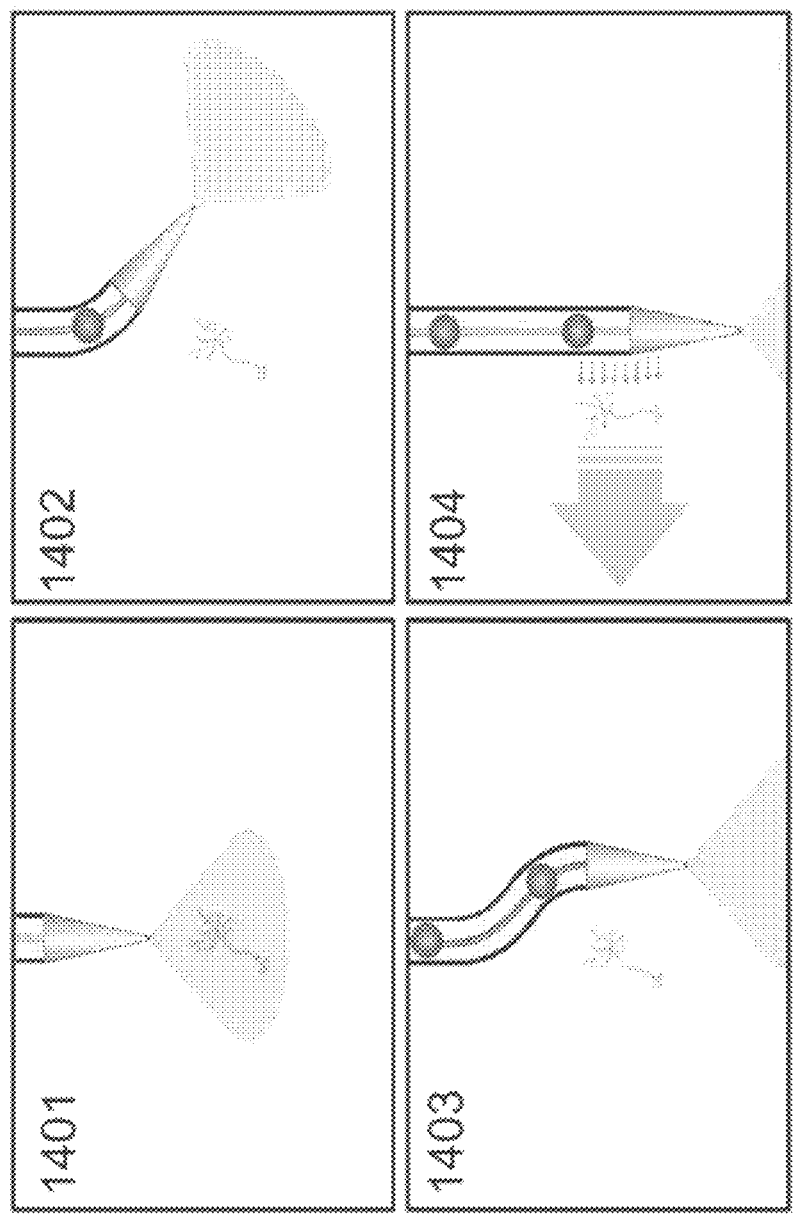
Figure 15:
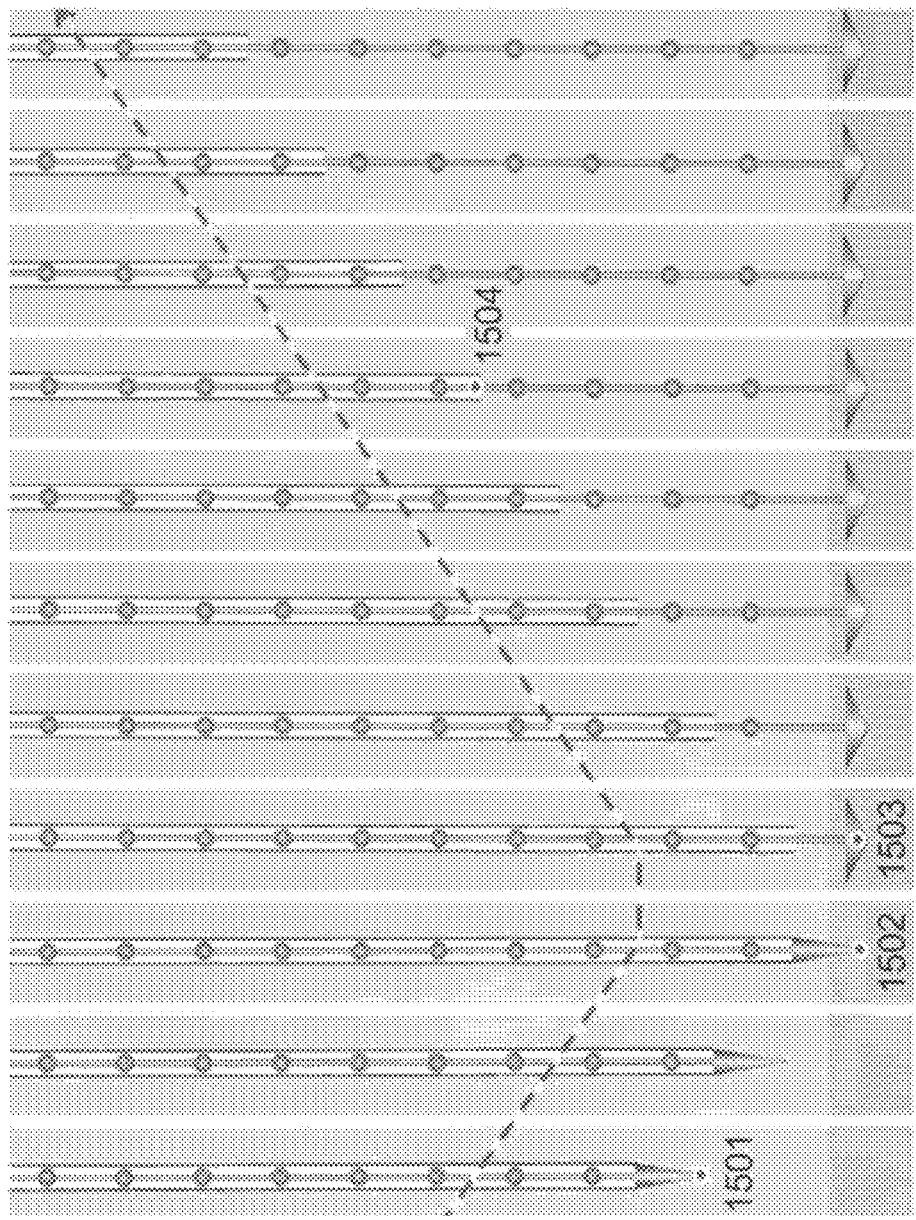
Figure 16:
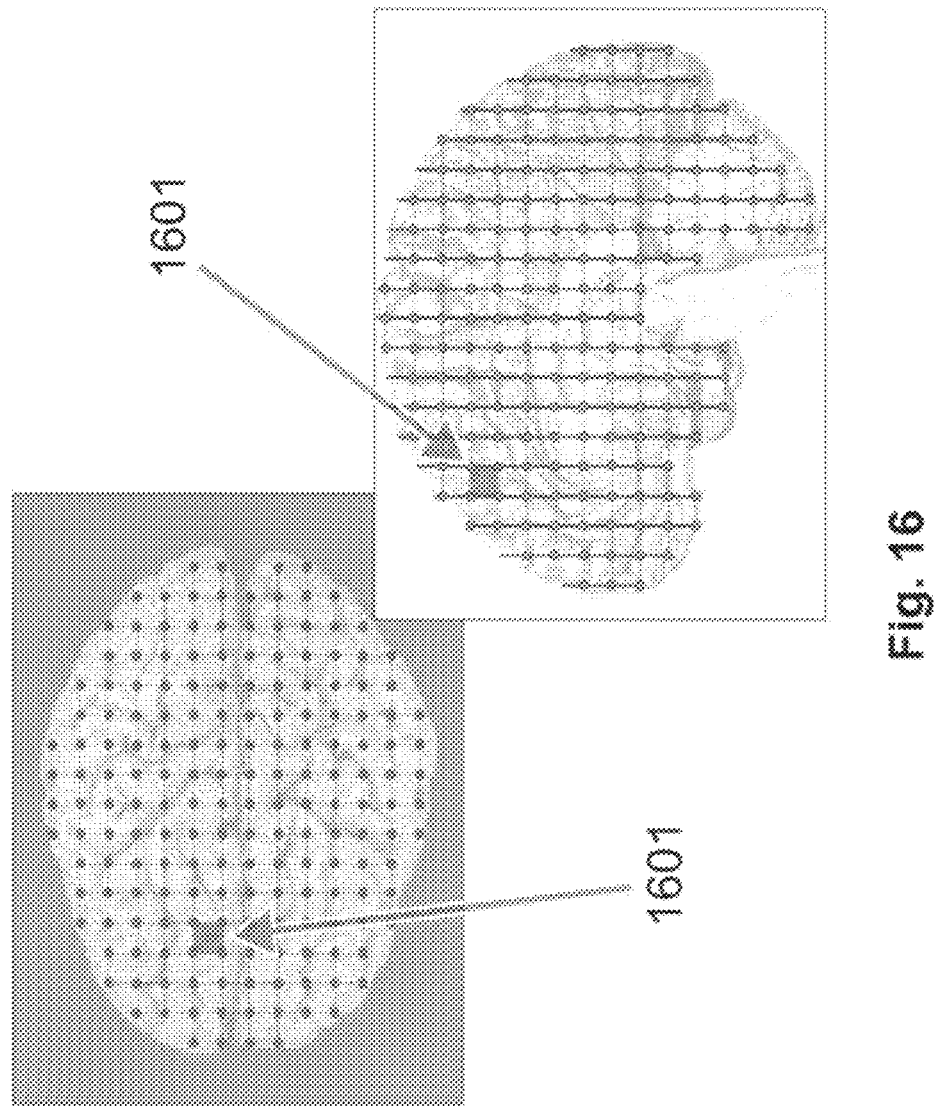
Figure 17:
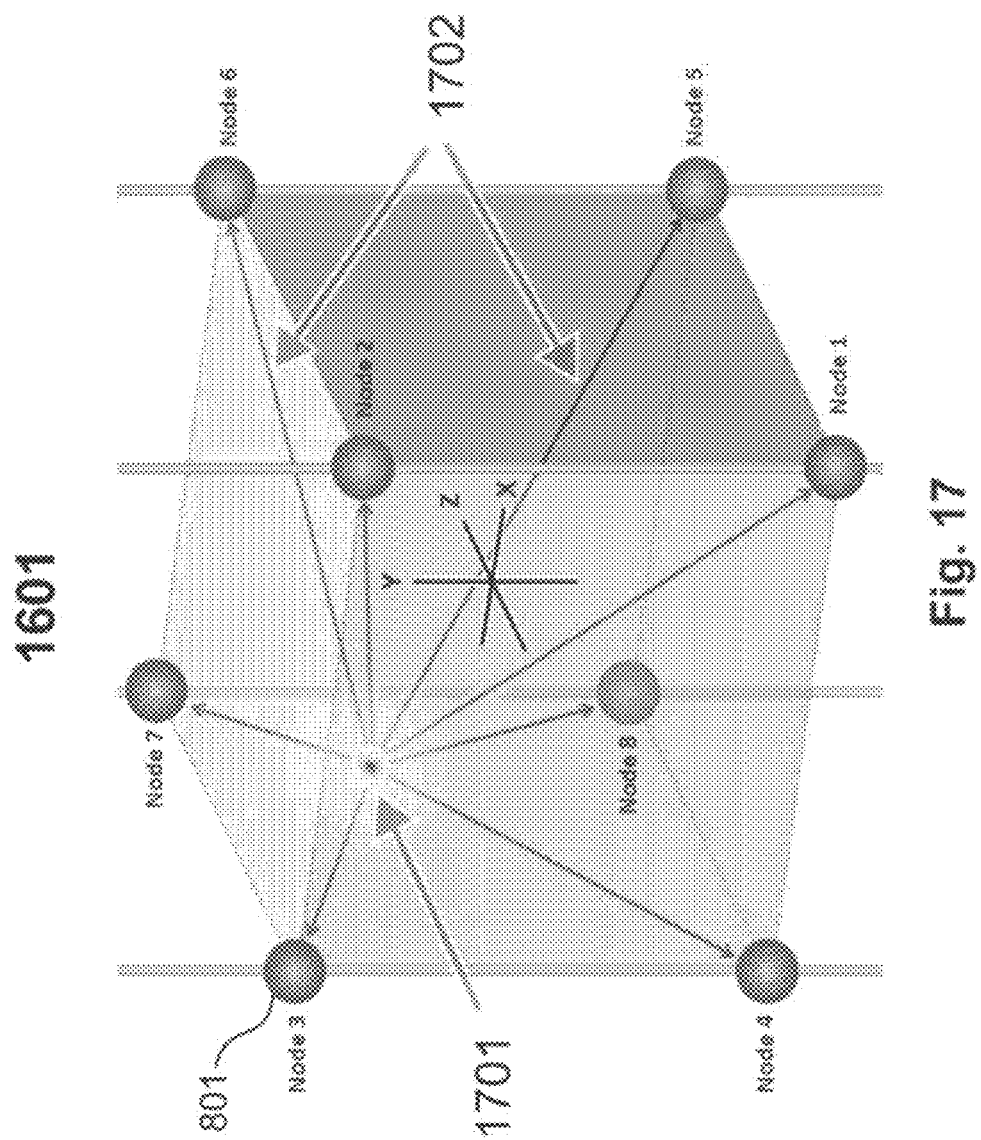
Figure 18:
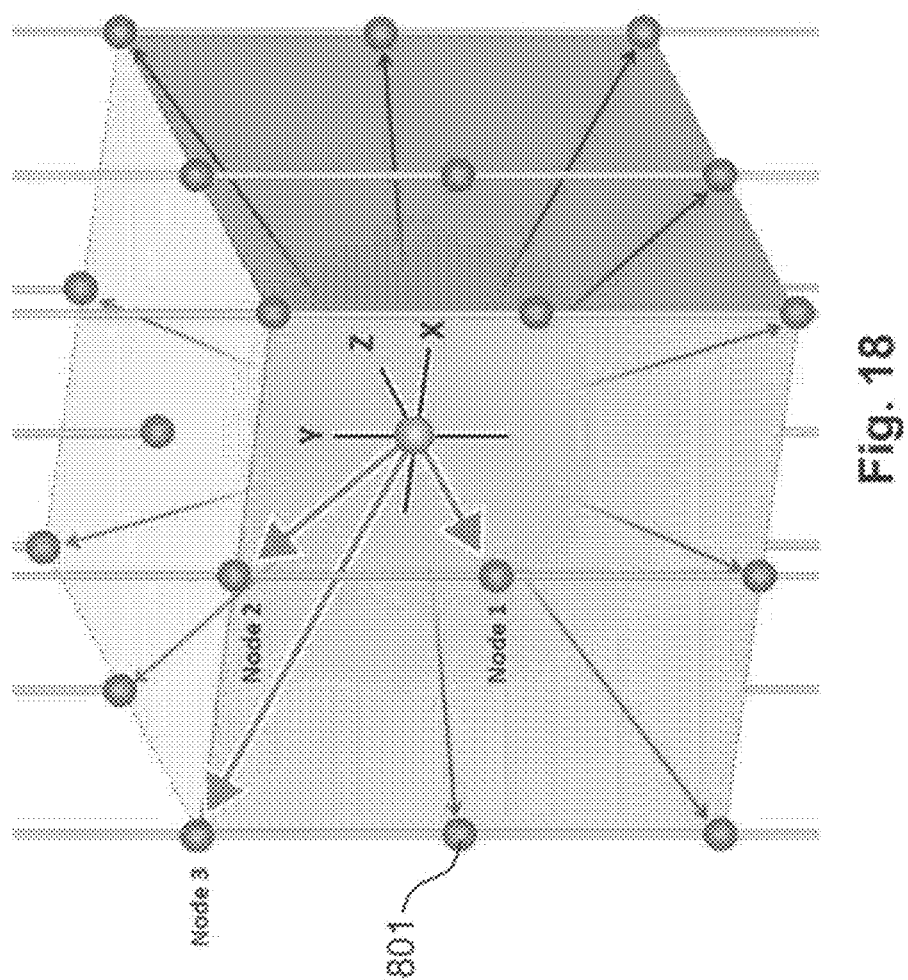
Figure 19:
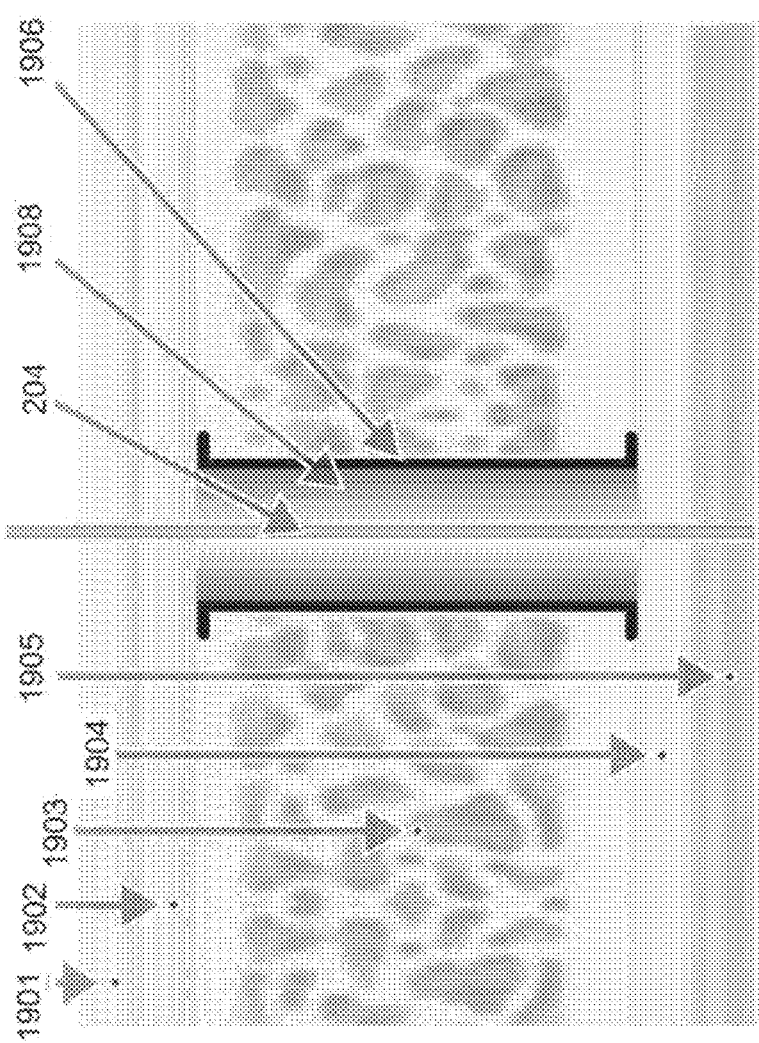
Figure 20:
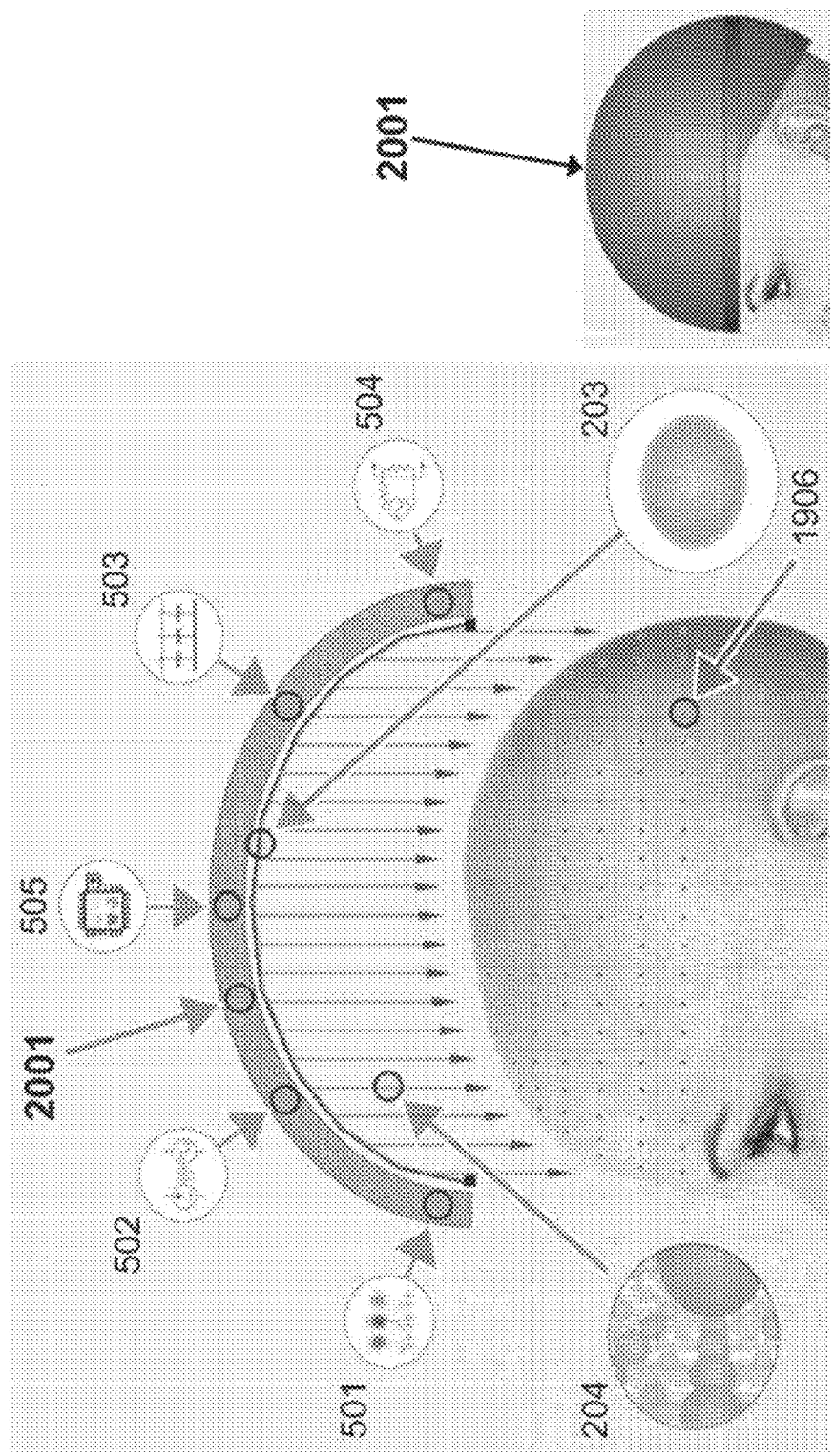
Figure 21:
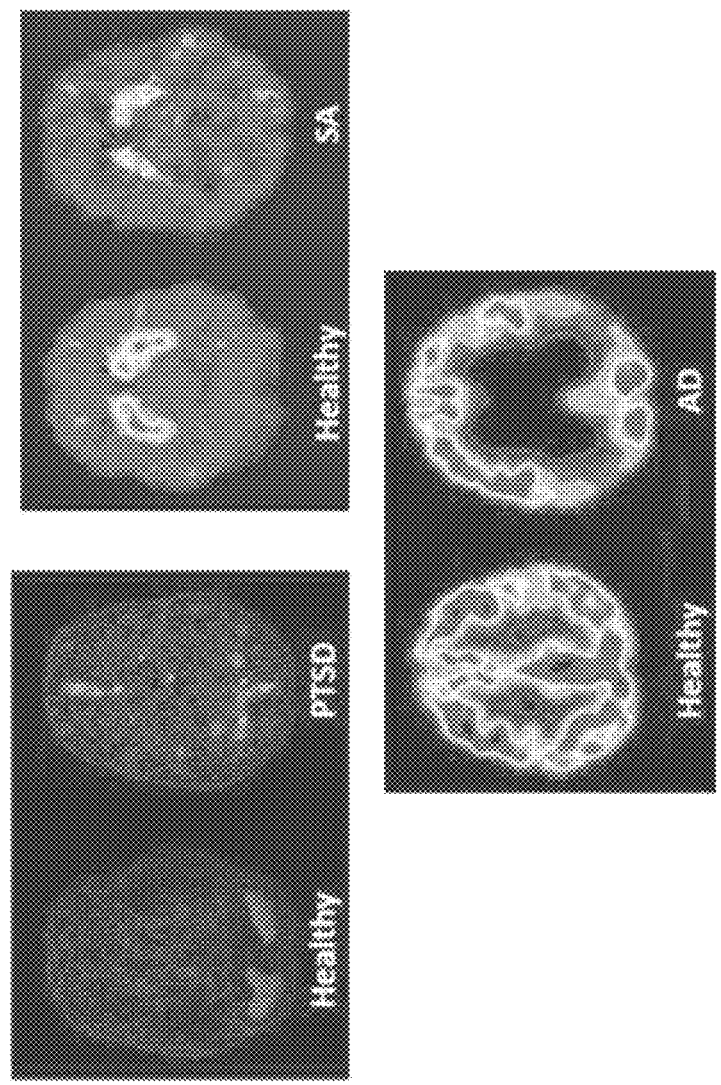
Figure 22:
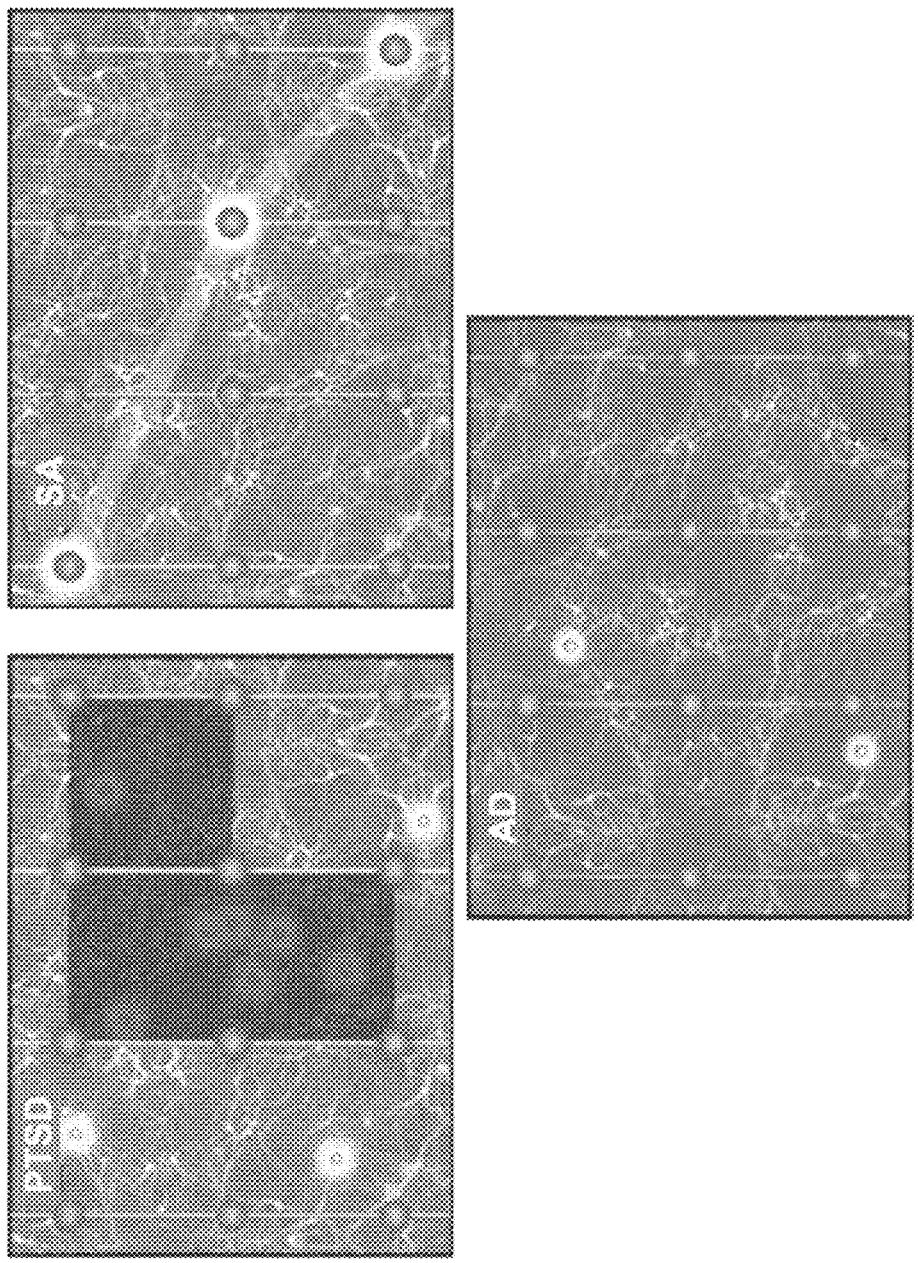
Figure 23:
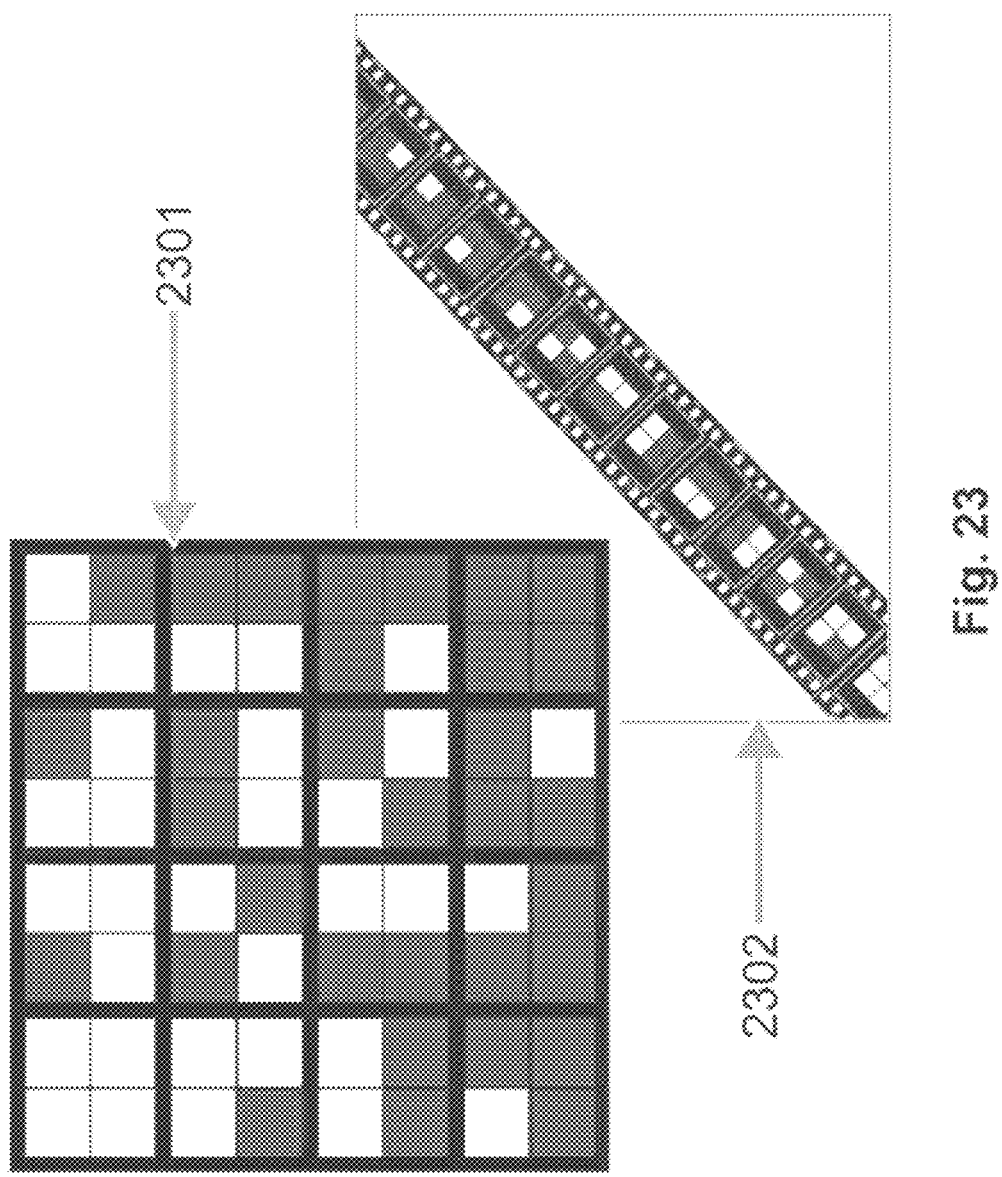
Figure 24:
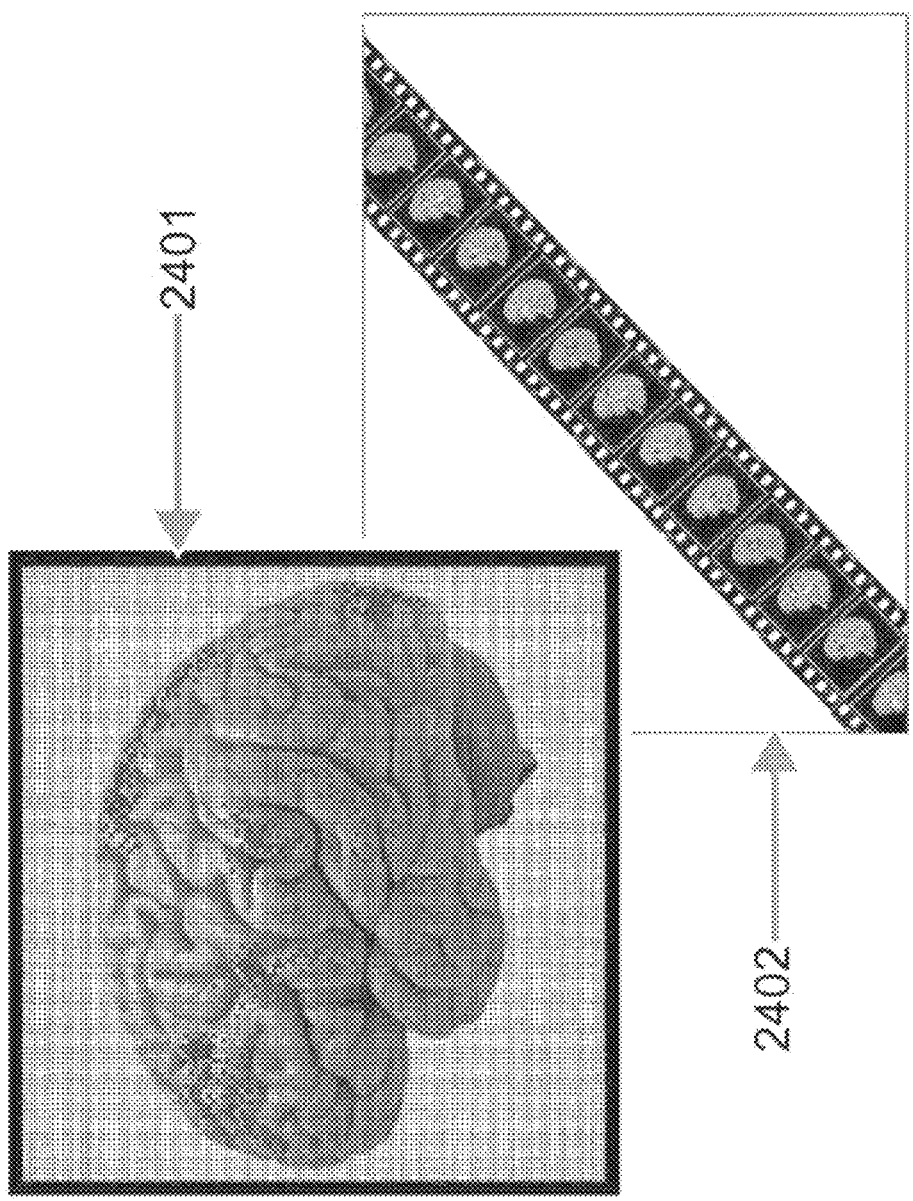
Figure 25:
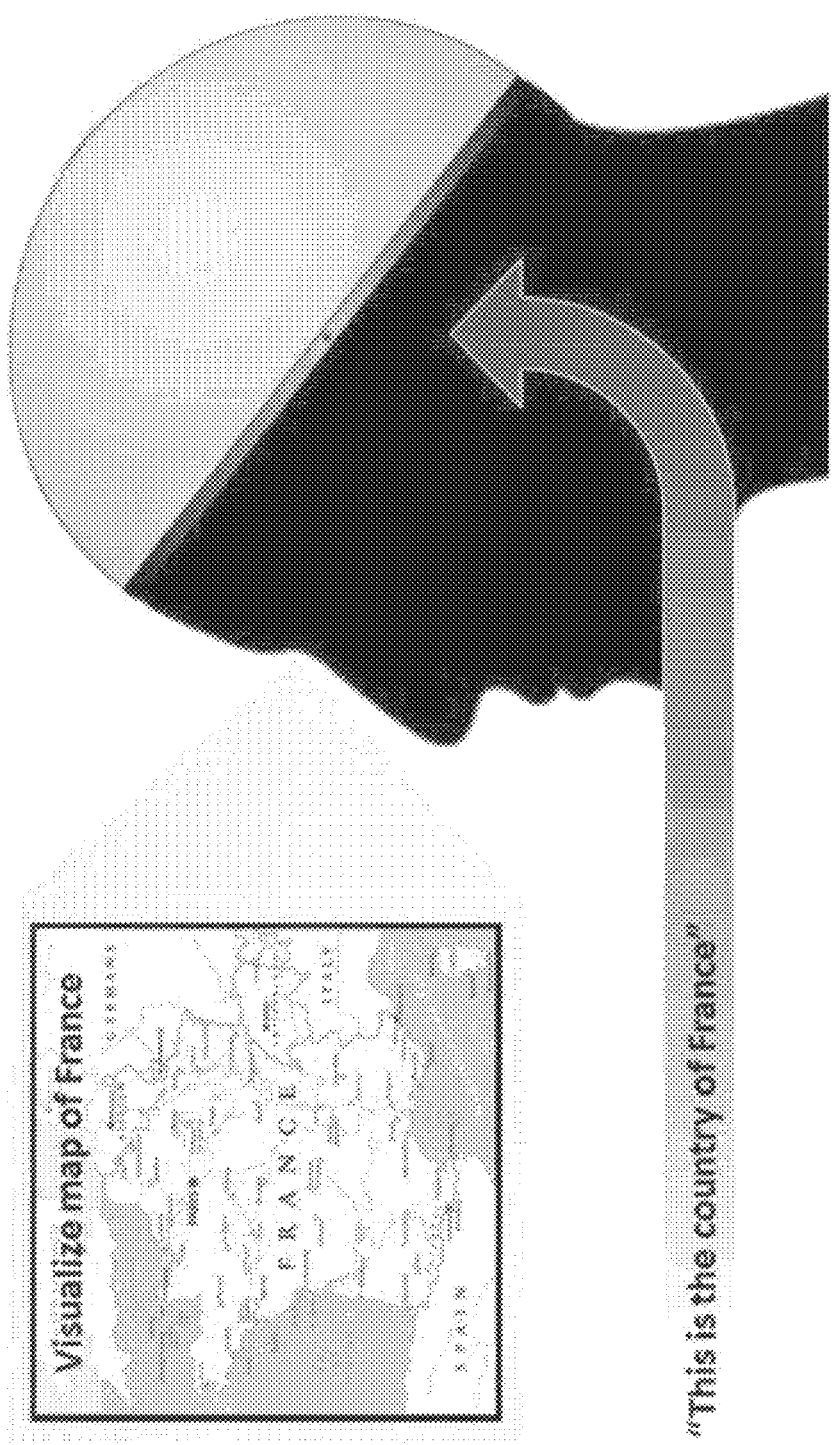
Figure 26:
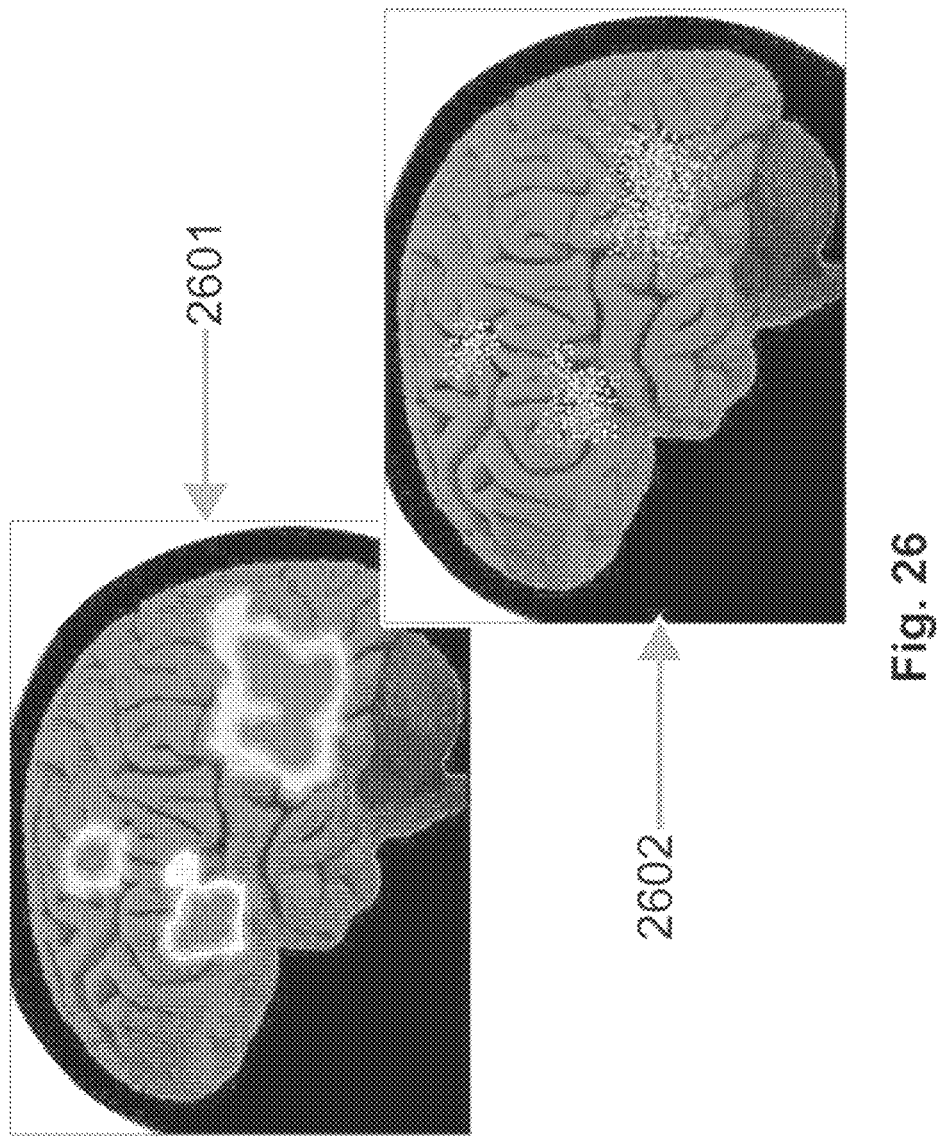
Figure 27:
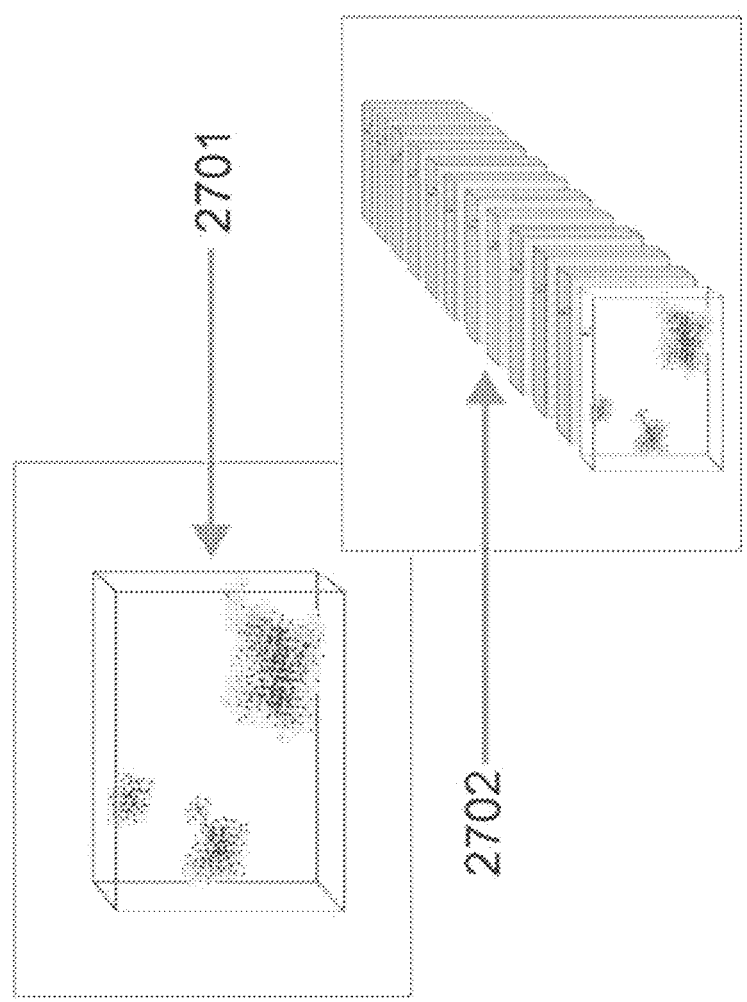
Figure 28:
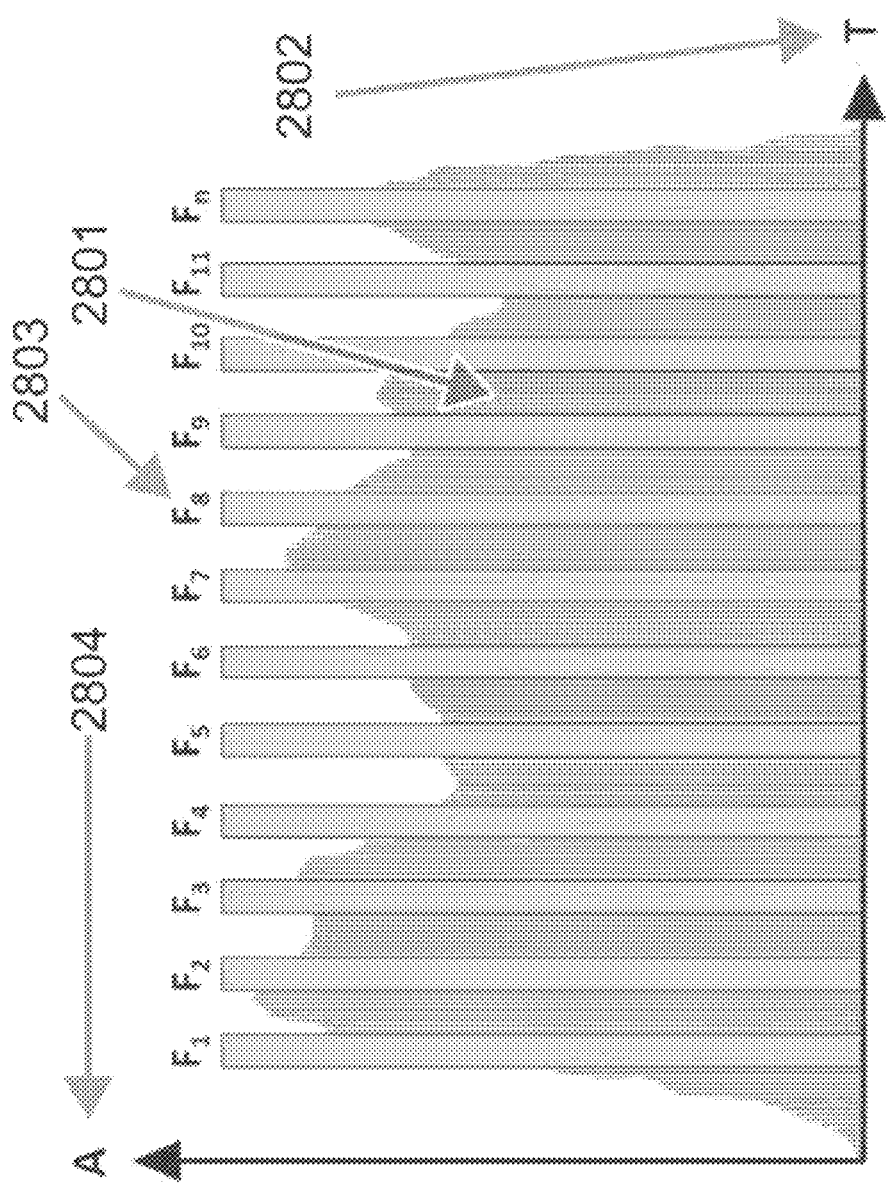
Figure 29:
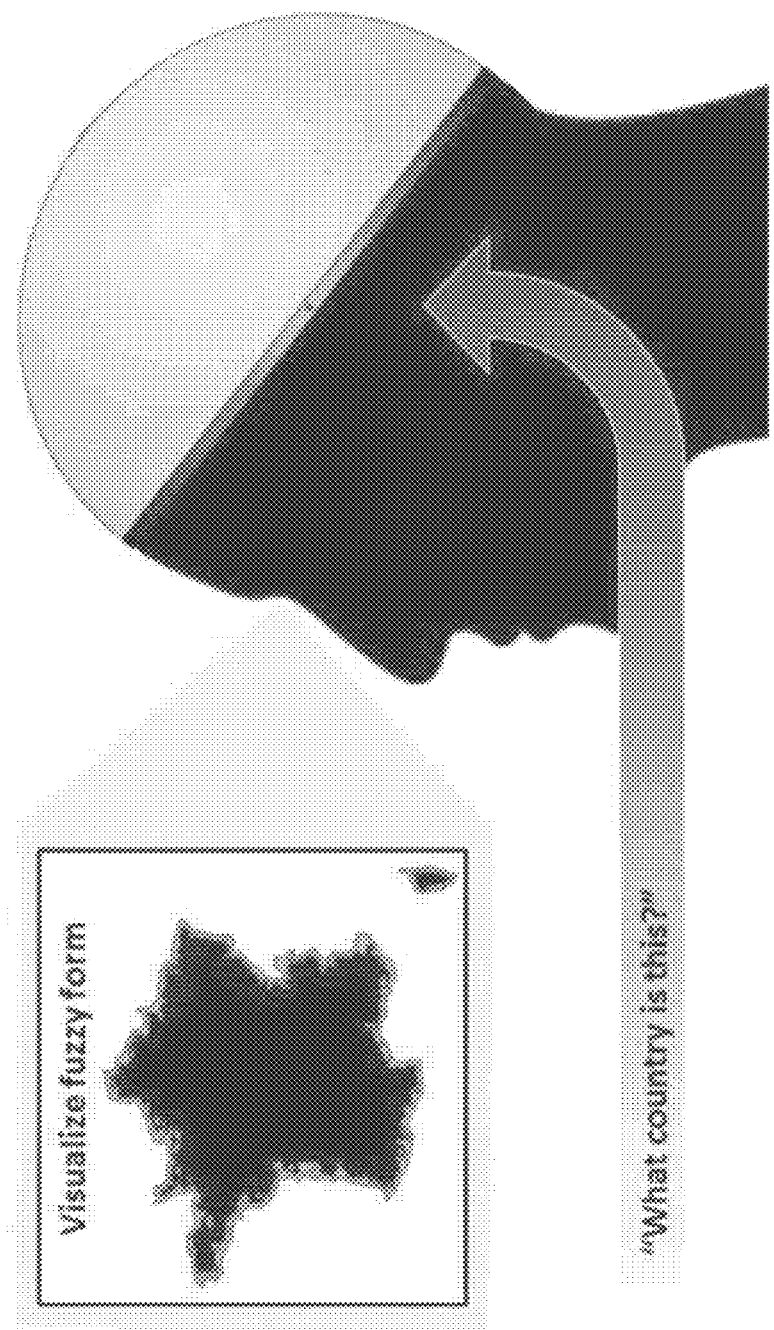
Figure 30:
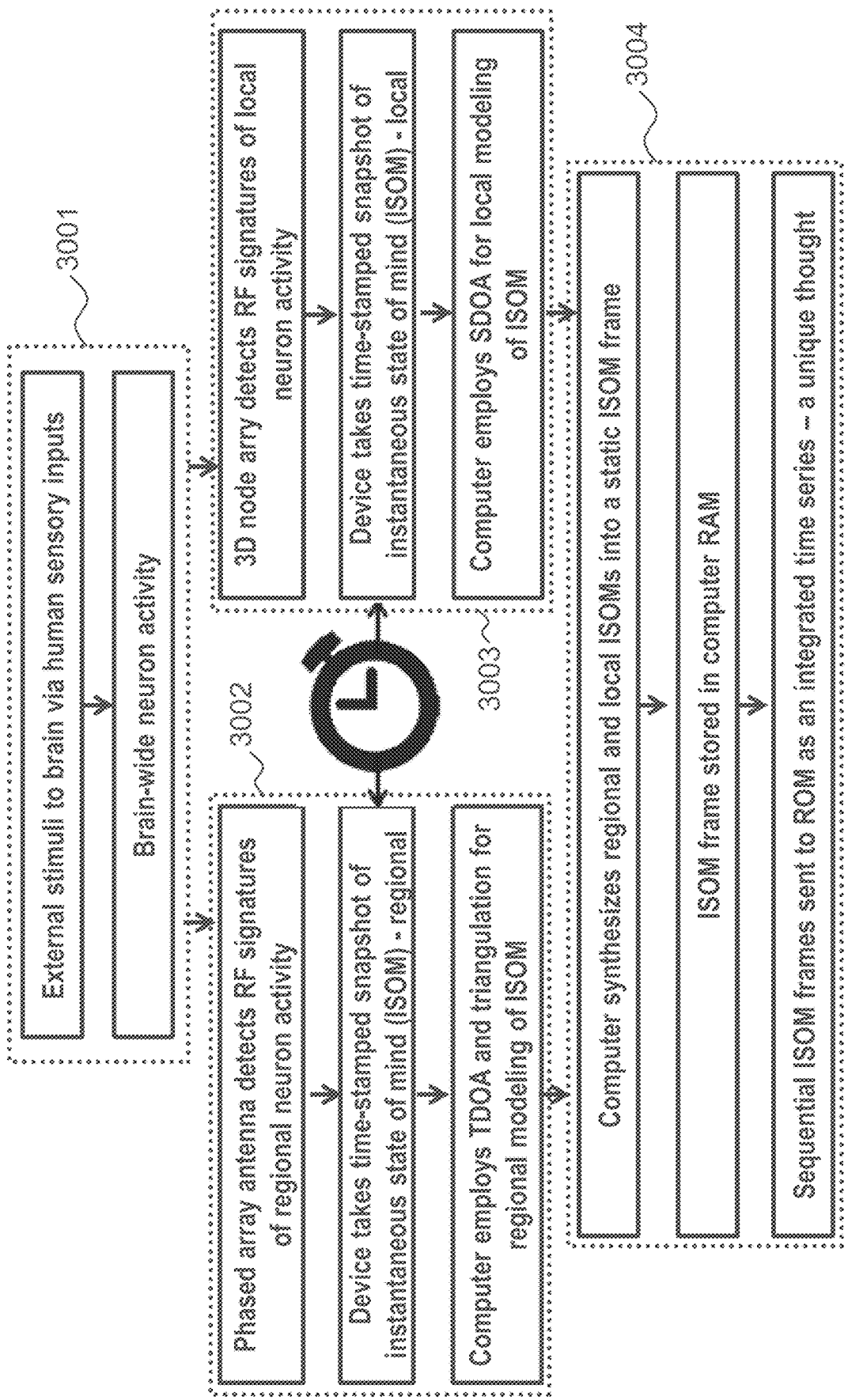
Figure 32A:
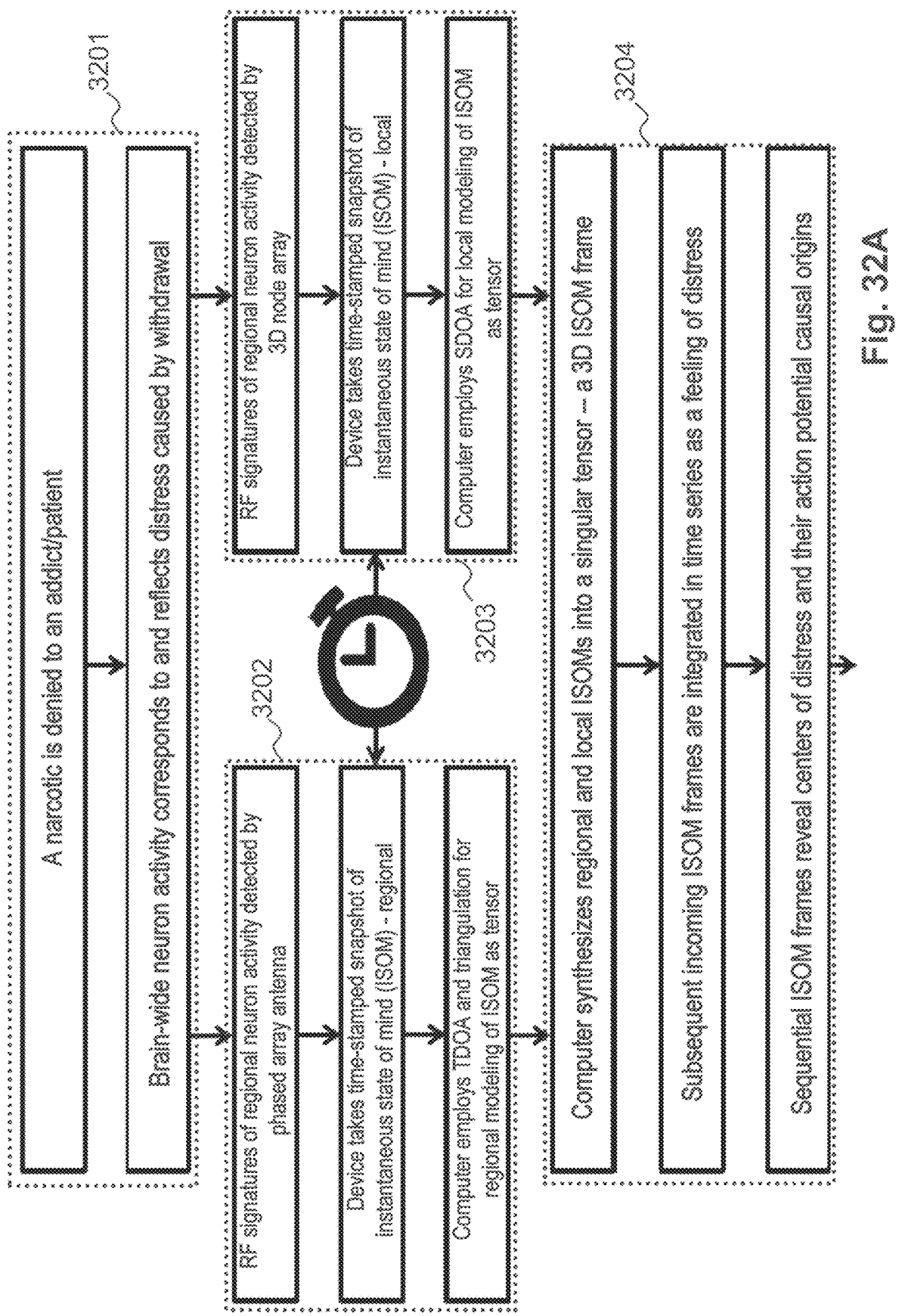
Figure 32B:
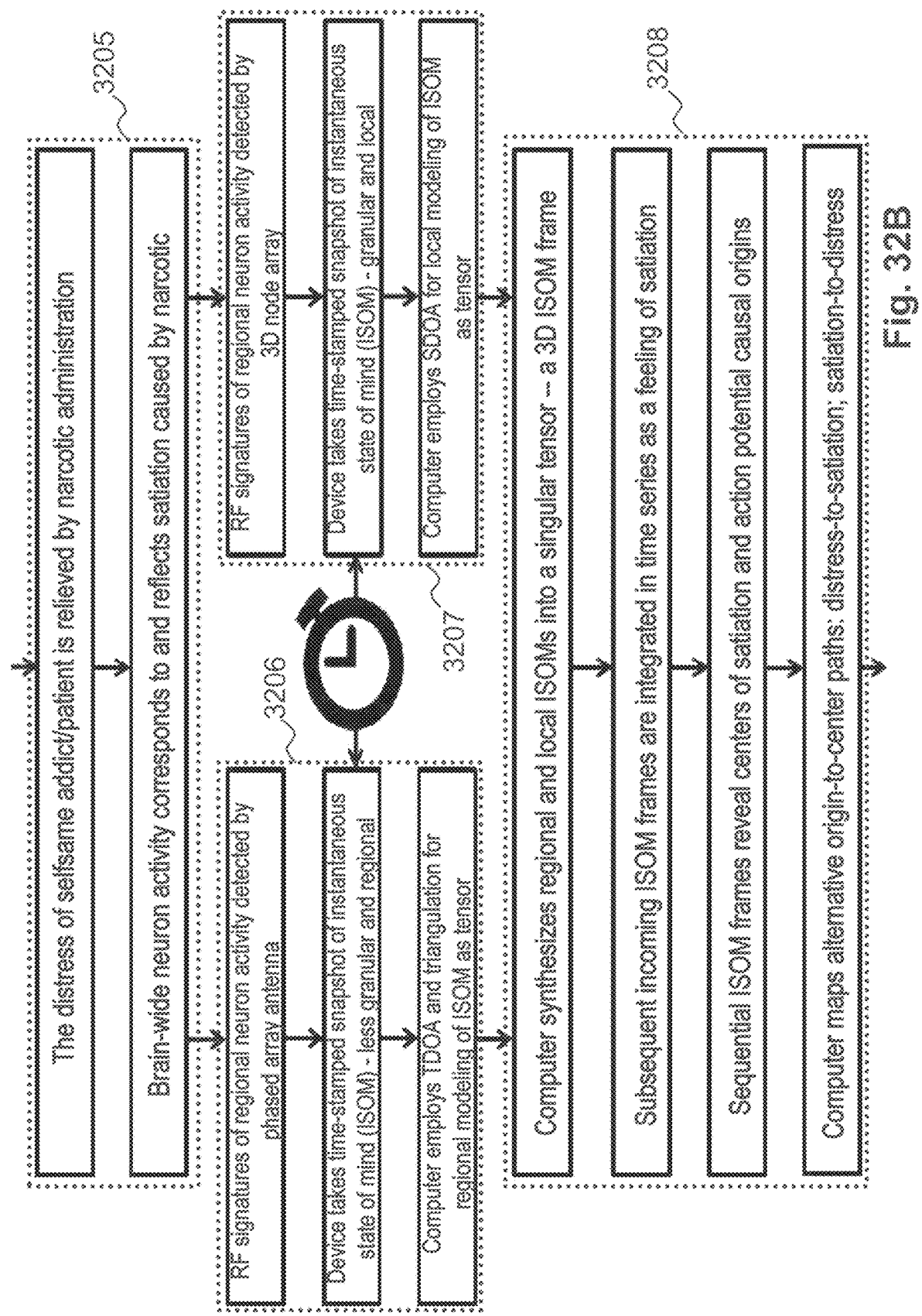
Figure 32C:
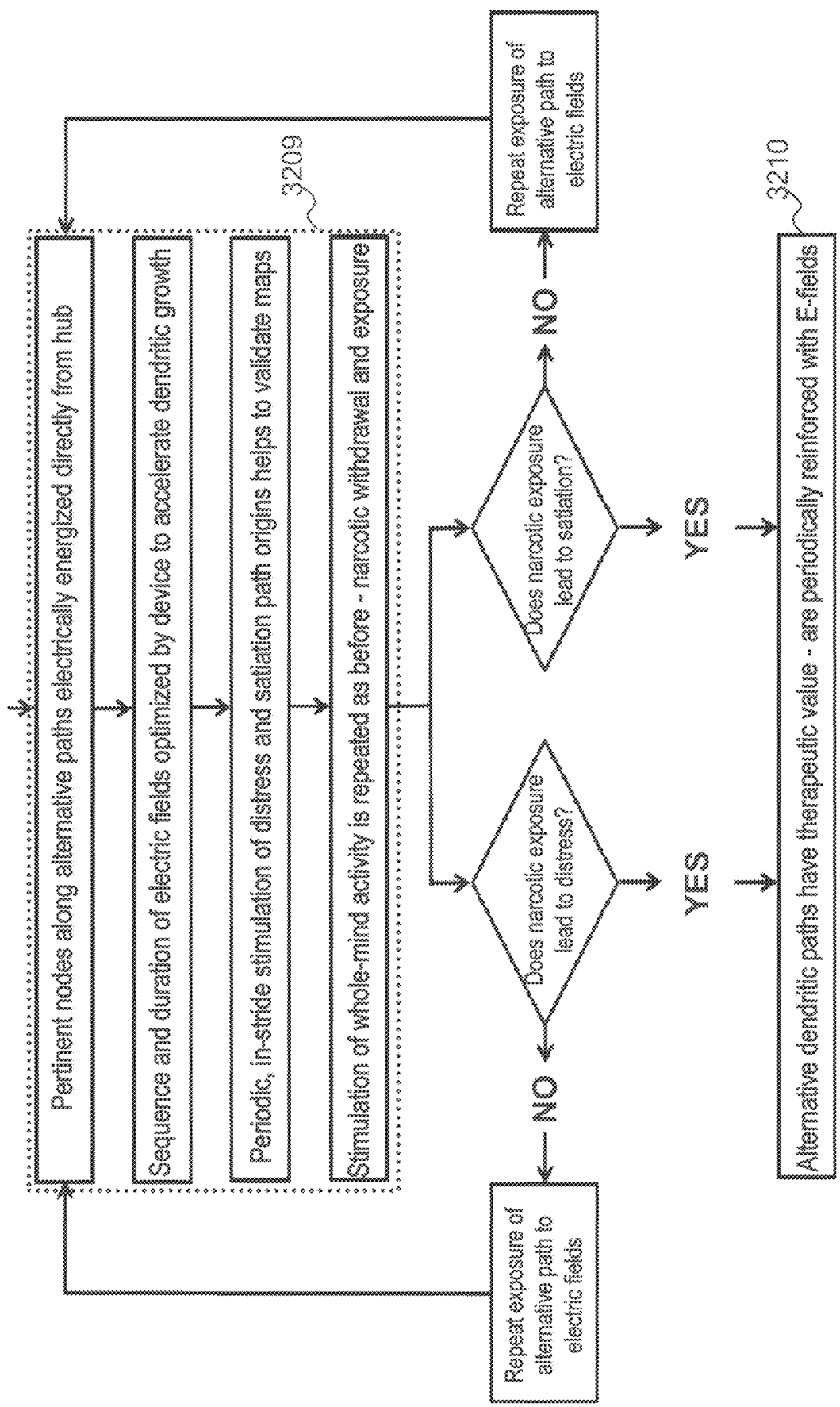
Figure 34:
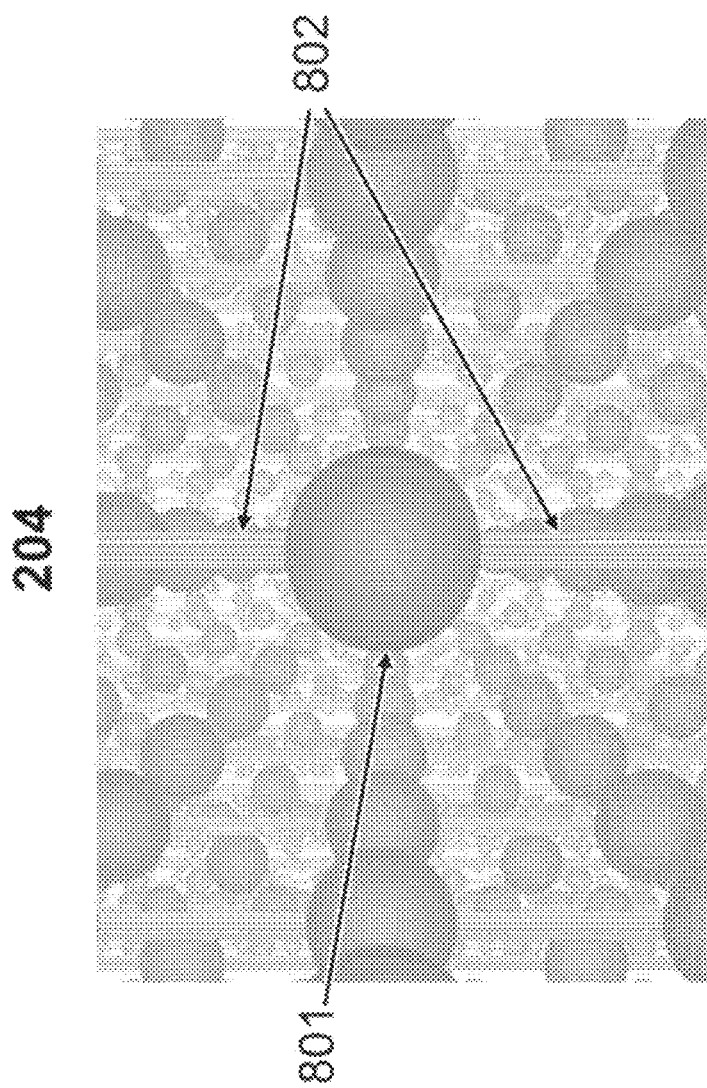
Figure 35:
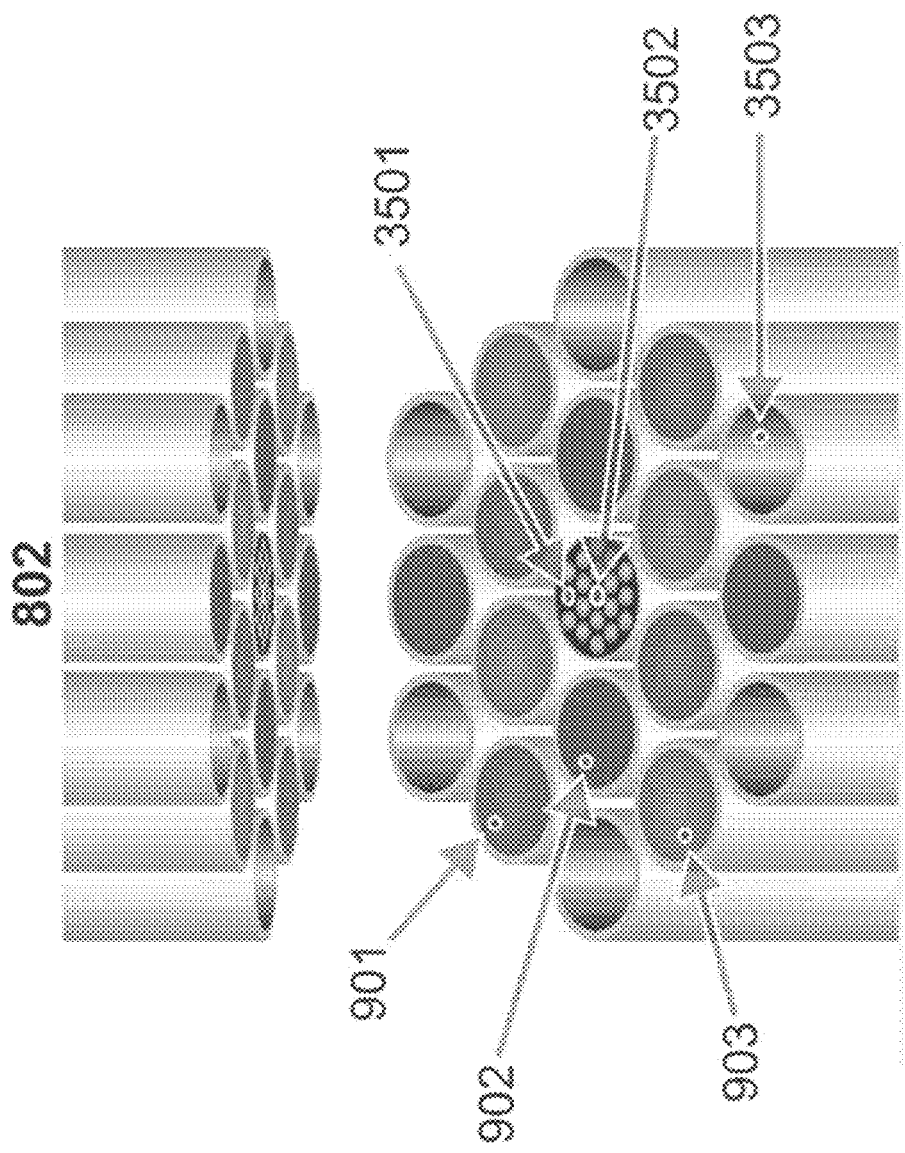
Figure 36:
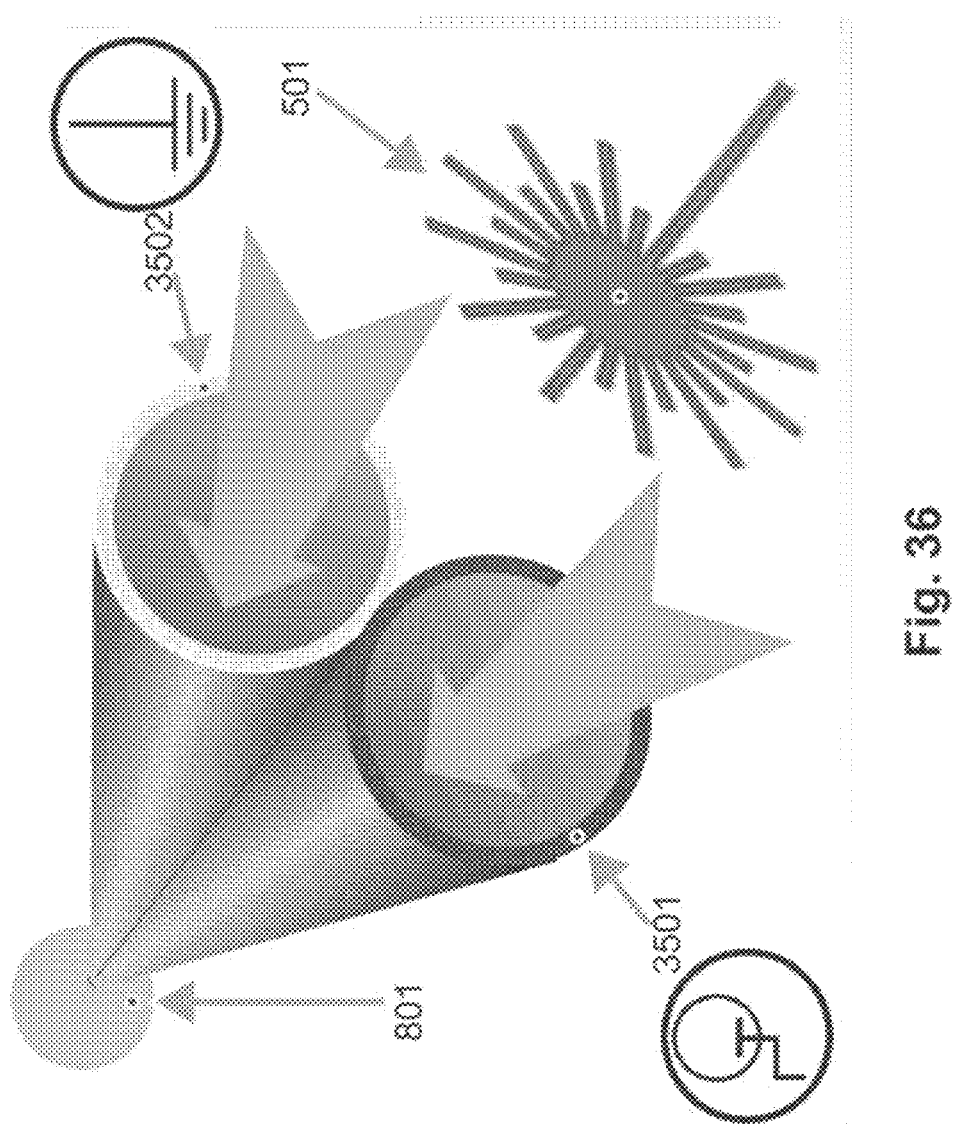
Figure 37:
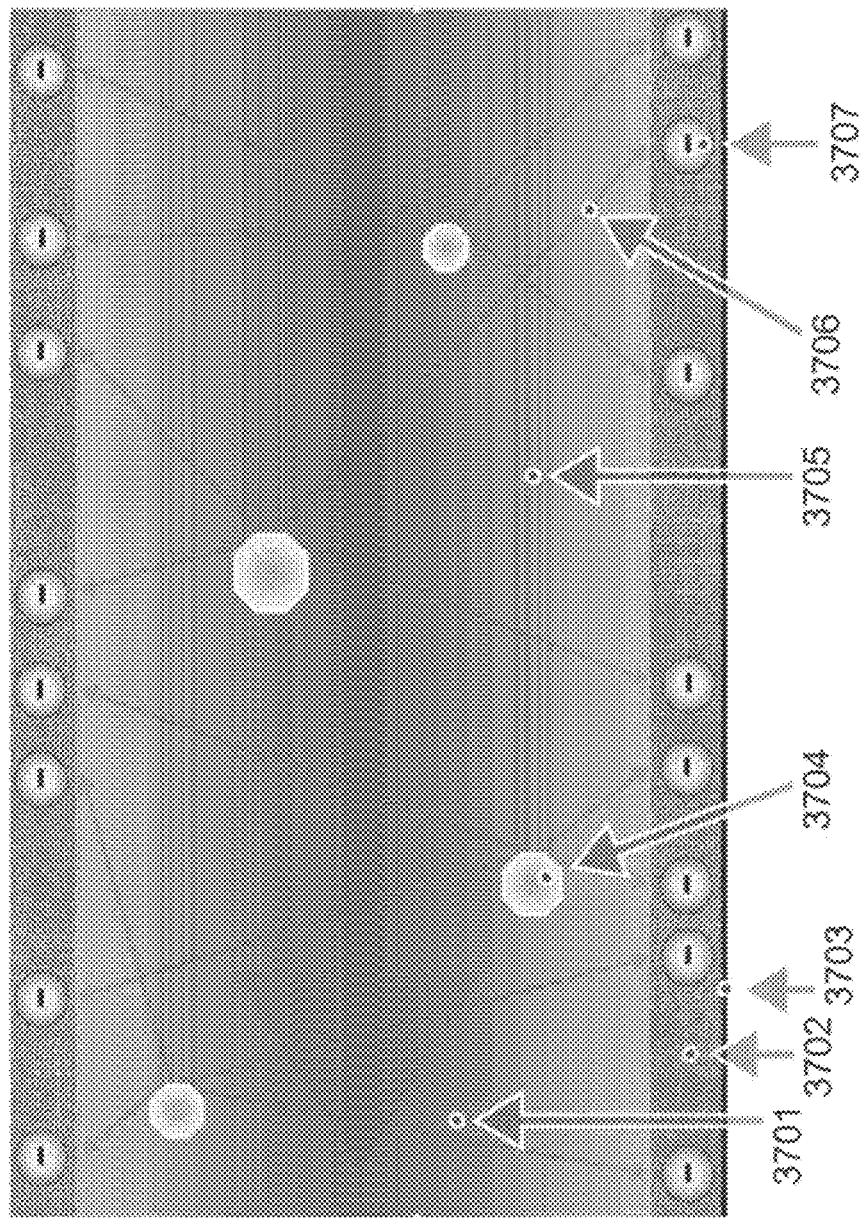
Figure 38:
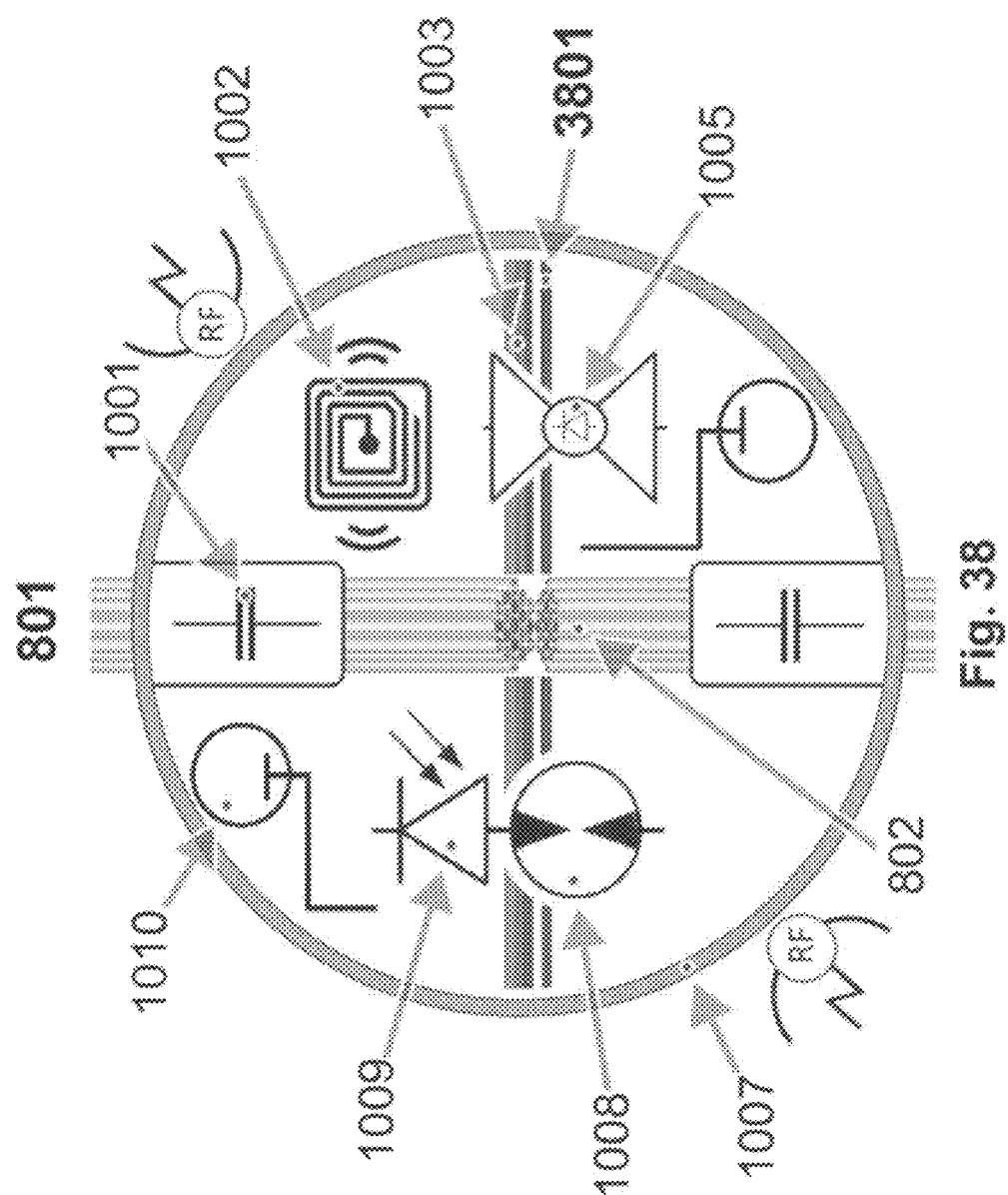
Figure 39:
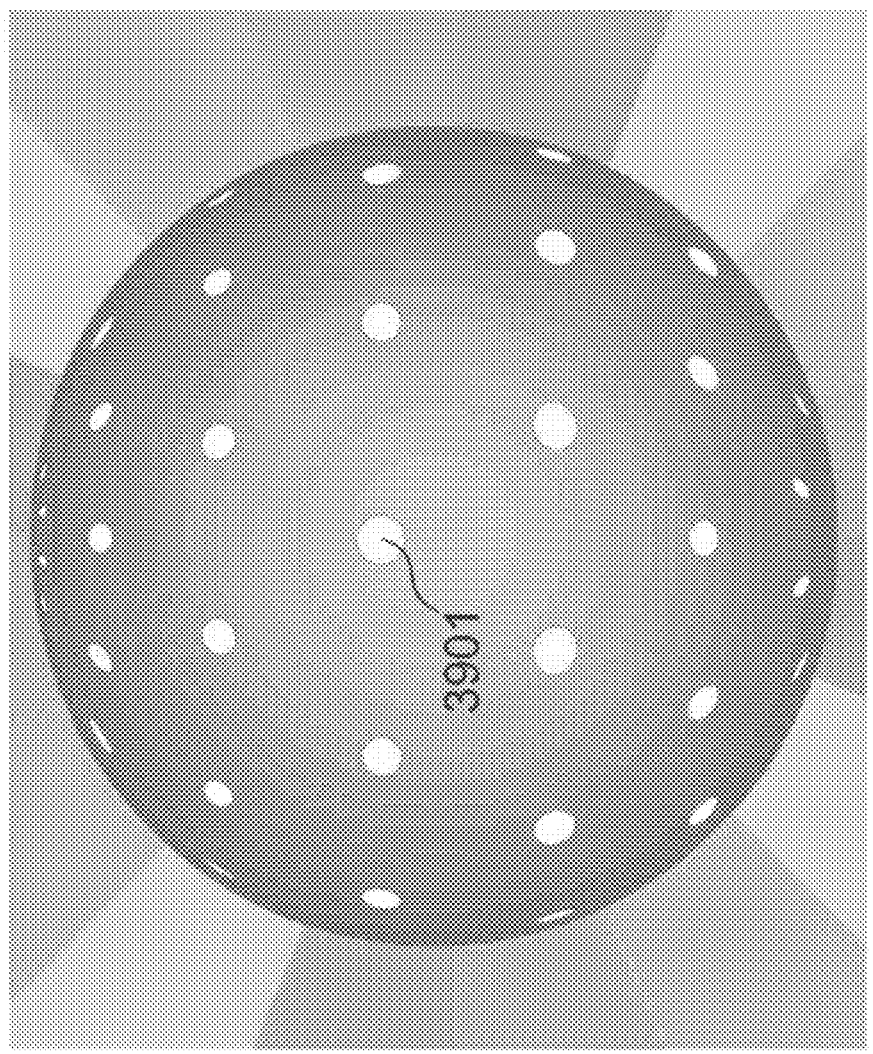

Exemplary FIG. 2 may show four components for human-machine cognitive synthesis according to an exemplary embodiment;

Exemplary FIG. 3 may show the implementation of an artificial cranial skull cap according to an exemplary embodiment;

Exemplary FIG. 4 may show an exemplary cranial skull cap replacement procedure;

Exemplary FIG. 5 may show a notional schematic diagram of the device components inside the artificial cranium skull cap according to an exemplary embodiment;

Exemplary FIG. 6 may show a notional configuration of the cognitive computer according to an exemplary embodiment;

Exemplary FIG. 7 may show a configuration of the conformal, phased array antenna according to an exemplary embodiment;

Exemplary FIG. 8 may show a three-Dimensional array of conductor-linked transceiver nodes according to an exemplary embodiment;

Exemplary FIG. 9 may show a cross-section view of the string of the three-dimensional array of conductor-linked transceiver nodes according to an exemplary embodiment;

Exemplary FIG. 10 may show a notional cross-section view of the node of the three-Dimensional array of conductor-linked transceiver nodes;

Exemplary FIG. 11 may show a configuration of insertion instrument for the three-Dimensional array of conductor-linked transceiver nodes;

Exemplary FIG. 12 may show an example of deep brain stimulation probe insertion;

Exemplary FIG. 13 may show a magnified view of the string insertion tube needle point as it approaches a neuron;

Exemplary FIG. 14 may show an example of the automated mitigation technique;

Exemplary FIG. 15 may show a procedure of piezo actuated needle tip expansion;

Exemplary FIG. 16 may show cubic space divisions throughout the brain;

Exemplary FIG. 17 may show the EM energy from the action potential measured among the eight nodes 801 of a cubic volume;

Exemplary FIG. 18 may show intermodal paths formed between a node 801 and the surrounding twenty-six nodes;

Exemplary FIG. 19 may show a cross-section view of the human cranium where micro-passages are drilled according to another exemplary embodiment;

Exemplary FIG. 20 may show the externally-worn device housing;

Exemplary FIG. 21 may show PET scans of healthy brains and brains suffering from PTSD, SA and AD;

Exemplary FIG. 22 may show notional working examples of the treatments for mental disorders;

Exemplary FIG. 23 may show the 2-dimensional model in which the states of mind is visualized as a 2D frame;

Exemplary FIG. 24 may show a 3-dimensional abstraction of the modeling;

Exemplary FIG. 25 may show a case of the question-answer scenario where a labeled map is observed, along with a verbal assertion that it is the country of France;

Exemplary FIG. 26 may show notional snapshots of neuron activities detected by the phased array antenna and the 3D node array;

Exemplary FIG. 27 may show the modeling of the human thought process as series of 3D snapshots;

Exemplary FIG. 28 may show a graph of neuron activities during duration of human thought;

Exemplary FIG. 29 may show the second phase of the question-answer scenario case;

Exemplary FIG. 30 is a flowchart illustrating a device recording procedure of a human thought;

Exemplary FIGS. 31A-D are flowcharts illustrating the human thought recording procedure applied to the question-answer scenario case;

Exemplary FIGS. 32A-C are flowcharts illustrating the human thought recording procedure applied to counter addictions;

Exemplary FIGS. 33A-D are flowcharts illustrating the human thought recording procedure applied to reenergize neurons for Alzheimer's disease;

Exemplary FIG. 34 may show a three-Dimensional array of semiconductor-linked transceiver nodes according to another exemplary embodiment;

Exemplary FIG. 35 may show a cross-section view of the string of the three-dimensional array of semiconductor-linked transceiver nodes according to another exemplary embodiment;

Exemplary FIG. 36 may show a three-dimensional perspective view looking down an individual 3D array spoke towards a single node along with semiconductor fibers;

Exemplary FIG. 37 may show a working mechanism of the semiconductor fibers;

Exemplary FIG. 38 may show a notional cross-section view of the node of the three-dimensional array of semiconductor-linked transceiver nodes;

Exemplary FIG. 39 may show micron-scale windows on the node surface; and

Exemplary FIG. 40 may show the self-embedding of the node according to another exemplary embodiment.

DETAILED DESCRIPTION OF THE EMBODIMENTS

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, the sequences of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

According to an exemplary embodiment, and referring to the Figures generally, a method and system for whole-mind cognitive interface may be disclosed. According to an exemplary embodiment, such a system may comprise a bodily-integrated artificial cranium, a computer, a RF antenna, and a transceiver array to seamlessly augment the human brain with artificial intelligence (AI) to permit enhanced cognitive functions and human host feedback-based neurological rewiring. Additionally, the system and method may lead to advancements in neuro medicine and genetic engineering that halt and reverse vexing diseases and disorders including, but not limited to: Post Traumatic Stress Disorder (PTSD); Substance Abuse and Addiction (SA); and Alzheimer's disease (AD).

Turning now to exemplary FIG. 2, FIG. 2 shows four components for human-machine cognitive synthesis. According to an exemplary embodiment, an artificial cranium skull cap 201 may replace an organic adult cranium and may mount and house device components 202 providing protection for the brain and device 202 and enabling routine physical access to the brain. Also, in an exemplary embodiment, the device components 202 may include computer, electrical, optical and radio frequency (RF) components nested within the artificial cranium skull cap 201. The device components 202 may act as a cognitive machine prosthesis for an adult human brain, record thoughts as 3D frame time series that model neuron spike events, and stimulate modeled thought by energizing brain points and regions of origin.

Referring still to FIG. 2, according to an exemplary embodiment, conformal, phased array antenna 203 may be nested on internal surface of the artificial cranium skull cap 201 and may be capable of receiving and transmitting RF energy. The conformal, phased array antenna 203 may spatially locate neuron events through triangulation as a receiver and project RF energy to stimulate neuron activity as a transmitter. Additionally, according to an exemplary embodiment, the three-dimensional array of conductor-linked transceiver nodes 204 may be capable of detecting natural RF, optical, or electrical fields and events and artificially generating RF, optical, or electrical fields and events while maintaining a continuous physical optical, electrical, RF, or other type of connection with a computer.

Turning now to exemplary FIG. 3, FIG. 3 shows the implementation of the artificial cranial skull cap 201. According to an exemplary embodiment, the cranial skull cap may be removed in order for the transceiver array and RF antenna 203 to have unimpeded access to the brain. Furthermore, removal of the cranium may present an opportunity to replace it with a detachable, artificial skull cap 201 that offers enhancements in itself: the replacement may provide superior protection, for both the brain and the machine interface device, against kinetic shock.

Turning now to exemplary FIG. 4, FIG. 4 shows an exemplary procedure of the cranial skull cap replacement. Following a scan of the natural cranium, the prosthesis may be printed via additive manufacturing using a variety of materials, including metals. According to an exemplary embodiment, the prosthetic cranium may be several times thicker than the average 0.25 inches of an adult male skull with volume to house critical device components. It may also be detachable for maintenance and upgrading purposes, as well as externally accessible for battery replacement, physical plug-in, and other purposes. According to an exemplary embodiment, the organic scalp and hair functionality may be maintained by the reconnection of natural flaps, thus preserving the natural appearance of the device-augmented human.

Turning now to exemplary FIG. 5, FIG. 5 shows a notional schematic diagram of the device components 202 inside the artificial cranium skull cap 201. According to an exemplary embodiment, the device components 202, including the computer and electrical, optical & radio frequency (RF) components, may be housed in the artificial cranium 201. The device components 202 inside the artificial cranium skull cap 201 may serve as the hub of all brain-immersed transceiver nodes 204 by means of conductor/connector spokes. Specifically, the device components 202 may include, as sub-components, optical sources and detectors 501, AC and DC electrical power 502, capacitor bank 503, RF source 504 and cognitive computer 505. According to an exemplary embodiment, the optical sources and detectors 501 may generate and detect various wavelengths and waveforms, and lasers may be employed for light-sensitive diode switch operation, optical frequency identification (OFID) of 3D array nodes 204, brain region density characterization, direct neuron stimulation and other purposes. Also, in an exemplary embodiment, AC and DC electrical power 502 may supply and maintain the power condition, and may additionally include batteries, an external power option, a DC-AC inversion option, voltage variability, and waveform options. Further, the capacitor bank 503 may perform spark gap operations and artificial action potential generations, and the RF source 504 may generate variable wavelengths with phase shift capabilities for beam and hot-spot steering.

Turning now to exemplary FIG. 6, a notional configuration of the cognitive computer 505 may be described. According to an exemplary embodiment, the cognitive computer 505 with statistical tools and network interface may serve as the intelligent "hub" of the hub and spoke device architecture. According to an exemplary embodiment, the cognitive computer 505 may include functions 601: Cognitive computing, capable of unstructured natural language, image, video, sparse and fuzzy data processing, using neuromorphic architectures, and cognitive assistance to the augmented human—physically analogous to an adjunct brain region; 602: Deep learning enabled by artificial and convolutional neural networks (ANN and CNN); 603: Statistical tools that permit cognitive functions that may include, but are not limited to, linear and non-linear regression modeling for predictive analytics, and forecasting and alerts to the human host; 604: On-board structured and pre-processed data repository for optional off-the-net access to data corpora with periodic network refresh; and 605: Network Interface Card (NIC) for optional wireless and wired linkage to networks and other NIC-equipped devices.

Turning now to exemplary FIG. 7, which shows a configuration of the conformal, phased array antenna 203. According to an exemplary embodiment, the conformal, phased array antenna 203 is the device layer adjacent the dura and closest to the brain—mated to the artificial cranium 201 from below. The RF source 504 for the phased array 203 may be housed in the cranium shell 201. According to an exemplary embodiment, the RF array 203 may detect and locate regional neuron activity and may stimulate and artificially replay recorded regional activity. Reference numbers depict: 701: Cross-section view of the conformal, phased array antenna aperture elements 203; 702: A natural neuron action potential; 703: The detectable RF electromagnetic (EM) energy emitted from the spike event; 704: RF signal triangulation by >3 aperture elements; and, alternatively, precise artificial stimulation of neurons by >3 aperture elements for activity replay; and 705: Phased array antenna mated with artificial cranium—seen from below. Specifically, the utility of the phased array antenna 203 may rely on two properties of a neuron, in that the neuron functions as an organic transceiver as described above.

Figure 1:
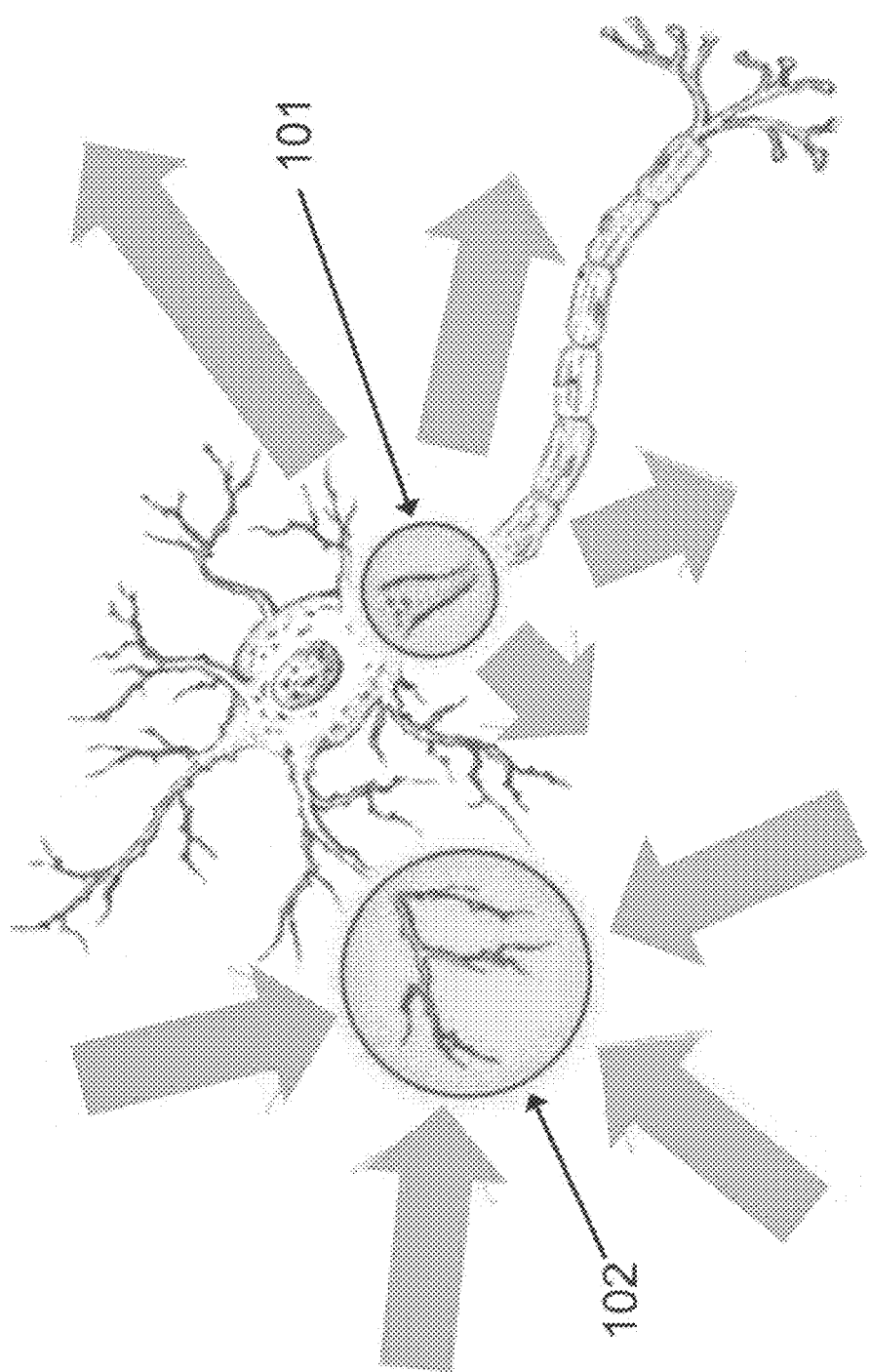

Referring back to exemplary FIG. 1 together with FIG. 7: first, in a transmission mode, the neuron emits an RF signal from the Axon Hillock 101 during an action potential spike event. Such a RF emission may be localized by the triangulation capabilities of the array 704, revealing regional neuron activity for device synthesis with more granular observations of individual action potentials by the 3D array 204. Second, in a receiver mode, the dendritic trees 102 of neurons on specific regions may harvest EM energy from targeted emissions by the phased array 203. Such antenna emissions may, by cascading chains of action potentials, trigger neuron activity in the precise locations where specific thoughts are known initiate.

Turning now to exemplary FIG. 8, the three-dimensional array of conductor-linked transceiver nodes 204 may be described. (FIG. 8 depicts a notional array of node strings—the actual volume occupied by the nodes and edges is not drawn to scale; artistic illustration only). According to an exemplary embodiment, the 3D array 204 may include multiple strings of spherical transceiver nodes 801; the edges are the bundles of connectors/conductors (strings) 802 that bind them together. Also, in an exemplary embodiment, individual strings 802 may extend vertically, deep into the brain, to serve as transceiver "spokes" of the hub (the main components 202 including the cognitive computer 505 inside the artificial cranium cap 201) and spoke interface device architecture. Assuming that the 3D array accounts for the average volume of the human brain, the 3D array would encompass 1,260 $cm^3$; with nodes 801 located at the corners of each cubic centimeter, the 3D array would require about 1,800 nodes. According to an exemplary embodiment, nodes 801 may be distributed at one-centimeter intervals along these spokes, and the exact number and length of spokes may be tailored to the specific brain topology of the human host. The nodes 801 of the 3D array 204 may form a grid-structured cubic space division in 3D topology that segments the whole-brain volume into 1 cm cubes. Also, in an exemplary embodiment, the diameter of prototype nodes 801 may be 1.5 mm, with the diameter of connector/conductor bundle edges (802: strings) at 200 microns. About 1,800 nodes array may model individual neuron activities as approximations of thought and replay the approximated thoughts through deep brain stimulation. The 3D grid-structured topology of the whole-mind interface device may enable neuron activity at any instance to be modeled as a multi-dimensional tensor. With an intracranial cubic space division, wherein one node is located at each grid structure intersection, the spatial relationships between nodes can be accurately determined. Therefore, if brain-wide neuron states at any instant are taken to be binary—all neurons spatially detected are either firing or not firing—then all local instantaneous neuron activity can be recorded in three-dimensions with high granularity. The tensor that mathematically models the gridded brain may use the Cartesian Coordinate System. However, the alternative use of Cylindrical, Spherical or other Coordinate Systems may also be possible.

Turning now to exemplary FIG. 9, a cross-sectional view of the string 802 of the three-Dimensional array of conductor-linked transceiver nodes 204 may be described. In accordance of an exemplary embodiment, reference numbers may depict: 901: Shorter wavelength visible laser fiber—the transmissivity of the fiber may be optimized to allow the passage of UV wavelengths, with overlap into visible violet; 902: Medium wavelength visible laser fiber—the transmissivity may be optimized to allow the passage of visible spectrum, overlapping with near IR and UV; 903: Longer wavelength visible through IR laser fiber—the transmissivity of the fiber may be optimized to allow the passage of IR, with overlap into visible red; 904: Electrical conductors for AC, DC and tailored waveforms—sufficient fiber optic paths may be included to ensure termination at individual nodes 801, and in cases where the number of spoke nodes 801 exceeds the number of fibers, such that there is not a dedicated fiber for each node 801, OIFD may be employed to target specific nodes 801; and 905: Hollow conduit for liquid, gas, or other brain access—any bundle of conductors may contain unused paths for unplanned future access.

Turning now to exemplary FIG. 10, FIG. 10 illustrates a notional cross-sectional view of the node 801 of the three-Dimensional array of conductor-linked transceiver nodes 204. In accordance with an exemplary embodiment, reference numbers may depict: 1001: Local capacitor charge storage, which may be a redundant option in light of the primary capacitor storage (503: the capacitor bank) located within the cranially-housed hub (the main components 202 including the cognitive computer 505 inside the artificial cranium cap 201); 1002: Radio and/or Optical Frequency Identification (RFID and/or OFID)—RFID may permit addressing and locating individual node 801 via phased array 203 triangulation, and OFID may permit precise addressing of specific nodes 801 for specific actions; 1003: Optical fiber laser light distribution—the uses for coherent light may include, but are not limited to, coherent light stimulation of local neurons and spark gab activation via the photo diode switch 1009 for the local spark gap RF emission powered by the hub (the main components 202 including the cognitive computer 505 inside the artificial cranium cap 201) or local capacitor discharges in the node 801; 1004: Electrical conductors for AC, DC and tailored waveforms—as the node-specific termination points, these electrodes may have multiple purposes including, but not limited to, continuous inter-node E-field generation for dendrite growth and local biological neuron spike stimulation; 1005: Ambient RF energy harvesting rectenna for local capacitor recharge—primary capacitor storage (503: the capacitor bank) may be at the cranially-housed hub (the main components 202 including the cognitive computer 505 inside the artificial cranium cap 201); 802 (strings): Fiber optic (901, 902 and 903), electrical conductor 904 and hollow conduit 905 access bundle—the diameter of these prototype edges (802: strings) may be 200 microns, and they may pass through and connect 1.5 mm nodes 801; 1007: Conductive shell for RF transceiver and electrical field generation—conductive node shell 1007 may be capable of transmitting RF signatures from spark gap events and generating artificial action potential; it may be also suited for detecting RF energy from local organic neuron action potentials, and it may serve as a spherical extension of the node-integrated electrode for E-field generation; 1008: Spark gap for in-situ/local artificial action potential generation—with charge storage at the cranium-housed capacitor bank 503, once triggered, the spark gap may generate an artificial action potential locally; 1009: Photodiode for optically-triggered spark gap discharge operation—controlled by the hub-located computer 505, the switching of the photodiode may cause the precise production of local artificial action potential spikes; and 1010: Electrode for shell-charging and local field generation (DC or AC)—this may serve as the terminal point for hub-originating electrical sources, and in contact with the node shell 1007, it may enable spherically symmetrical E-fields, or distribute charge for other functions.

Turning now to exemplary FIG. 11, a configuration of the insertion instrument for the three-Dimensional array of conductor-linked transceiver nodes may be described. In accordance with an exemplary embodiment, reference numbers may depict: 1101: a thin, hollow tube of hypodermic needle—the needle gauge (outside diameter) accommodates the ease of internal passage of the node string for string insertion; 802 (strings): Connector/conductor bundle string containing fiber optic (901, 902 and 903), electrical 904, and other conduits 905—prototype diameter of approximately 200 microns; 801 (nodes): 3D array transceiver node—prototype diameter of 1.5 mm; 1102: String insertion tube needle point; 1103: Fiber laser path illuminator and light intensity detector; and 1104: Piezo actuated needle tip expansion—when the tip 1102 arrives at the desired string anchoring depth, it may flatten but remain affixed to the node string.

Turning now to exemplary FIG. 12, FIG. 12 shows an example of deep brain stimulation probe insertion. According to an exemplary embodiment, a node string insertion device 1201 may use standard technologies used for deep brain stimulation probe insertion, and a template 1202 may be employed to maintain the geometric integrity of the array during the insertion of multiple node strings 204, either individually or simultaneously. Also, in an exemplary embodiment, a depiction of the grid template 1202 may guide the strict vertical insertion of probes through holes 1203 arranged at the corners of one centimeter squares. Additional options may also exist to insert several—or all—probes simultaneously in a single set of mechanical movements.

Turning now to exemplary FIG. 13, FIG. 13 shows a magnified view as the string insertion tube needle point 1102 approaches a neuron. The needle-tipped hollow tube 1101 could cause damage to neurons in its path if done blindly. The major signature of a neuron 1301 can be its reflectivity due to its higher relative density. According to an exemplary embodiment, the bundle of conduits that connects the nodes 801 in a spoke string 802 will include several fiber optic strands. At the tip of the needle 1102, one of the fiber optic strands could be dedicated to path illumination, while another could be dedicated to light signal detection (1103: the fiber laser path illuminator and light intensity detector). If the intensity of the reflected light increases greatly over a short distance, one may conclude that a neuron nucleus lies immediately ahead. This knowledge may lead to the automated mitigation technique that is described in the next figure.

Turning now to exemplary FIG. 14, an example of the automated mitigation technique may be described. According to an exemplary embodiment, the string insertion tube needle point 1102 may be comprised of thin cylinders of radially-poled piezoelectric material, which is used in scanning probe microscopes with piezoelectric tube scanners (1103: Fiber laser path illuminator and light intensity detector) and other applications. In an exemplary embodiment, the penetrating tips 1102 of each insertion probe 1101 could be designed to accomplish four neuron nucleus avoidance actions automatically: 1401: the illuminating fiber laser and detector 1103 at the tip of the insertion probe 1102 may alert the computer 505 that a neuron nucleus is potentially within its path; 1402: voltage may be automatically applied to an electrode, and the actuator wall may expand, causing vertical contraction and lateral deflection of tube tip 1102; 1403: the illuminator/detector 1103 may inform computer 505 of obstacle avoidance, and voltage may be automatically applied, causing a corrective deflection of the tube tip 1102, such that the tube tip's axis is aligned with its desired direction; and 1404: the probe may straighten along its original axis and gently push aside the neuron, so that the rigid probe resumes its downward progress on its original path.

Turning now to exemplary FIG. 15, FIG. 15 shows a procedure in which the piezo-actuated needle tip 1102 flattens upon arrival at the desired string anchoring depth while remaining affixed to the node string. These strings 802 of nodes 801 are described as being suspended vertically below the artificial cranium, forming what are described as spokes in a hub and spoke architecture, with the computer as the hub (the main components 202 including the cognitive computer 505 inside the artificial cranium cap 201). In accordance with an exemplary embodiment, reference numbers may depict: 1501: the hollow, large-gauge hypo-cranial insertion tube 1101 may proceed down a machine-guided vertical path through a template 1202; 1502: the tip of tube 1102 may reach terminal point, which is determined by either the geometry of the 3D array or the tip reaching the base of the natural skull; 1503: on command, the piezo-actuated needle tip 1104 may expand, acting as the resistance anchor for the node string 204 to which it remains affixed; and 1504: with the node string spoke anchored, the insertion tube 1101 is vertically withdrawn, leaving the taut yet flexible spoke and node string 204 in place. According to an exemplary embodiment, subsequent withdrawal of the rigid insertion tube 1101 is preferred to minimize biological brain displacement. The dimensions of the nodes and array considered for a prototype array are limited by current technology, but they can be substantially reduced in the future. Alternatively, as technology advances, the insertion tube 1101 could become an integrated, rigid-exterior "sheath" of the node string spoke 204 and remain anchored in place following deep brain insertion. This may require the insertion tube 1101, node 801 and connector 802 to have reduced diameters and corresponding volumes in order to minimize tissue displacement while also providing advantages for array stability and removal and/or replacement procedures. An unsheathed prototype array composed of a grid structure of perhaps 2,000 nodes would require approximately 20 meters of connector strings and would displace approximately 7 ml of brain tissue, which is conceivably tolerable for an intact cranium. A prototype employing sheathed spokes will displace up to 63 ml, which would require the expansion space provided by the artificial cranium; however, future array component miniaturization may permit sheathing of 2,000,000 nodes in a closed, natural cranium. Finally, the 3D spoke array is principally aimed at capturing instantaneous neuron activity throughout the biological brain, requiring node distribution throughout the entire brain. As an alternative to the principal objective, the 3D array can be designed/scaled back to capture specific brain regions of interest in an early prototype.

Turning now to exemplary FIG. 16, FIG. 16 shows cubic space divisions throughout the brain. According to an exemplary embodiment, once the multiple strings of nodes 204 that constitute the 3D array spokes are anchored, the entire node array 204 may be surveyed in place. During the first phase of the survey, RFID and OIFD node responses (1002: Radio and Optical Frequency Identification) may provide the precise locations and addresses of each node 801 to the computer model in three-dimensional space formats. In an exemplary embodiment, distortions of the physical array revealed in the survey may be corrected in the computer model by linearly transforming and translating node locations by comparing measured coordinates with the computer model. In FIG. 16, the node array 204 in which the cubic space division throughout the brain is in centimeter scale (seen from above and the side). The exemplary FIG. 16 shows approximated locations of the cubic space 1601, which may be in the same centimeter scale volume from both perspectives. According to an exemplary embodiment, once physical distortions of the array revealed in the survey have been corrected in the computer model, a precise characterization of the radio frequency (RF) transmissivity of the brain volume may be performed.

Turning now to exemplary FIG. 17, EM energy from an action potential measured among the eight nodes 801 of a cubic volume 1601 may be described. Time-difference-of-arrival (TDOA) of RF received at different nodes in the 3D array 204 may be ineffective in precisely locating neuron action potential events because the distances of EM energy travel are so short (less than a centimeter); measuring TDOA at nodes 801 may be beyond current technology. As an alternative, in an exemplary embodiment, the signal-strength-difference-on-arrival (SDOA) of an action potential 1701 may be measured among the eight nodes 801 of a cubic volume 1601. In free space or a homogenous material medium, the signal may attenuate at a rate of $1/R^2$, where R is the radius of the expanding sphere of EM energy. In an exemplary embodiment, the different EM energies 1702 may be received at different nodes 801, allowing the nodes to pinpoint the location of the dimensional space event. Also, in an exemplary embodiment, attenuations may enable deviations from the cubic space division 1601 of the physical array to be mathematically compensated in the computer model.

Turning now to exemplary FIG. 18, intermodal paths formed between a node 801 and the surrounding twenty-six nodes may be described. According to an exemplary embodiment, a further model correction may be used for interpreting signal measurements between nodes 801. Varying density and absorption properties of brain matter and structures along any particular $R^3$ vector transmission path may be evident. Cubic brain regions 1601 may have unique absorption peculiarities that deviate from free space—absorption characterization of the brain is required. Electrical resistivity between any two adjacent nodes 801 may be measurable different; this difference may be incorporated into model corrections as needed. Each node 801 in the 3D array 204 may be immediately surrounded by neighboring nodes 801, which may number between one and (more likely) twenty-six. According to an exemplary embodiment, once the array 204 is emplaced, the intermodal paths may be fixed and the electrical, RF and optical properties between node pairs may be measured. Also, in an exemplary embodiment, as with array distortion, mathematical corrections for transmissivity and resistance may provide the computer model with greater accuracy.

What follows is a less traumatic alternative to integrate a whole-mind interface device without the skull cap replacement, wherein the device is housed externally as a separable enhancement. Turning now to exemplary FIG. 19, FIG. 19 shows a cross-sectional view of the human cranium, where micro-passageways are drilled according to another exemplary embodiment. As an incremental step towards seamless bodily integration, an external device may be integrated with the brain without the need for cranial replacement. In order to access the brain, micropassagways may be drilled through an intact cranium in accordance with the precise template 1202 described above. The drill would penetrate through the: skin of the scalp 1901; periosteum 1902; skull bone 1903; periosteal dura mater 1904; and meningeal dura mater 1905. According to an exemplary embodiment, multiple rigid, precisely-installed and permanent passageways 1906 may permit the deep-brain penetration of 3D node array spokes 204 from without the intact skull. Also, in an exemplary embodiment, a spoke 204 is a chain of 1.5 mm diameter spherical transceivers 801 linked together by a 0.2 mm diameter bundle 802 of fibers (901, 902 and 903), conductors 904 and conduits 905. Further, an infection barrier 1908 may be a liquid or gelatinous plug inserted into each rigid passageway 1906 following spoke 204 insertion and tube (1101 in FIG. 11) withdrawal. The only permanent modifications to the cranium may be the cranium passage points 1906 needed to permit the deep brain insertion and external connectivity of node array spokes 204. Following passage point installation and node spoke insertion, the periosteum 1902, periosteal dura mater 1904 and other organic layers may heal and seal the spokes 204 and cranium.

Turning now to exemplary FIG. 20, the externally-worn device housing may be described. According to an exemplary embodiment, the externally-worn device housing 2001 may be substituted for the artificial cranium skull cap 201, and the device components 202 may be inside the externally-worn device housing 2001. This externally-worn alternative can allow the whole-mind cognitive interface device to be employed without the trauma associated with cranium removal. In accordance with an exemplary embodiment, reference numbers may depict: 2001: externally-worn device housing—the alternative to a cranium replacement; 204: 3D array of conductor-linked transceiver nodes—in this configuration, the 3D array of conductor-linked transceiver nodes 204 remains continuously and physically linked with the external computer 505; 501: optical sources of varying wavelengths and waveforms, as well as detectors; 502: AC and DC electrical power supplies and conditioning, which may include batteries, external power options, DC-AC inversion options, voltage variability, and waveform options; 505: computer, electrical, optical and radio frequency (RF) components; 503: capacitor bank for spark gap operation and artificial action potential generation; 504: variable wavelength RF source with phase shift capabilities for beam and hot-spot steering; 203: the conformal, phased array antenna; and 1906: cranium micro-passageways for external insertion of 3D array spokes into the brain—access points may be self-sealing/healing following array spoke insertion.

Turning now to exemplary FIG. 21, FIG. 21 shows PET scans of healthy brains on the left and brains suffering from PTSD, SA and AD on the right. As shown in FIG. 21, each mental disorder appears as specific patterns of neurons activities. Because the device may locate specific regions of the neuron activity and may create neuron activity in a specific region of a brain, there may be an opportunity to treat individuals who are severely debilitated by the illnesses.

Turning now to exemplary FIG. 22, notional working examples of the treatments for the mental disorders may be described. In the case of PTSD, once the device is trained, the user may employ positive feedback to generate internodal RF fields that locally suppress negative neuron activity (for example, bad memories), causing positive activity to dominate and reducing PTS (Post Traumatic Stress). In the case of SA, a trained device may permit a user to form alternative intellectual, non-chemically induced paths of satiation that circumvent, over-power, eclipse or negate addiction craving paths. In the case of AD, with the assistance of external sensory stimuli, dendrite-energizing internodal RF fields, on-site electrochemical nourishment, and possible electric field stimulation, dormant memories may be activated and amplified.

When digitally modeling thought, individual neuron action potentials are discrete events. At any moment, a neuron is either firing or not firing, so the individual neuron can be modeled as 0 s and 1 s. A snapshot capturing all neuron action potential activity throughout the brain can be considered an instantaneous state of mind. To the extent that each action potential may be spatially located by a device, instantaneous states of mind may be modeled in 3D space. Across unbounded 3D space, the number of unique binary states may be $2^N$, where N is the number of nodes that are either 1 or 0. Furthermore, there may exist $(2^N)!$ unique permutations of $2^N$ states, and $(2^N)!/2^{N-n}$ subsets having various lengths within those permutations. Thus, modeling mind states by granular approximations may be possible.

Turning now to exemplary FIG. 23, the two-dimensional model in which the state of mind is visualized as a 2D frame may be described. According to an exemplary embodiment, the four-node case may constitute a simple two-dimensional model that is visualized as a 2D frame. Four nodes may enable twenty-four or sixteen unique frames 2301. Also, there may exist (24)! permutations of sixteen unique 2D frames, where each frame may be included exactly once per permutation. (24)! is equal to 20,000,000,000,000 unique 2D frame sequences 2302.

Turning now to exemplary FIG. 24, a three-dimensional abstraction of the modeling may be described. The adult human brain may contain 100,000,000,000 ($2^{10^{0.11}}$) neurons. Therefore, there are $2^{100,000,000}$ possible unique, instantaneous digital states of mind (2401—a 3D abstraction). Progressions of whole-brain frames 2402 can be considered human thought, whether conscious, unconscious, brain stem or a combination of those cognitive levels. There may exist $(2^{10^{0.11}})!$ permutations of $2^{10^{0.11}}$ unique states, where each state is included once in each permutation and an even greater number of unique subsets is included. With discrete thoughts as subsets of those permutations, the number of possibilities is uncountable. However, given a whole-mind/brain detection capability, instantaneous 3D frames and progressions of 3D frames 2402 may be usefully approximated.

Exemplary FIG. 25 may describe a case of the question-answer scenario where a labeled map is observed, along with a verbal assertion that it is the country of France. The exemplary scenario considers a human being augmented with the device, and biological processes and the parallel machine are aboard that platform. During the first phase of the scenario, the device-enhanced adult human is briefly presented specific knowledge via visual and aural sensory pathways. A labeled map of France is accompanied by a verbal statement confirming that the visual image is indeed France—a new fact that requires no further analysis for acceptance. This fact is sensed and committed to short-term memory with an associated whole-brain neuron activity over a finite period of time.

Turning now to exemplary FIG. 26, FIG. 26 shows the notional snapshots of neuron activities detected by the phased array antenna 203 and the 3D node array 204. According to an exemplary embodiment, the device may detect and record three-dimensional snapshots of neuron activity throughout the brain in two distinct granularity classes: regional 2601; and local 2602. In 2601, the phased array antenna 203 may receive regional neuron activity—less granular images of whole-brain activity with event stand-off distances of between 1 and 20 cm. In 2602, the 3D node array 204 may detect and images of local neuron action potentials with event stand-off distances of between 1 and 10 mm.

Turning now to exemplary FIG. 27, FIG. 27 shows the modeling of the human thought process as a series of 3D snapshots. As the natural human thought proceeds, subsequent 3D images may be captured with a certain frequency and duty cycle. At any specific moment, the brain activity may be imaged at two levels of granularity—local 2601 and regional 2602—simultaneously, for synthesis into 3D snapshots that may be compared with 3D movie frames. In 2701, these granular and regional snapshots may be time-stamped and scaled compatibly for synthesis in a discrete, static 3D computer model—for example, a single movie frame. In 2702, as the thought unfolds, a series of static frames may be synthesized and assembled into a time series, forming a short movie of the natural thought that may be replayed.

According to an exemplary embodiment, the neuron activities during duration of human thought may illustrated as a graph shown in exemplary FIG. 28. 2801 is the discrete distribution of the graph which may represent the collective neuron activity throughout the brain during the duration of thought—it may be seen as defining a curve capturing neuron energy. 2802 is the X axis which may depict the duration of the thought, and image frames and duty cycles—shorter frames and smaller duty cycles equal higher temporal granularity. 2803 represents the cycled rectangles, and the separations between each rectangle may represent the duration/granularity of the instantaneous activity snapshot frames and their duty cycles. 2804 is the Y axis which may represent the peak instantaneous neuron activity throughout the human brain.

Turning now to exemplary FIG. 29, the second phase of the question-answer scenario case may be described. After a pause during which the short-term memory of the original, the device-enhanced adult human may be presented an unlabeled shape—an apparently random shape with a random color pattern. In the same instant that the image is presented, a question may be verbally asked, "What country is this?" as the questioner gestures towards the image. In this case what is presented may be ambiguous visual and aural stimulation rather than specific knowledge—no facts are presented for instant comprehension. According to an exemplary embodiment, the device may again detect, compute and memorize a natural human thought as a time series of three-dimensional frames that synthesize local and regional neuron activity. However, because the stimulus was ambiguous, and because the query was a prompt for autonomous action, the regional and individual neuron activity may be different than that observed in the first scenario. There may be a significant "cognitive distance/dissimilarity" between the two experiences that may require the human brain and the device to be analyzed over a finite period of time. The brain and the device may receive inputs at the same instant: the brain as sense-stimulated neuron activity, and the device as neuron spike RF emissions. The question may be recognized by both the device and the brain as a prompt for a limited autonomous action, namely to process and answer the question. Thereafter, separately but in parallel, the brain and the device may employ pattern recognition analytical tools in pursuit of a correct answer. The answer—"France"—already resides in the brain and device memories. Both may employ fuzzy logic over a finite time period in order to arrive at that answer. The average human may arrive at the probable answer within one to several seconds, with electro-chemical-based processing speeds of <100 meters per second. The computer 505 may arrive at the probable answer within nanoseconds, with electrical conduction-based processing speeds of at least 280 million meters per second.

Upon answer determination, the computer 505 may automatically play back the modeled answer through targeted RF, optical and electrical neuron stimulation. This artificial thought regeneration may involve the transformation and energetic projection of the time series of 3D frames of neuron activity received and stored in memory ("2702" in FIG. 27). This device intervention in the human may cause the human to think and answer "France" instantaneously, outpacing the lagging biological process. The re-stimulation of the brain by the device may cause a rough approximation of the stored thought. An exemplary embodiment may have a 3D node array encompassing the 1,260 cubes of brain matter into which the human brain can be compartmentalized on a centimeter scale with 100-200 spokes and 2,000 nodes. However, an increased number of spokes 204 and nodes 801 may result in a more precise approximation of the human thought.

Turning now to exemplary FIG. 30, FIG. 30 is a flowchart illustrating a basic device recording procedure of a human thought. First, in the exemplary step 3001, external stimuli may reach the brain through human sensory inputs, and brain-wide neuron activity may occur. The steps 3002 and 3003 proceed concurrently. In 3002, the phased array antenna 203 may detect RF signatures of regional neuron activity. According to an exemplary embodiment, the device may take time-stamped snapshots of instantaneous states of mind (ISOM); the computer 505 then employs TDOA (time-difference-on-arrival) and triangulation for regional modeling of the ISOM. Simultaneously, at the step 3003, the 3D node array 204 may detect RF signatures of local neuron activity. According to an exemplary embodiment, the device may also take time-stamped snapshots of instantaneous states of mind (ISOM); the computer 505 then employs SDOA (signal-strength-difference-on-arrival) for local modeling of the ISOM. In the step 3004, the computer 505 may synthesize the regional and local ISOMs into a static ISOM frame (2701: the single 3D snapshots in FIG. 27). The static ISOM frame 2701 may be stored in a computer 505 RAM, and each sequential static frame may be integrated into a time series (2702: the series of static frames in FIG. 27). The series of ISOM frames 2702 may then be sent to ROM with a title as a unique thought.

Turning now to exemplary FIGS. 31A-D, FIGS. 31A-D show a flowchart in which the human thought recording procedure is applied to the above question-answer scenario case. In the exemplary step 3101 of FIG. 31A, a labeled map is observed by a brain owner, along with a verbal assertion, "it is the country of France", and brain-wide neuron potential spikes may correspond to the combination of query stimuli. As the basic recording procedure, the steps 3102 and 3103 proceed concurrently. In 3102, the phased array antenna 203 may detect RF signatures of regional neuron activity. The device may take time-stamped snapshots of ISOM; the computer 505 then employs TDOA (time-difference-of-arrival) and triangulation for regional modeling of the ISOM. Simultaneously, at the step 3103, the 3D node array 204 may detect RF signatures of local neuron activity. According to an exemplary embodiment, the device may also take time-stamped snapshot of ISOM; the computer 505 then employs SDOA for local modeling of the ISOM. In the step 3104, the computer 505 may synthesize the regional and local ISOMs into a static 3D ISOM frame 2701, and each incoming sequential static frame may be integrated into a time series 2702 as a new thought—a fact. The series of ISOM frames 2702 may then be sent to ROM with a title as a unique thought—in this example, the thought is the registration by the brain owner that he or she is looking at an image of France (herein referred to as "France fact").

Figure 31A:
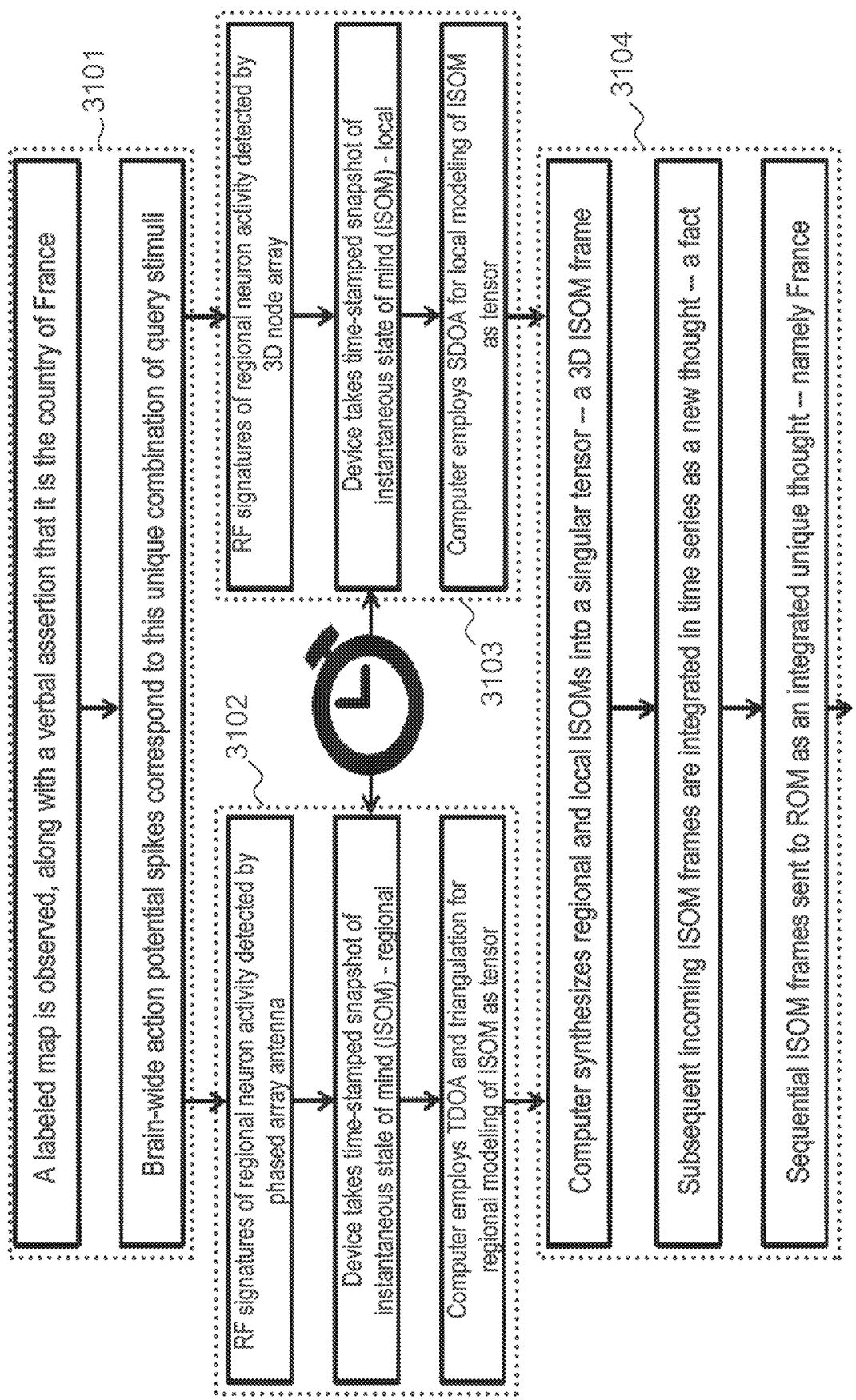
Figure 31B:
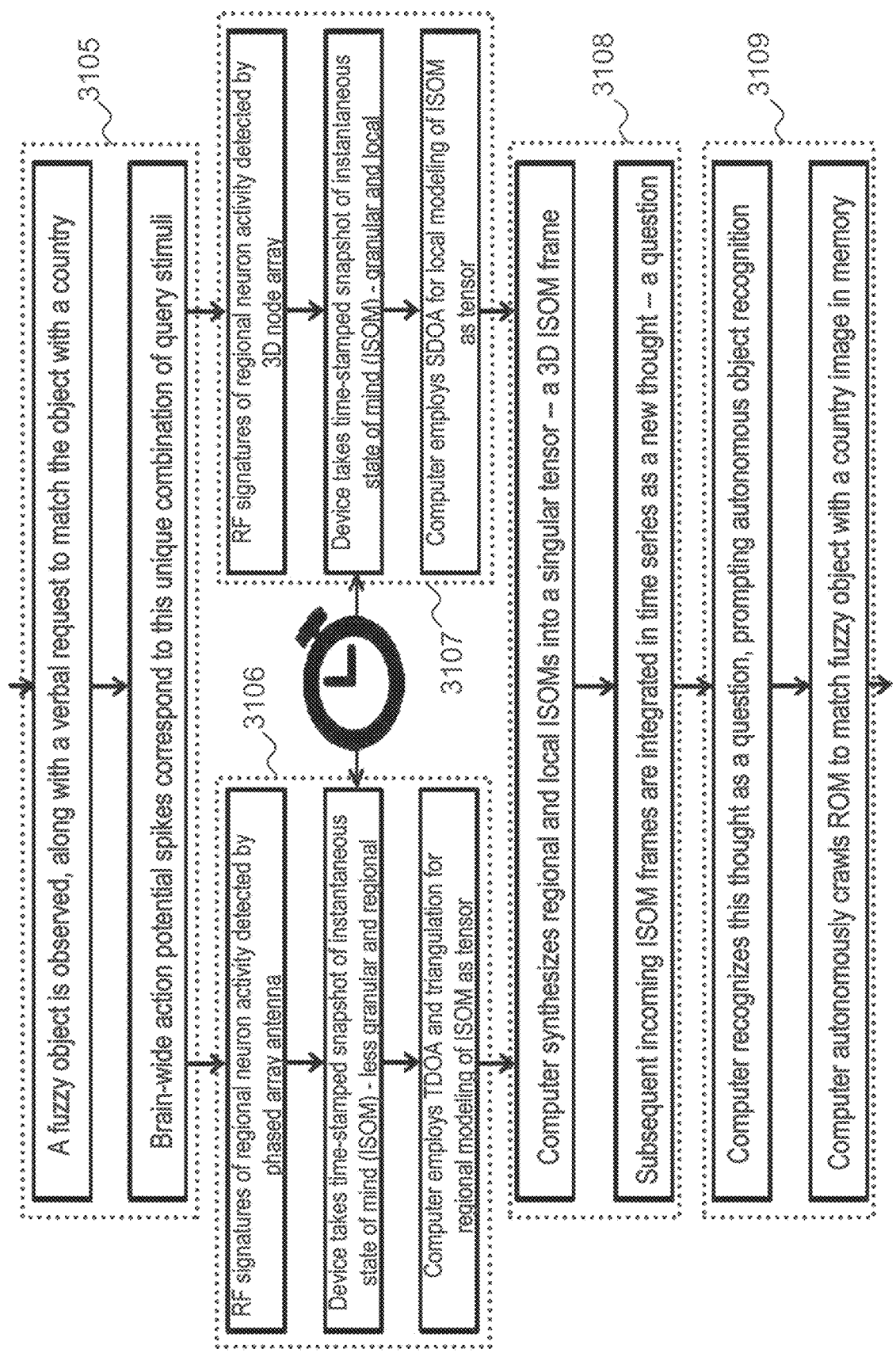

Referring to exemplary FIG. 31B, in the step 3105, a fuzzy object is observed by the brain owner, along with a verbal request to match the object with a country, and brain-wide neuron potential spikes may correspond to the combination of query stimuli. In 3106, the phased array antenna 203 may detect RF signatures of regional neuron activity, and the regional ISOM may be modeled by the same procedure above. In parallel, at the step 3107, the 3D node array 204 may detect RF signatures of local neuron activity, and the local ISOM may be modeled by the same procedure described above. In the step 3108, by the same procedure described above, the computer 505 may integrate a series of ISOM frames 2702 as a new thought—a question. Then, in the step 3109, the computer 505 may recognize this thought as a question prompting autonomous object recognition, and the computer 505 autonomously may crawl ROM to match the fuzzy object with a country image in the memory.

Figure 31C:
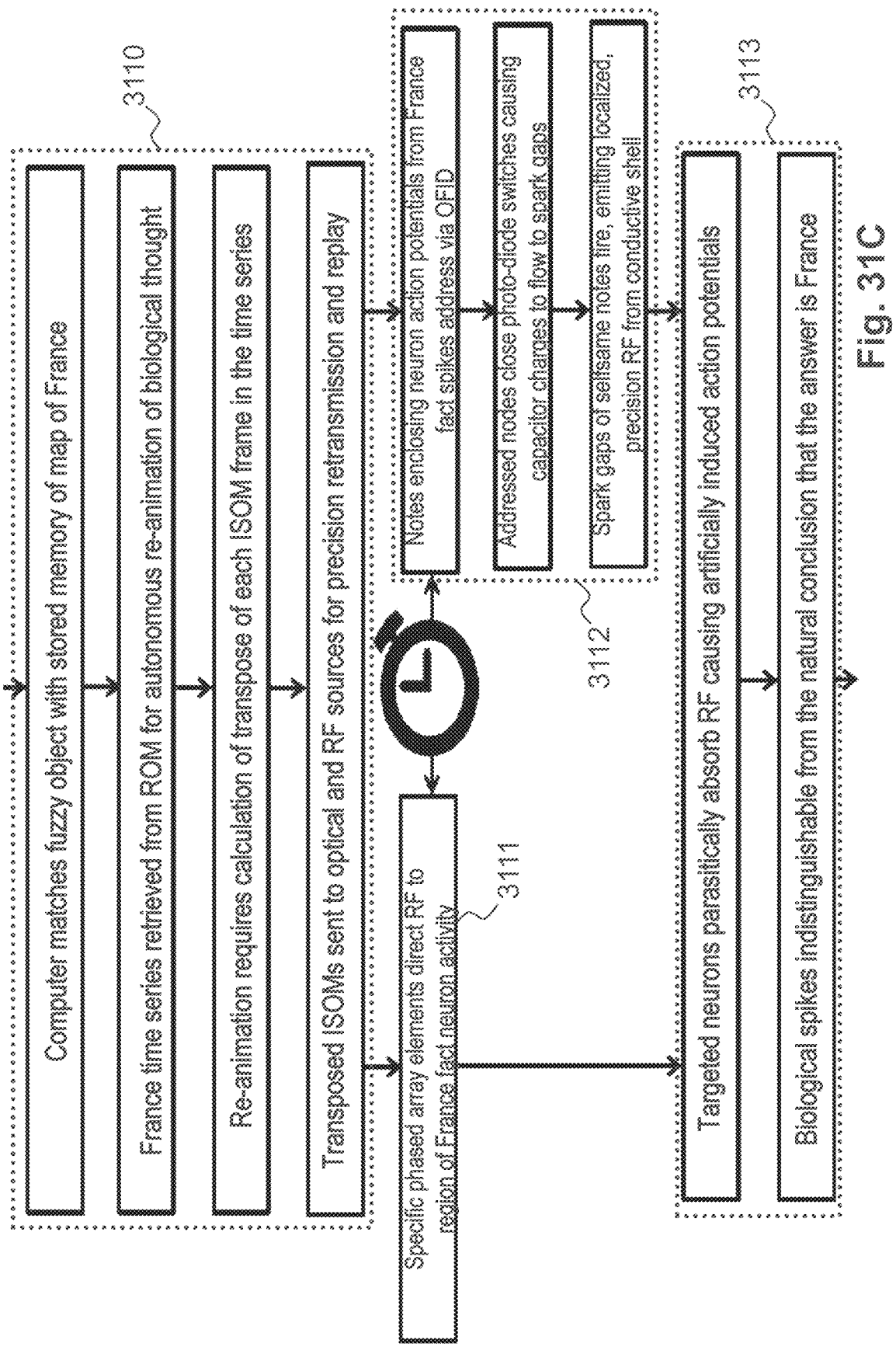

Referring to exemplary FIG. 31C, in the step 3110, the computer 505 may match the fuzzy object with map of France stored in the memory and retrieve the series of ISOM frames 2702 titled as "France". Then, the computer 505 may proceed through an autonomous re-animation of the biological thought in accordance with the series of ISOM frames 2702 retrieved from ROM. According to an exemplary embodiment, the re-animation may require calculation of transpose of each ISOM frame 2701 in the time series 2702. After the calculation, the transposed ISOMs may be sent to optical and RF sources (501 and 504 in FIG. 5 or 20) for precise retransmission and replay. The steps 3111 and 3112 proceed concurrently. In the step 3111, a specific phased array element 203 may direct RF to the region in which the "France fact" produced the neuron activity. In parallel, at the step 3112, the nodes 801 enclosing the neuron action potentials caused by the "France fact" spikes may be addressed via OFID (optical frequency ID: 1002 in FIG. 10), and the addressed nodes may close photo-diode switches (1009 in FIG. 10) causing capacitor charges (1001 in FIG. 10) to flow to spark gaps. The spark gaps of selfsame nodes may fire and emit localized precise RF from their conductive shell (1007 in FIG. 10). In the step 3113, targeted neurons may parasitically absorb RF, causing artificially-induced action potentials, and the biological spikes may be indistinguishable from the natural conclusion that the answer is France.

Figure 31D:
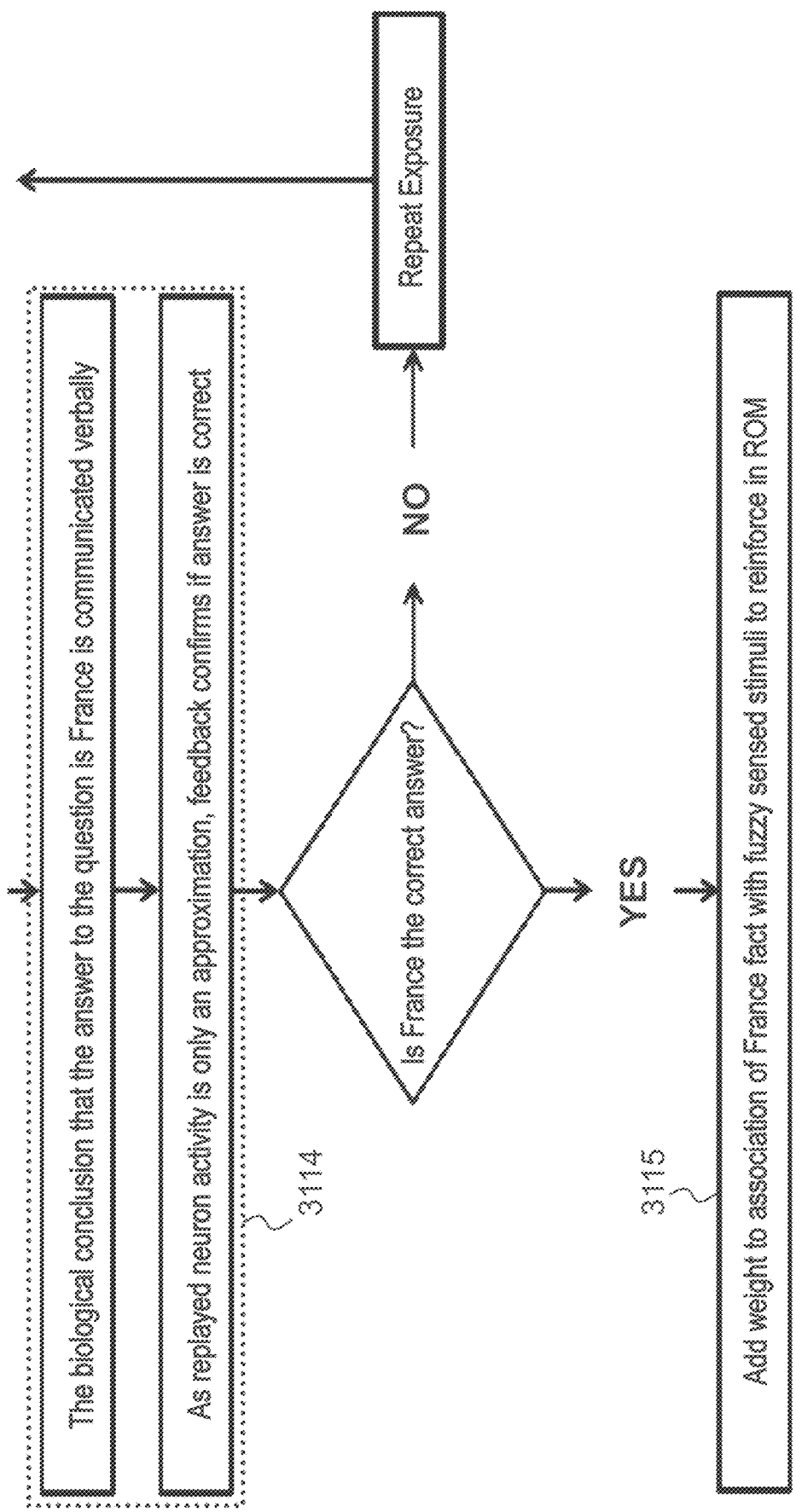

Referring to exemplary FIG. 31D, in the step 3114, the biological conclusion that the answer to the question is "France" is communicated verbally by the brain owner. Because the replayed neuron activity is only an approximation of the thought, feedback may confirm if the answer is correct. If the answer is correct, proceeding to the step 3115, the association between the series of ISOM frames 2702 and the "France fact" may be deemed valid in ROM. However, if the answer is incorrect, the procedure may be repeated, starting from step 3101.

Turning now to exemplary FIGS. 32A-C, FIGS. 32A-C are flowcharts illustrating the human thought recording procedure applied to counter addictions. In the exemplary step 3201 of FIG. 32A, an addict brain owner is denied a narcotic, and the brain-wide neuron activity may correspond to and reflect distress caused by the withdrawal of a narcotic. In the step 3202, the phased array antenna 203 may detect RF signatures of regional neuron activity, and the regional ISOM may be modeled by the same procedure described above. Simultaneously, at the step 3203, the 3D node array 204 may detect RF signatures of local neuron activity, and the local ISOM may be modeled by the same procedure described above. In the step 3204, the computer 505 may synthesize the regional and local ISOMs into a static 3D ISOM frame 2701, and each incoming sequential static frame may be integrated into a time series 2702 as a feeling of distress. The series of ISOM frames 2702 may reveal "centers" of the distress and their action potential causal "origins".

Referring to exemplary FIG. 32B, in the step 3205, the distress of the brain owner is relieved by narcotic administration, and brain-wide neuron activity may correspond to and reflect satiation caused by the narcotic. In the step 3206, the phased array antenna 203 may detect RF signatures of regional neuron activity, and the regional ISOM may be modeled as the same procedure above. In parallel, at the step 3207, the 3D node array 204 may detect RF signatures of local neuron activity, and the local ISOM may be modeled by the same procedure described above. In the step 3208, the computer 505 may synthesize the regional and local ISOMs into a static 3D ISOM frame 2701, and each incoming sequential static frame may be integrated into a time series 2702 as a feeling of satiation. The series of ISOM frames 2702 may reveal centers of the satiation and their action potential causal origins. Then, the computer 505 may map alternative origin-to-center paths: distress-to-satiation, and satiation-to-distress.

Referring to exemplary FIG. 32C, in the step 3209, pertinent nodes 801 along the alternative paths may be electrically energized by the hub (the main components 202 including the cognitive computer 505 inside the artificial cranium cap 201). The sequence and duration of the electric fields may be optimized by the device to accelerate dendritic growth, and periodic and in-stride stimulation of distress and satiation path origins help to validate the map of the paths. Stimulation of whole-mind activity may be repeated as before—narcotic withdrawal and exposure, and if the narcotic exposure leads to distress instead of satiation and the narcotic withdrawal leads to satiation, proceeding to the step 3210, it may be the case that the alternative dendritic paths have therapeutic value and the alternative dendritic paths may be periodically reinforced with E-fields. However, if the narcotic exposure still leads to satiation and the narcotic withdrawal leads to distress, the exposure of the alternative path to electric fields may be repeated.

Turning now to exemplary FIGS. 33A-D, FIGS. 33A-D are a flowchart illustrating the human thought recording procedure applied to reenergize neurons for Alzheimer's Disease (AD). In the exemplary step 3301 of FIG. 33A, an early stage AD patient is asked multiple questions requiring short-term and long-term memory, and brain-wide neuron activity may illustrate 3D cognitive development of responses to each query. In the step 3302, the phased array antenna 203 may detect RF signatures of regional neuron activity, and the regional ISOM may be modeled by the same procedure described above. Simultaneously, at the step 3303, the 3D node array 204 may detect RF signatures of local neuron activity, and the local ISOM may be modeled by the same procedure described above. In the step 3304, the computer 505 may synthesize the regional and local ISOMs into a static 3D ISOM frame 2701, and each incoming sequential static frame may be integrated into a time series 2702 as a stimulus response. The series of ISOM frames 2702 may then be sent to ROM with a title as a unique response. Multiple series of ISOM frames 2702 may be stored in ROM as a date-stamped set for future comparison.

Figure 33A:
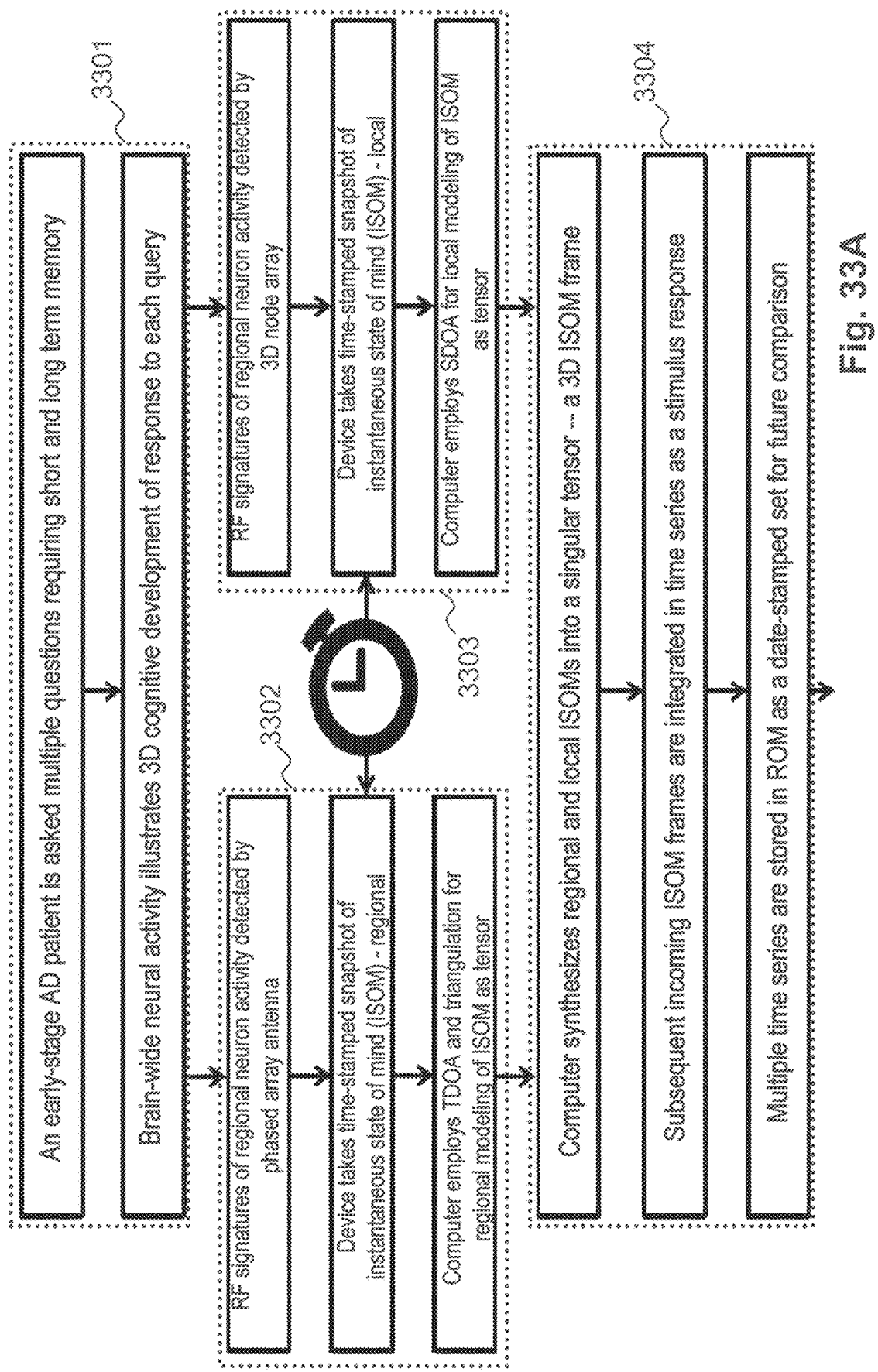
Figure 33B:
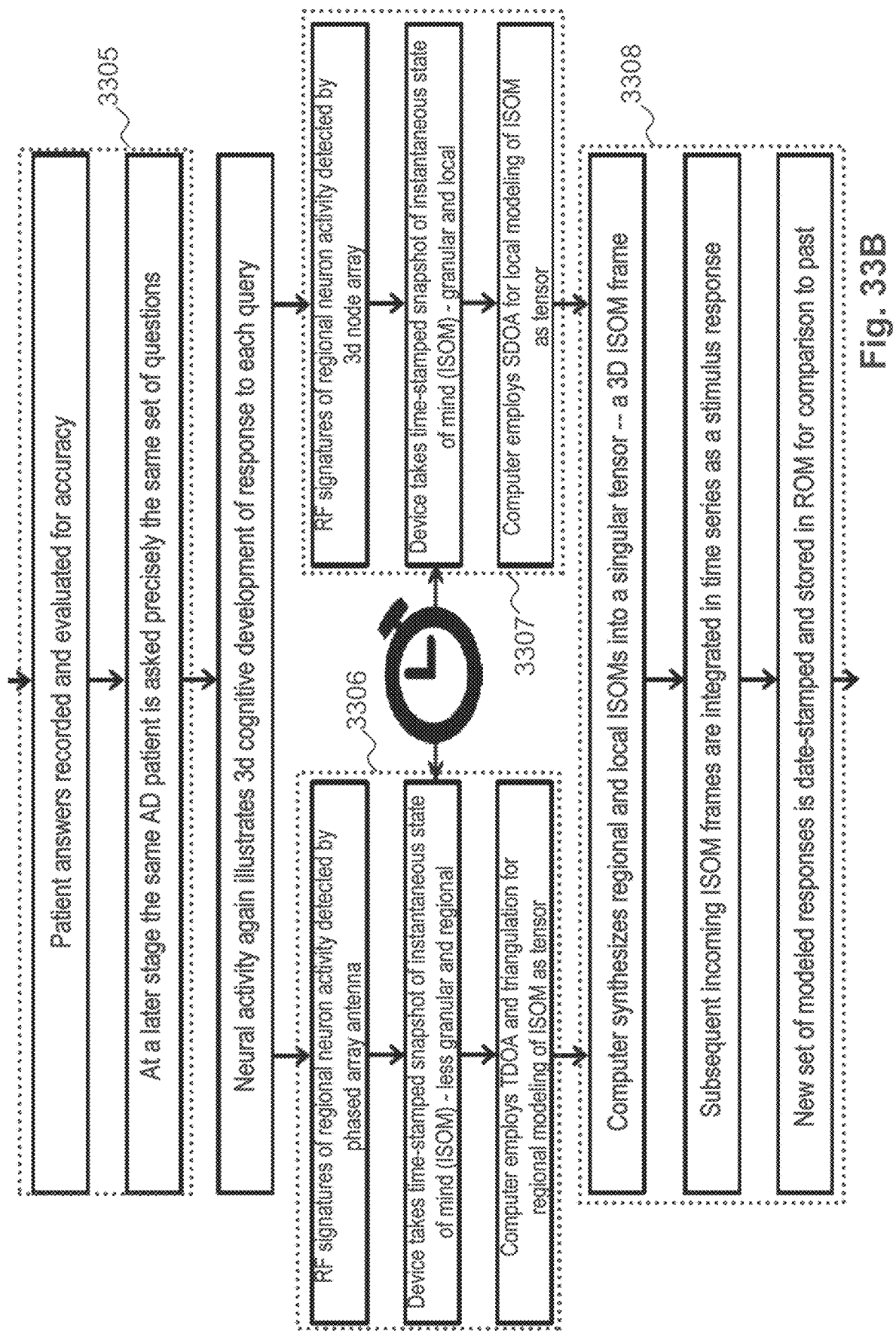

Referring to exemplary FIG. 33B, in the step 3305, the patient answers may be recorded and evaluated for accuracy. At a later stage, the same AD patient is asked precisely the same set of questions, and neuron activity again may illustrate 3D cognitive development of responses to each query. In the step 3306, the phased array antenna 203 may detect RF signatures of regional neuron activity, and the regional ISOM may be modeled by the same procedure described above. In parallel, at the step 3307, the 3D node array 204 may detect RF signatures of local neuron activity, and the local ISOM may be modeled by the same procedure described above. In the step 3308, the computer 505 may synthesize the regional and local ISOMs into a static 3D ISOM frame 2701, and each incoming sequential static frame may be integrated into a time series 2702 as a stimulus response. The series of ISOM frames 2702 may then be sent to ROM with a title as a unique response. The new set of ISOM frames 2702 may be date-stamped and stored in ROM for comparison to the past date-stamped set.

Figure 33C:
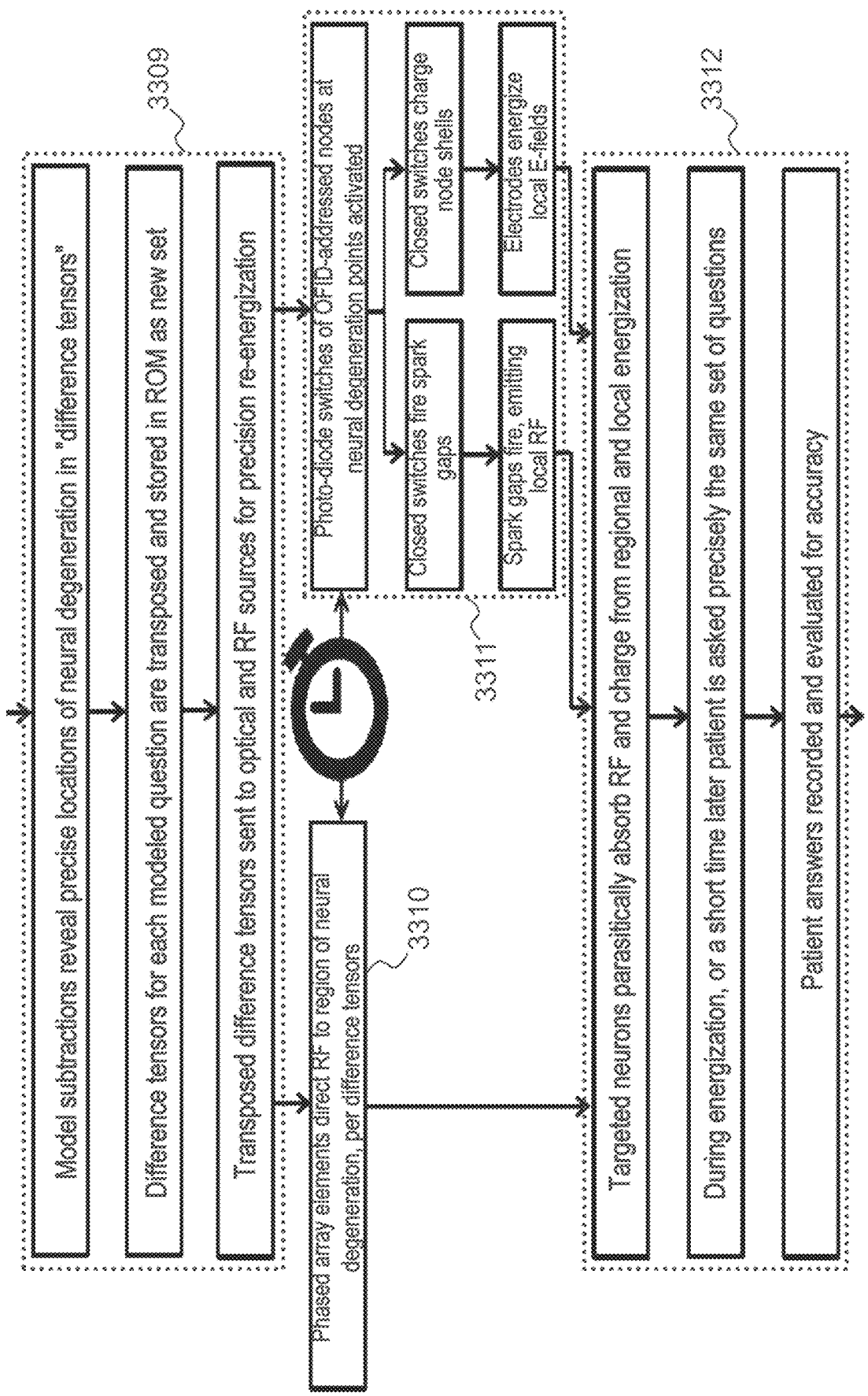

Referring to exemplary FIG. 33C, in the step 3309, as a result of the comparison between the sets of ISOM frames, model subtractions may reveal precise locations of neuron degeneration in "difference tensors". Difference tensors for each modeled question may be transposed and stored in ROM as new set, and the transposed difference tensors may be sent to optical and RF sources (501 and 504 of FIGS. 5 and 20) for precise re-energization. In the step 3310, the phased array elements 203 may, guided by the difference tensors, direct RF to the region of neuron degeneration. In parallel, at the step 3311, the photo-diode switches (1009 in FIG. 10) of OFID-addressed nodes 801 at neuron degeneration points may be activated. Then, in parallel, the closed switches 1009 may fire spark gaps emitting local RF and may charge node shells 1007, their electrodes energizing local E-fields (1004 in FIG. 10). In the step 3312, targeted neurons may parasitically absorb RF and charge from regional and local energization. During the energization or a short time later, the patient is asked precisely the same set of questions, and the patient's answers may be recorded and evaluated for accuracy.

Figure 33D:
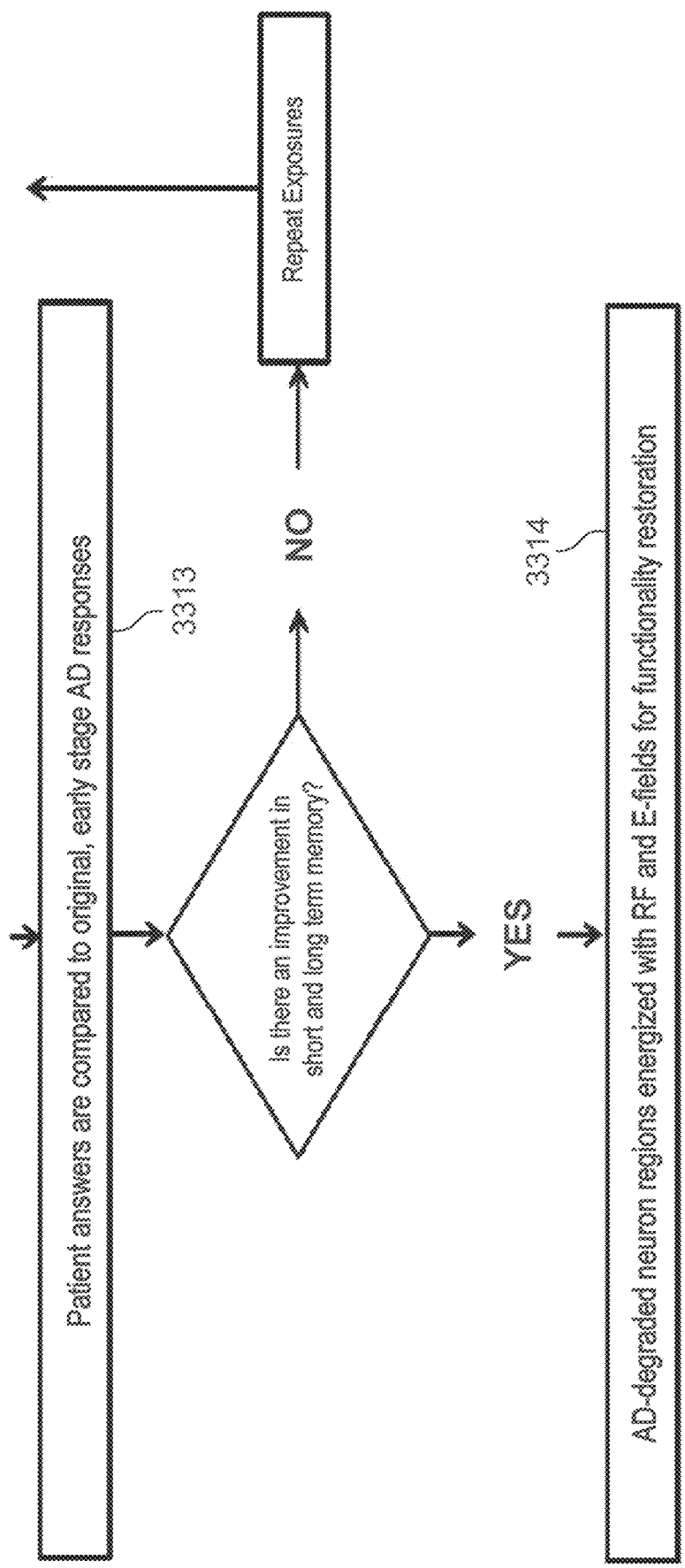

Referring to exemplary FIG. 33D, in the step 3313, the patient's answers may be compared to original, early-stage AD responses. Proceeding to step 3314, an improvement in short-term and long-term memory may confirm that AD-degraded neuron regions experienced functionality restoration after being energized with RF and E-fields. However, if there is no improvement, the procedure may be repeated, starting from step 3101.

According to another embodiment, referring to exemplary FIG. 34, the strings 802 of 3D node arrays 204 may comprise tubes made of semi-conductors. Multiple deeply-inserted spokes 204 with nodes 801 connected by permanent conductors 802 could prove to be hazardous to both natural and artificial cognition under certain circumstances. Natural and man-made High-Power Radio Frequency (HPRF) emissions, such as solar flares, electromagnetic pulses (EMP), or HPMW weapons, can generate currents and voltages in array conductors. These currents and voltages can cause upset, latch-up and even arching-induced burn-out within the device, as well as damage to the brain. Furthermore, a conductive array provides a back-door cyber entry point to the computer and device components for nefarious hacking of host cognitive functions. An alternative to conductors is the employment of laser-activated semi-conductors that may permit current to flow only upon laser illumination. This may ensure that all components and connections in the array 204 that remain as insulators and that are not in instantaneous use are under the positive command of the device computer 505.

Turning now to exemplary FIG. 35, a cross-sectional view of the string 802 of the three-Dimensional array of semi-conductor-linked transceiver nodes 204 may be described. The shorter wavelength visible laser fiber 901, the medium wavelength visible laser fiber 902 and the longer wavelength visible through IR laser fiber are the same as those displayed in FIG. 9. In accordance with an exemplary embodiment, reference numbers of FIG. 35 which are different from FIG. 9 may depict: 3501: UV light-activated fiber optic semiconductor to ensure that the spoke is only electrically conductive when commanded by the hub (the main components 202 including the cognitive computer 505 inside the artificial cranium cap 201); 3502: UV light-activated common ground, again only conductive when commanded by the hub (otherwise it serves as an insulator); and 3503: Hollow spare conduits for liquid, gas, or other brain access —unused paths for unplanned future access, including the installation of electrically-conductive wire.

Turning now to exemplary FIG. 36, FIG. 36 shows a three-dimensional perspective view looking down an individual 3D array spoke 204 towards a single node 801, as they may be seen from the hub. According to an exemplary embodiment, the UV laser source (501: the optical source) may be located at the hub (the main components 202 including the cognitive computer 505 inside the artificial cranium cap 201) under the control of the computer 505, and the UV laser source 501 may send lights as a command to the semiconductor electrode energizing fiber (3501: the UV light-activated fiber optic semiconductor) of a 3D array spoke 204. Also, in an exemplary embodiment, the semi-conductor ground (3502: the UV light-activated common ground) is the common ground for all semiconductors in that spoke 204. Once the GaAs layer of the electrode fiber (3501 and/or 3502) is made conductive by the UV laser source 501, node transceiver functions may be enabled by charging;

these functions may include: i) Hub electrical reception of node-detected RF signals resulting from local neuron activity; ii) Hub discharging of the capacitor bank 503 for local RF signal generation; and iii) Hub energizing of conductive node surfaces 1007 for employment as positively—or negatively-charged electrodes that may influence local dendritic growth.

Turning now to exemplary FIG. 37, FIG. 37 shows a working mechanism of the semiconductor fibers (3501 and 3502). In accordance with an exemplary embodiment, reference numbers may depict: 3701: Internal fiber medium through which coherent UV light passes; 3702: Sandwiched semiconducting film layer made of Gallium Arsenide (GaAs); 3703: External electrically insulating protective cladding; 3704: Optically reflective doping/impurities made of Aluminum or Silver in the form of micron-scale spheres or multifaceted polyhedrons; 3705: Coherent UV rays traveling coaxially from the laser source through the fiber; 3706: UV light scattered off the surface of the reflective impurities; and 3707: UV-illuminated photoelectrons raised in energy passing across the energy gap between valence and conduction bands in the GaAs semiconductor.

Turning now to exemplary FIG. 38, FIG. 38 shows a notional cross-section view of the node 801 of the three-dimensional array of semiconductor-linked transceiver nodes 204. FIG. 38 is identical to FIG. 10 except for 3801: Electrical, UV-laser-energized fiber semi-conductors (3501) which may deliver AC, DC and tailored waveforms. These fibers 3501 terminate at specific addressable nodes 801 with electrodes having multiple purposes, which may include, but are not limited to, continuous inter-nodal E-field generation for dendrite growth and local biological neuron spike stimulation. For both conductor-linked transceiver nodes (FIG. 10) and semiconductor-linked transceiver nodes (FIG. 38), selected fibers may terminate at individual nodes 801 for executing actions with 3D spatial precision, such actions including, but not limited to, local optical—UV, color or IR—illumination, artificial action potential creation, and a node surface 1007 charging. As described above at FIG. 10, in cases where the number of nodes 801 along an individual spoke 204 exceeds the spoke ability to host a dedicated fiber for each, OFID may be employed for node addressing.

Referring now to exemplary FIG. 39 for specific descriptions of light dispersion/scattering from the node 801, FIG. 39 shows micron-scale windows on the surface 1007 of the node 801. According to an exemplary embodiment, the small, micron-scale windows 3901 may permit the passage and dispersion/scattering of coherent and incoherent light. The light sources may be the laser sources 501 contained within the hub (the main components 202 including the cognitive computer 505 inside the artificial cranium cap 201). The omnidirectional dispersion and scattering of light from individual nodes may be achieved by one of two means: i) Fibers (901, 902, or 903) that serve as conduits for selected optical wavelengths terminate within a light-transmissive node shell 1007 that includes micron-scale windows 3901 for dispersion; and/or ii) Alternatively, fibers (901, 902, or 903) that serve as conduits for selected optical wavelengths may terminate within the volume of the sphere at a reflective/scattering polyhedron.

As another exemplary embodiment, the same nodes 801 may also be independently embedded throughout the brain in an identically grid-structured topology as that described above. Referring to exemplary FIG. 40, FIG. 40 shows the self-embedding of the node 801. The embedding may be accomplished by node self-mobility or by hypo-cranial, gravitational, magnetic, circulatory or other forms of insertion. In accordance with an exemplary embodiment, reference numbers may depict: 4001: Independent node 801 inserted with biodegradable cloak to permit movement and manipulation until arrival at the designated grid intersection destination; and 4002: Degradation of the hydrodynamic cloak may cause positional fixation of the node 801 in selected position.

Advances in energy density, component miniaturization, and nanorobotic mobility for node stationing may permit aforementioned node capabilities to be onboard independent platforms. Wireless connectivity may also enable networking, and independent power supplied from local energy harvesting may provide self-sufficiency. As before, the critical enabling capability of the 3D array 204, even for a wireless cloud of micro systems, is that of spatial station keeping. The nodes must maintain the clear grid-structured topology of the array, so as to serve as the foundation for accuracy of tensor models of instantaneous states of mind.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A device of whole-mind cognitive interface comprising:
    an artificial cranium cap;
    a hub that is nested inside, the artificial cranium cap, the hub comprising a cognitive computer, a detector, and a signal generator
    wherein the hub is configured to locate, with the detector of the hub, at least one natural neuron event in a brain, record, with the cognitive computer of the hub, at least one of an instantaneous state of mind (ISOM) and a series of ISOMs by the located at least one natural neuron event, replay, with the signal generator of the hub paired with the cognitive computer of the hub, the at least one of the recorded ISOM and the recorded series of ISOMs by approximating the at least one of the recorded ISOM and the recorded series of ISOMs, wherein the approximating further comprises generating at least one artificial neuron activity in the brain, wherein the at least one artificial neuron activity is generated, based on the signal generator of the hub, at a predetermined location of the brain;
    a phased array radio frequency (RF) antenna and RF source that is nested on an internal surface of the artificial cranium cap and which is communicatively coupled to the hub, and which, under the control of the hub, is configured to detect, together with the detector of the hub, at least one detected RF electromagnetic signal from the at least one natural neuron event in the brain and transmit the at least one transmitted RF electromagnetic signal for the at least one artificial neuron activity based on output of the signal generator; and
    a plurality of 3D array nodes configured to be inserted into the brain which, under the control of the hub, is configured to detect, together with the detector of the hub, the at least one: electromagnetic signal from the at least one natural neuron event, and transmit, for the at least one artificial neuron activity, based on output of the signal generator, at least one of: optical signals by an optical source, and the 3D array node electromagnetic signals by an electromagnetic signal source.

2. The device of claim 1, wherein the hub further comprises:
an electrical power unit that, under the control of the cognitive computer, is configured to supply electrical power to the device of the whole-mind cognitive interface, is configured to maintain a condition of the electrical power and further includes at least one of batteries and an external power port;
the optical source, wherein the optical source is configured to, under the control of the cognitive computer, generate the optical signals transmitted to the 3D array nodes;
at least one optical detector that, under the control of the cognitive computer, detects the optical signals transmitted by the 3D array nodes;
a capacitor bank that is connected to the 3D array nodes and controlled by the cognitive computer; and
the electromagnetic signal source, wherein the electromagnetic signal source is configured to, under the control of the cognitive computer and connected to the phased array antenna, generate the 3D array node electromagnetic signals with a phase shifter.

3. The device of claim 1, wherein the artificial cranium cap is configured to replace an organic cranium.

4. The device of claim 1, wherein the artificial cranium cap is configured to be externally worn on a human head, and the plurality of 3D array nodes are configured to be inserted into the brain via a plurality of cranium micro passageways on the human head.

5. The device of claim 1, wherein the phased array antenna, together with the detector of the hub, is configured to detect the at least one detected RF electromagnetic signal through triangulation and a time-difference-of-arrival (TDOA) calculation of the at least one detected RF electromagnetic signal, and is further configured to transmit the at least one transmitted RF electromagnetic signal through the triangulation of the at least one detected RF electromagnetic signal.

6. The device of claim 1, wherein each 3D array node comprises a plurality of nodes and a string which links each node, a first end of the string is connected to the hub and a second end of the string is configured to reach to the end of the brain after being inserted into the brain, and the plurality of 3D array nodes are configured to form a plurality of cubic space divisions that segments the brain with a predetermined volume, and wherein a node in the plurality of nodes of the plurality of 3D array nodes is configured to be located at each vertex of the cubic space division to detect the at least one electromagnetic signal within the cubic space division through a signal-strength-difference-on-arrival (SDOA).

7. The device of claim 6, wherein the string of the plurality of 3D array nodes comprises:
a plurality of laser fibers configured to transmit at least one of Ultraviolet (UV) and Infrared (IR) light between the hub and the node;
at least one semiconductor electrode energizing fiber that has a Gallium Arsenide (GaAs) layer and which becomes conductive when at least UV light is sent to the semiconductor electrode energizing fiber from the hub to deliver electrical signals between the hub and the node;
at least one semiconductor ground that is a common ground for the at least one semiconductor electrode energizing fiber having the GaAs layer and which becomes conductive when at least UV light is sent to the semiconductor ground from the hub; and
at least one electrical conductor that delivers the electrical signals between the hub and the node.

8. The device of claim 6, wherein each node in the plurality of nodes of the plurality of 3D array nodes comprises:
at least one local capacitor charge storage;
a Radio Frequency Identification (RFID) configured to give an address of the node to the phased array antenna via triangulation;
an Optical Frequency Identification (OFID) configured to give the address of the node to the hub;
at least one photodiode configured to trigger at least one spark gap event from at least one optical signal being controlled by the hub and cause at least one local artificial neuron activity;
a spark gap unit configured to trigger the at least one spark gap event from at least one electrical signal controlled by the hub and cause the at least one local artificial neuron activity;
a conductive shell configured to transmit the 3D array node electromagnetic signals from the at least one spark gap event to cause the at least one local artificial neuron activity and detect the at least one electromagnetic signal from the at least one natural neuron event;
at least one electrode configured to charge the conductive shell and become a terminal point of signals from the hub by controlling of the hub; and
a plurality of micro-scale windows on the conductive shell that are configured to provide an omnidirectional dispersion of lights which are delivered to the address of the node from the hub via the laser fiber of the string.

9. The device of claim 1, wherein the hub is configured to generate a regional ISOM with at least one regional informational map of a natural neuron event location which is taken from the phased array antenna and a local ISOM with at least one local informational map of a natural neuron event location which is taken from the a plurality of 3D array nodes, synthesize the regional ISOM and the local ISOM into a static ISOM frame that has a time-stamp, integrate the series of ISOMs from the static ISOM frame, and store at least one of the ISOM and the series of ISOMs in the memory of the hub.

10. The device of claim 9, wherein the hub is configured to retrieve at least one of the ISOM and the series of ISOMs in the memory, transmit, by using the phased array antenna, the electrical signals according to neuron address information in at least one of the ISOM and the series of ISOMs of the artificial neuron activity, and transmit, by using the plurality of 3D array nodes, at least one of the optical signals and the electrical signals according to the neuron address information in at least one of the ISOM and the series of ISOMs of the artificial neuron activity.

11. A method of whole-mind cognitive interface, comprising:
locating, by a detector of a hub in an artificial cranium cap, the hub comprising a cognitive computer, the detector; and a signal generator, at least one natural neuron event in a brain;
recording, by the cognitive computer of the hub, at least one of an instantaneous state of mind (ISOM) and a series of ISOMs by the located at least one natural neuron event;

replaying, by the signal generator of the hub paired with the cognitive computer of the hub, the at least one of the recorded ISOM and the recorded series of ISOMs through approximating the at least one of the recorded ISOM and the recorded series of ISOMs, wherein the approximating further comprises generating at least one artificial neuron activity in the brain; and, wherein the at least one artificial neuron activity is generated at a predetermined location of the brain, wherein the at least one natural neuron event is located by using at least one of a phased array radio frequency (RF) antenna and a plurality of 3D array nodes, wherein the phased array RF antenna is nested on an internal surface of the artificial cranium cap, under the control of the hub and communicatively coupled to the hub, wherein the method further comprises detecting, with the phased array RF antenna and the detector of the hub, at least one detected RF electromagnetic signal from the at least one natural neuron event and transmitting at least one transmitted RF electromagnetic signal for the at least one artificial neuron activity based on output of the signal generator, and wherein the plurality of 3D array nodes is inserted into the brain and under the control of the hub, and wherein the method further comprises detecting, with the plurality of 3D array nodes and the detector of the hub, the at least one electromagnetic signal from the at least one natural neuron event and transmitting, for the at least one artificial neuron activity, based on output of the signal generator, at least one of: optical signals by an optical source and the 3D array node electromagnetic signals by an electromagnetic signal source.

12. The method of claim 11, wherein the cognitive computer in the hub controls an electrical power unit in the hub to supply an electrical power, and maintains a condition of the electrical power, wherein the cognitive computer further controls at least one optical source which is connected to the 3D array nodes to generate the optical signals, and at least one optical detector which is connected to the 3D array nodes to detect the optical signals, wherein the cognitive computer further controls a capacitor bank which is connected to the 3D array nodes to trigger at least one spark gap event for the at least one artificial neuron activity, and an electromagnetic signal source which is connected to the phased array antenna to generate the 3D array node electromagnetic signals with a phase shifter.

13. The method of claim 11, wherein the artificial cranium cap replaces an organic cranium.

14. The method of claim 11, wherein the artificial cranium cap is externally worn on a human head, and the plurality of 3D array nodes are inserted into the brain via a plurality of cranium micro passageways on the human head.

15. The method of claim 11, wherein the phased array antenna, together with the detector of the hub, detects the at least one detected RF electromagnetic signal through a triangulation and a time-difference-of-arrival (TDOA) of the at least one detected RF electromagnetic signal and transmits the at least one transmitted RF electromagnetic signal through the triangulation of the at least one detected RF electromagnetic signal.

16. The method of claim 11, wherein a plurality of nodes of each 3D array node are linked by a string of the 3D array nodes, a first end of the string is connected to the hub and a second end of the string reaches to the end of the brain after being inserted into the brain, and the plurality of 3D array nodes forms a plurality of cubic space divisions that segments the brain with a predetermined volume, and wherein a node in the plurality of nodes of the plurality of 3D array nodes is located at each vertex of the cubic space division to detect the at least one electromagnetic signal within the cubic space division through a signal-strength-difference-on-arrival (SDOA).

17. The method of claim 16, wherein at least one of Ultraviolet (UV) and Infrared (IR) light passes through a plurality of laser fibers of the string between the hub and the node, electrical signals are delivered between the hub and the node via at least one semiconductor electrode energizing fiber that has a Gallium Arsenide (GaAs) layer and becomes conductive when at least UV light is sent to the semiconductor electrode energizing fiber from the hub, and the string includes at least one semiconductor ground that is a common ground for the at least one semiconductor electrode energizing fiber having the GaAs layer and becomes conductive when at least UV light is sent to the semiconductor ground from the hub, and at least one electrical conductor that delivers the electrical signals between the hub and the node.

18. The method of claim 16, wherein at least one local capacitor charge storage is paired with each node, a Radio Frequency Identification (RFID) of the node gives an address of the node to the phased array antenna via triangulation, an Optical Frequency Identification (OFID) of the node gives the address of the node to the hub, at least one photodiode of the node triggers the at least one spark gap event from at least one optical signal being controlled by the hub and causes at least one local artificial neuron activity, a spark gap unit of the node triggers the at least one spark gap event from at least one electrical signal being controlled by the hub and causes the at least one local artificial neuron activity, a conductive shell of the node transmits the 3D array node electromagnetic signals from the at least one spark gap event to cause the at least one local artificial neuron activity and detects the at least one electromagnetic signal from the at least one natural neuron event, at least one electrode of the node charges the conductive shell and becomes a terminal point of signals from the hub by controlling of the hub, and a plurality of micro-scale windows on the conductive shell are for an omnidirectional dispersion of lights which are delivered to the address of the node from the hub via the laser fibers.

19. The method of claim 11, wherein recording of the hub further comprises:
generating, by the hub, a regional ISOM with at least one regional informational map of natural neuron event location which is taken from the phased array antenna;
generating, by the hub, a local ISOM with at least one local informational map of the natural neuron event location which is taken from the plurality of 3D array nodes, and the hub;
synthesizing, by the hub, the regional ISOM and the local ISOM into a static ISOM frame that has a time-stamp;
integrating, by the hub, the series of ISOMs from the static ISOM frame; and
storing, by the hub, at least one of the ISOM and the series of ISOMs in a memory of the hub.

20. The method of claim 19, wherein replaying of the hub further comprises:
retrieving, by the hub, at least one of the ISOM and the series of ISOMs in the memory;
transmitting, by phased array antenna being controlled by the hub, the electrical signals according to neuron address information in at least one of the ISOM and the series of ISOMs for the artificial neuron activity; and transmitting, by the plurality of 3D array nodes being controlled by the hub, at least one of the optical signals and the electrical signals according to the neuron address information in at least one of the ISOM and the series of ISOMs for the artificial neuron activity.

* * * * *